(12) United States Patent
Zhao et al.

(10) Patent No.: US 8,367,065 B2
(45) Date of Patent: Feb. 5, 2013

(54) TARGETED POLYMERIC PRODRUGS CONTAINING MULTIFUNCTIONAL LINKERS

(75) Inventors: Hong Zhao, Edison, NJ (US); Prasanna Reddy, Somerset, NJ (US); Maria Belen Rubio, Somerset, NJ (US)

(73) Assignee: Enzon Pharmaceuticals, Inc., Piscataway, NJ (US)

( * ) Notice: Subject to any disclaimer, the term of this patent is extended or adjusted under 35 U.S.C. 154(b) by 148 days.

(21) Appl. No.: 12/402,839

(22) Filed: Mar. 12, 2009

(65) Prior Publication Data

US 2010/0233190 A1   Sep. 16, 2010

Related U.S. Application Data

(63) Continuation of application No. PCT/US2007/078600, filed on Sep. 15, 2007.

(60) Provisional application No. 60/844,943, filed on Sep. 15, 2006.

(51) Int. Cl.
| | |
|---|---|
| *A61K 47/48* | (2006.01) |
| *A61K 31/4015* | (2006.01) |
| *A61K 31/4025* | (2006.01) |
| *A61K 31/444* | (2006.01) |
| *A61K 31/44* | (2006.01) |
| *A61K 31/7088* | (2006.01) |
| *A61K 39/395* | (2006.01) |
| *C07H 21/02* | (2006.01) |
| *C07K 16/00* | (2006.01) |
| *C07K 17/02* | (2006.01) |
| *C07D 207/40* | (2006.01) |
| *C07D 403/12* | (2006.01) |

(52) U.S. Cl. ............ 424/179.1; 536/23.1; 530/391.1; 530/300; 530/395; 548/546; 548/520; 546/261; 546/294; 540/460; 514/425; 514/422; 514/335; 514/347; 514/81

(58) Field of Classification Search .................. None
See application file for complete search history.

(56) References Cited

U.S. PATENT DOCUMENTS

| | | | |
|---|---|---|---|
| 5,643,575 A * | 7/1997 | Martinez et al. | 424/194.1 |
| 6,153,655 A | 11/2000 | Martinez et al. | |
| 6,214,330 B1 * | 4/2001 | Greenwald et al. | 424/78.01 |
| 6,303,569 B1 * | 10/2001 | Greenwald et al. | 514/1.3 |
| 6,331,289 B1 * | 12/2001 | Klaveness et al. | 424/9.52 |
| 6,395,266 B1 | 5/2002 | Martinez et al. | |
| 6,638,499 B2 | 10/2003 | Martinez et al. | |
| 6,743,908 B2 * | 6/2004 | Filpula et al. | 536/23.53 |
| 6,777,387 B2 * | 8/2004 | Greenwald et al. | 530/350 |
| 6,872,393 B2 | 3/2005 | Whitlow et al. | |
| 7,011,812 B1 * | 3/2006 | Griffiths et al. | 424/1.49 |
| 7,026,440 B2 | 4/2006 | Bentley et al. | |
| 7,595,304 B2 * | 9/2009 | Zhao et al. | 514/44 R |
| 2003/0096743 A1 * | 5/2003 | Senter et al. | 514/12 |
| 2004/0142858 A1 * | 7/2004 | Greenwald et al. | 514/8 |
| 2004/0235773 A1 * | 11/2004 | Zhao et al. | 514/44 |
| 2006/0130160 A1 | 6/2006 | Dumas Milne Edwards et al. | |
| 2009/0221471 A1 * | 9/2009 | Greenwald et al. | 514/8 |

FOREIGN PATENT DOCUMENTS

| | | |
|---|---|---|
| WO | WO 2004044224 A2 * | 5/2004 |
| WO | 2008/034120 | 3/2008 |
| WO | 2008/034123 | 3/2008 |

OTHER PUBLICATIONS

International Search Report and Written Opinion issued in PCT/US2007/078600 and dated Mar. 25, 2008.

Sun, C., et al. Enabling ScFvs as multi-drug carriers: a dendritic approach. Bioorg Med Chem. Apr. 17, 2003; 11 (8):1761-1768.

Sun, C., et al. Syntheses of dendritic linkers containing chlorambucil residues for the preparation of antibody-multidrug immunoconjugates. Biorf Med Chem Lett. Aug. 19, 2002; 12(16):2213-2215.

A. Natarajan, et al., Characterization of site-specific ScFv PEGylation for tumor-targeting pharmaceuticals. Bioconjug Chem. Jan.-Feb. 2005; 16(1): 113-121.

Dunehoo, Alison, et al., Cell Adhesion Molecules for Targeted Drug Delivery. J. Pharm. Sci., Sep. 2006; 9 (95):1856-1872.

Mäe, et al., Cell-penetrating peptides as vectors for peptide, protein and oligonucleotide delivery, Curr. Opin. Pharmacol. 2006, 6:509-514.

\* cited by examiner

*Primary Examiner* — Yong Chu

(74) *Attorney, Agent, or Firm* — Lucas & Mercanti, LLP

(57) ABSTRACT

The present invention provides single chain antibody-directed polymeric prodrugs containing multifunctional linkers. Methods of making the polymeric delivery systems and methods of treating mammals using the same are also disclosed.

19 Claims, 13 Drawing Sheets

Preparation of PEG amide heterobifunctional linker (maleimide/activated carboxylic acid)

Preparation of PEG carbamate heterobifunctional linker (maleimide/activated carboxylic acid)

Preparation of PEG-carbamate-Lys(RGDC)-NHOligo

Synthesis of Boc-Val-Cit-PABE-SN38 (Method A)

Synthesis of Boc-Val-Cit-PABE-SN38 (Method B)

Synthesis of PEG-carbamate-Lys(RGDC)-Val-Cit-PABE-SN38

Synthesis of PEG carbamate heterobifunctional linker (NPys/activated carboxylic acid)

Synthesis of BocPheLys(Fmoc)-NH-PABE-SN38

Synthesis of PEG-carbamate-Lys(Cys(RGDC))-Phe-Lys-PABE-SN38

Synthesis of PEG-carbamate-Lys(Cys(NPys))-Val-Cit-PAB-OH

Synthesis of PEG-carbamate-Lys(Cys(RGDC))-Val-Cit-PAB-Dox

Synthesis of PEG carbamate heterobifunctional linker (NPys/amine)

Synthesis of PEG-carbamate-Lys(folate)-Cys-S-Oligo

TARGETED POLYMERIC PRODRUGS CONTAINING MULTIFUNCTIONAL LINKERS

CROSS-REFERENCE TO RELATED APPLICATION

This patent application is a continuation of PCT/US2007/078600, filed Sep. 15, 2007, which claims the benefit of priority from U.S. Provisional Patent Application No. 60/844,943, filed Sep. 15, 2006, the contents of each of which are incorporated herein by reference.

BACKGROUND OF INVENTION

It is known that many of small molecular weight anticancer agents have significant toxicity. Over the years, there have been various attempts to reduce the toxicity and improve the efficacy of small molecular weight anti-cancer agents.

One attempt to reduce the toxicity and improve the efficacy of small molecular weight drugs was directed to targeting agent-directed drug delivery systems. For example, the targeting agent such as single-chain antibody, RGD peptides, or folic acid, can direct the delivery of the therapeutic agent and improve its therapeutic effect. At the same time, the targeted delivery of very potent chemotherapeutics would reduce its toxicity. The approach has been validated by FDA's approval of, for example, Wyeth's Mylotarg® gemtuzumab zogamicin, a humanized antibody against CD33 linked to the calicheamicin cytotoxin, for acute myeloid leukemia (AML).

Traditionally, the immunoconjugates include three components: a targeting agent like a monoclonal antibody, a cytotoxin and a linker.

However, this approach requires that the antibody retain high degree of its binding affinity to its antigen after conjugation to the drug. Furthermore, the antibody-drug conjugates have to be stable in buffers or plasma and not prematurely release the toxin during circulation. They must also be internalized once the antibody binds its antigen on tumor cell surface. Thereafter, the drug molecule has to be released intact inside the targeted tumor cells at a desired speed.

Single chain antibodies (SCA's) or single-chain antigen-binding antibodies include the binding domain of full length antibody with only one fourth of the size. However, SCA can bind to antigen specifically with high affinity. A description of the theory and production of single-chain antigen-binding proteins is found, for example, in commonly-assigned U.S. Pat. Nos. 4,946,778, 5,260,203, 5,455,030 and 5,518,889. The single-chain antigen-binding proteins produced under the process recited in the above U.S. patents have binding specificity and affinity substantially similar to that of the corresponding Fab fragment, the content of which are incorporated by reference herein. More recently, commonly-assigned U.S. Pat. No. 6,872,393 disclosed polyalkylene oxide-modified single chain polypeptides. The contents of each of the foregoing commonly-assigned patents are incorporated herein by reference.

In spite of the attempts and advances, there continues to be a need to provide targeting agent-directed polymeric drug delivery system having desired therapeutic activity and less toxicity. The present invention addresses this need and others.

SUMMARY OF THE INVENTION

In order to overcome the above problems and improve the technology for polymeric drug delivery, there are provided new and advantageous compounds which employ the use of both targeting agent and PEGylation technologies as well as other improved therapeutic techniques. Therefore, in accordance with one aspect of the invention there are provided compounds of Formula (I):

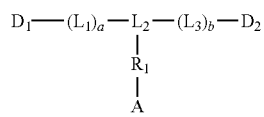

wherein:

$R_1$ is a substantially non-antigenic water-soluble polymer;
A is a capping group or

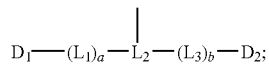

each $D_1$ is independently selected from among targeting moieties, functional groups and leaving groups, preferably targeting moieties;

each $D_2$ is independently selected from among biologically active moieties, functional groups and leaving groups, preferably biologically active moieties;

each $L_1$ is an independently a permanent linker or a releasable linker, preferably permanent linker;

$L_2$ is a multifunctional linker;

each $L_3$ is an independently a permanent linker or a releasable linker, preferably releasable linker; and (a) and (b) are independently zero or a positive integer, preferably zero or 1.

In one aspect of the invention, the polymer residue is a polyethylene oxide which can be conjugated to both small drug molecules and single chain antibody (SCA) through releasable linkers and permanent linkers through multifunctional linkers. In this way, there are provided compounds to provide SCA-PEG-Linker-Drug delivery platform for targeted delivery of small molecule cytotoxic compounds. Additionally, it is advantageous that the loading of both small molecule and SCA per attaching site are increased over the traditional SCA-drug conjugates. Therefore, there can be provided cost-effective, low-cost, targeted SCA prodrugs. Furthermore, the prodrugs of the present invention provide methods of regulating circulating half-life of the drugs, for example, increasing circulating half-life, when desired, by using proper linkers.

One general aspect of the present invention, without limitation, is schematically described in the following structure:

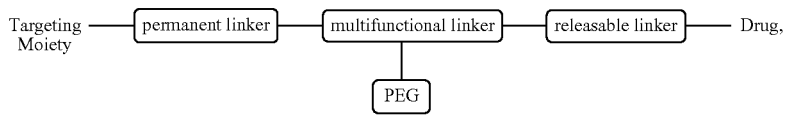

wherein PEG is attached to both the SCA and the drug such as a cytotoxic agent through a centrally-located multifunctional linker; the linker with the SCA is permanent, while the linker with the cytotoxic agent is releasable and can be designed to be stable in blood, but easily degradable in the presence of a site specific enzyme.

In one preferred aspect, the SCA is attached through a permanent linker such as one containing a maleimide group and the cytotoxic agent through a releasable linker such as a peptidyl linker (Val-Cit) which can be specifically degraded by capthesin B. In one preferred embodiment, the cytotoxic agent is SN38.

Further aspects of the invention include methods of making the activated polymers containing multifunctional linkers, methods of making conjugates containing the same as well as methods of treatment based on administering effective amounts of conjugates containing a biologically active moiety to a patient (mammal) in need thereof.

One of the advantages of the present invention is that the polymeric delivery systems described herein are stable and thus enhance bioavailability of drugs.

Another advantage of the present invention is that the polymeric delivery systems can release drugs intact inside the targeted tumor cells.

Yet another advantage is that the release rate of the drugs can be modified to achieve a desired speed.

Yet another advantage of the polymeric systems corresponding to the invention is that they are well suited for small molecular weight drugs and oligonucleotides such as antisense, short-interfering RNA (siRNA) or LNA compounds.

Other and further advantages will be apparent from the following description.

For purposes of the present invention, the term "residue" shall be understood to mean that portion of a compound, to which it refers, i.e. cytotoxin, SN38, permanent linker, multifunctional linker, releasable linker, etc. that remains after it has undergone a substitution reaction with another compound.

For purposes of the present invention, the term "polymeric residue" or "PEG residue" shall each be understood to mean that portion of the polymer or PEG which remains after it has undergone a reaction with other compounds, moieties, etc.

For purposes of the present invention, substituted alkyls include carboxyalkyls, aminoalkyls, dialkylaminos, hydroxyalkyls and mercaptoalkyls; substituted alkenyls include carboxyalkenyls, aminoalkenyls, dialkenylaminos, hydroxyalkenyls and mercaptoalkenyls; substituted alkynyls include carboxyalkynyls, aminoalkynyls, dialkynylaminos, hydroxyalkynyls and mercaptoalkynyls; substituted cycloalkyls include moieties such as 4-chlorocyclohexyl; aryls include moieties such as napthyl; substituted aryls include moieties such as 3-bromo phenyl; aralkyls include moieties such as tolyl; heteroalkyls include moieties such as ethylthiophene; substituted heteroalkyls include moieties such as 3-methoxy-thiophene; alkoxy includes moieties such as methoxy; and phenoxy includes moieties such as 3-nitrophenoxy. Halo shall be understood to include fluoro, chloro, iodo and bromo.

For purposes of the present invention, "nucleic acid" or "nucleotide" shall be understood to include deoxyribonucleic acid (DNA), ribonucleic acid (RNA) whether single-stranded or double-stranded, unless otherwise specified, and any chemical modifications thereof.

For purposes of the present invention, the terms "a biologically active moiety" and "a residue of a biologically active moiety" shall be understood to mean that portion of a biologically active compound which remains after the biologically active compound has undergone a substitution reaction in which the transport carrier portion has been attached.

For ease of description and not limitation, it will be understood that the term "biologically active moieties" is interchangeable with "drugs", "cytotoxic agents", "cytotoxins".

For ease of description and not limitation, it will be understood that the term "small molecules" are interchangeable with "pharmaceutically active compounds".

Unless otherwise defined, for purposes of the present invention:

the term "alkyl" shall be understood to include straight, branched, substituted, e.g. halo-, alkoxy-, and nitro-$C_{1-12}$ alkyls, $C_{3-8}$ cycloalkyls or substituted cycloalkyls, etc.;

the term "substituted" shall be understood to include adding or replacing one or more atoms contained within a functional group or compound with one or more different atoms;

the term "substituted alkyls" include carboxyalkyls, aminoalkyls, dialkylaminos, hydroxyalkyls and mercaptoalkyls;

the term "substituted cycloalkyls" include moieties such as 4-chlorocyclohexyl; aryls include moieties such as napthyl; substituted aryls include moieties such as 3-bromophenyl; aralkyls include moieties such as toluyl; heteroalkyls include moieties such as ethylthiophene;

the term "substituted heteroalkyls" include moieties such as 3-methoxy-thiophene; alkoxy includes moieties such as methoxy; and phenoxy includes moieties such as 3-nitrophenoxy;

the term "halo" shall be understood to include fluoro, chloro, iodo and bromo; and the terms "sufficient amounts" and "effective amounts" for purposes of the present invention shall mean an amount which achieves a therapeutic effect as such effect is understood by those of ordinary skill in the art.

DETAILED DESCRIPTION OF THE INVENTION

A. Overview

Figure 1:
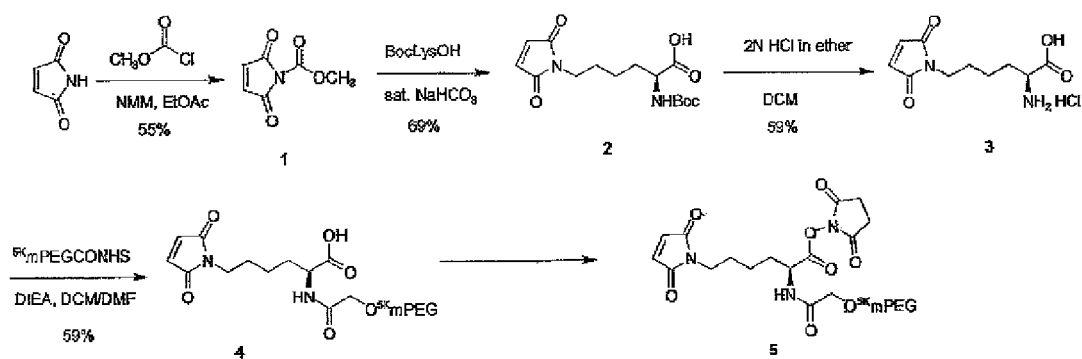
FIG. 1 schematically illustrates methods of synthesis described in Examples 1-5.
Figure 2:
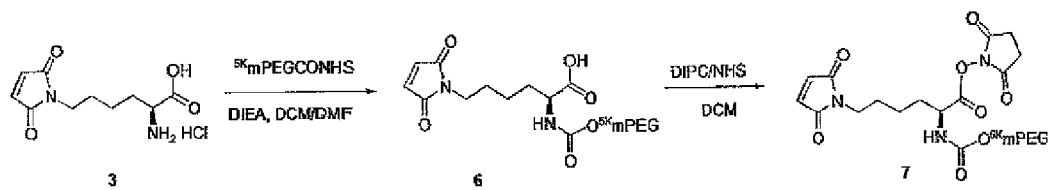
FIG. 2 schematically illustrates methods of synthesis described in Examples 6-7.
Figure 3:
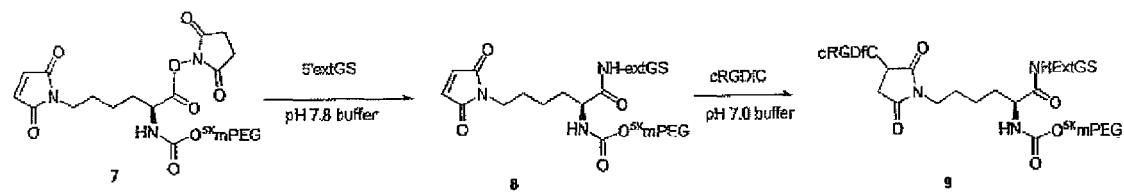
FIG. 3 schematically illustrates methods of synthesis described in Examples 8-9.
Figure 4:
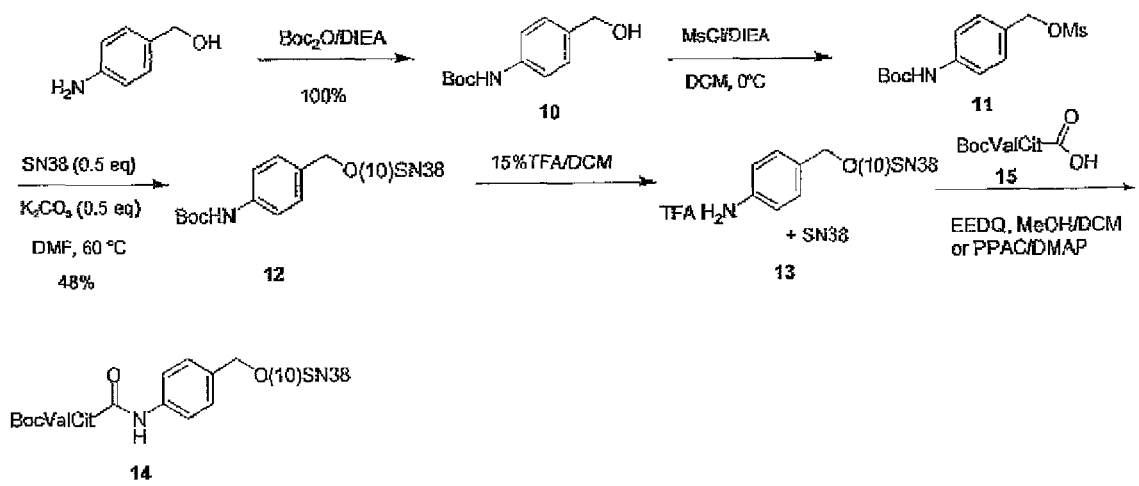
FIG. 4 schematically illustrates methods of synthesis described in Examples 10-14.
Figure 5:
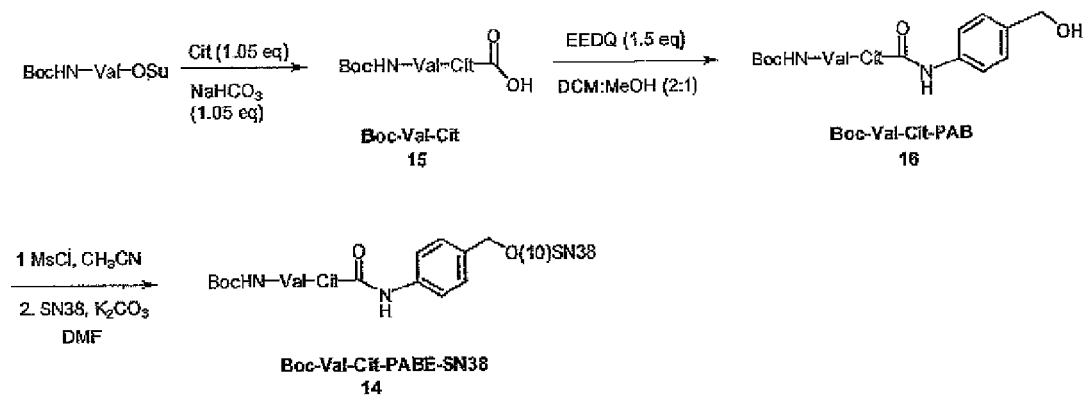
FIG. 5 schematically illustrates methods of synthesis, described in Examples 15-17.
Figure 6:
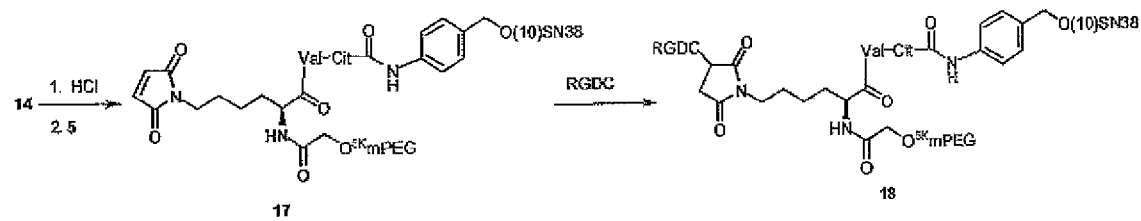
FIG. 6 schematically illustrates methods of synthesis described in Examples 18-19.
Figure 7:
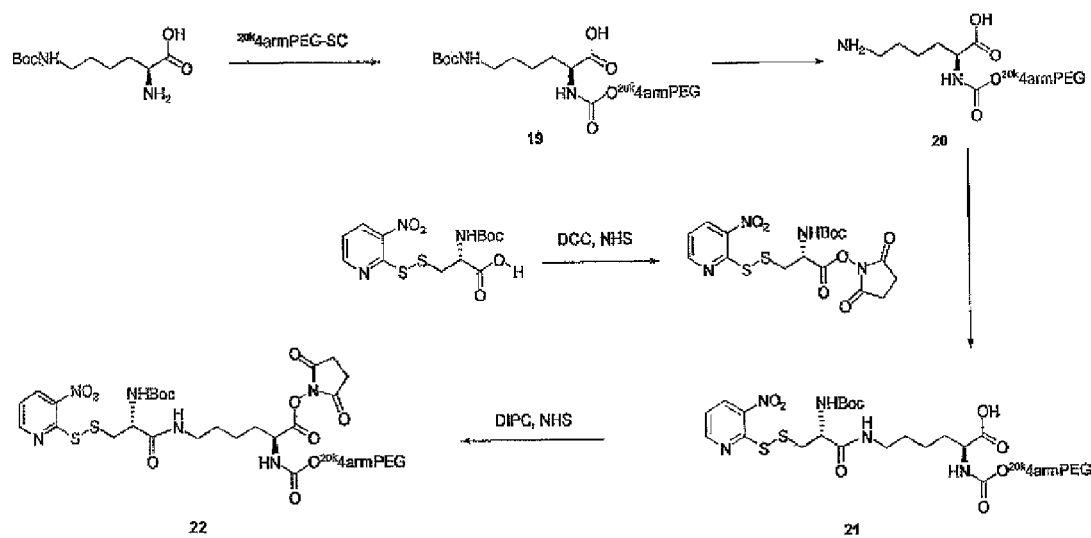
FIG. 7 schematically illustrates methods of synthesis described in Examples 20-23.
Figure 8:
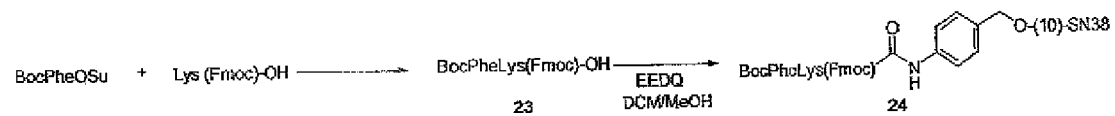
FIG. 8 schematically illustrates methods of synthesis described in Examples 24-25.
Figure 9:
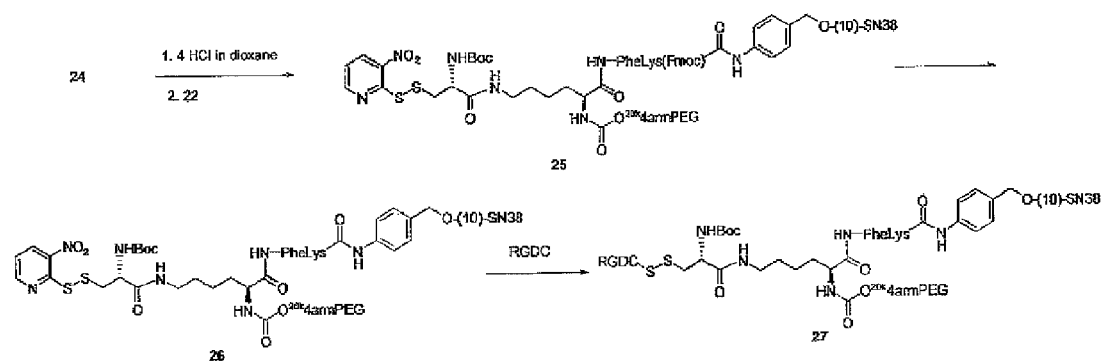
FIG. 9 schematically illustrates methods of synthesis described in Examples 26-28.
Figure 10:
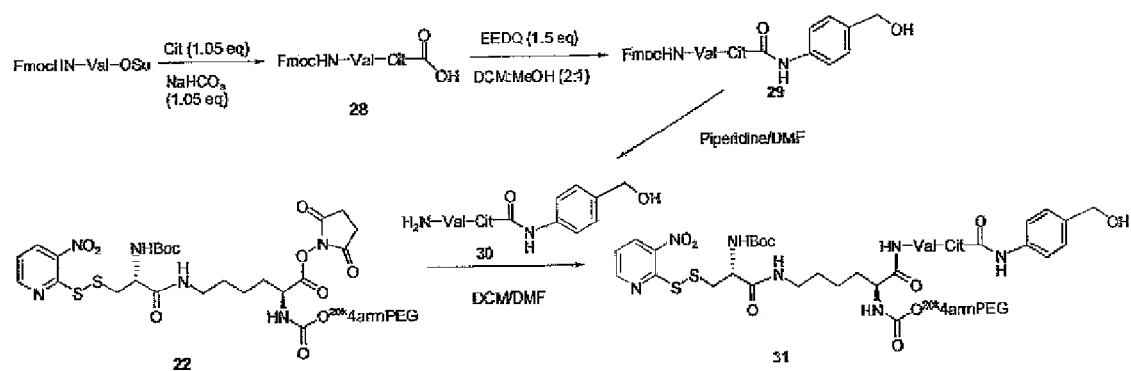
FIG. 10 schematically illustrates methods of synthesis described in Examples 29-32.
Figure 11:
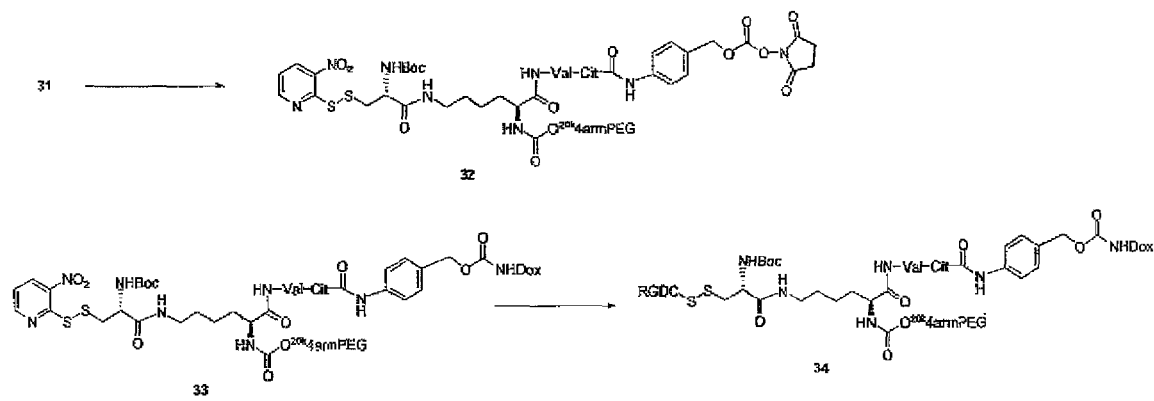
FIG. 11 schematically illustrates methods of synthesis described in Examples 33-35.
Figure 12:
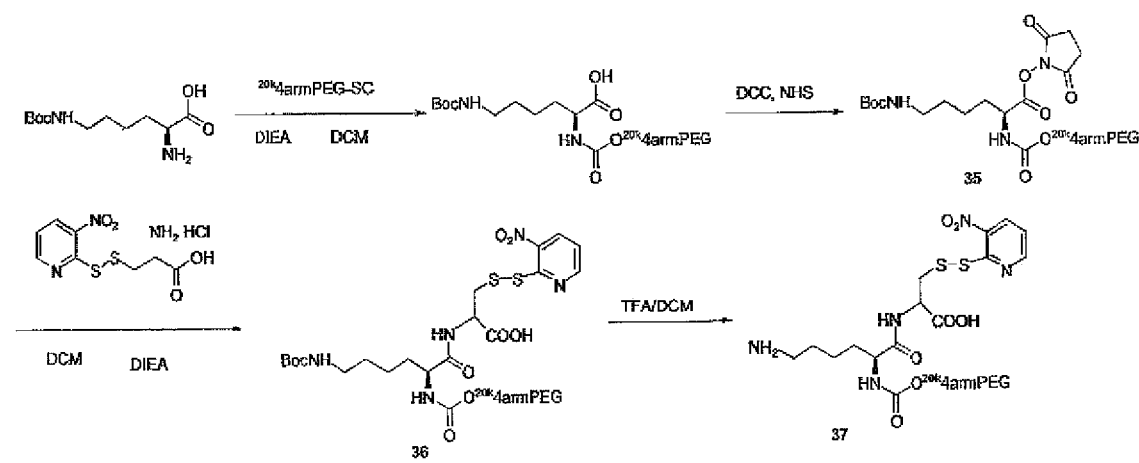
FIG. 12 schematically illustrates methods of synthesis described in Examples 36-38.
Figure 13:
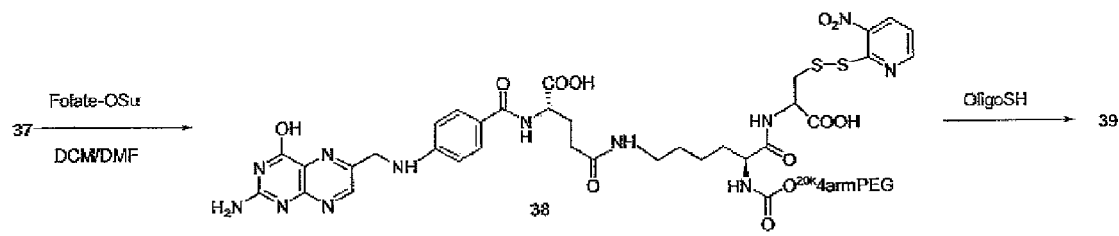
FIG. 13 schematically illustrates methods of synthesis described in Examples 39-40.

In one aspect of the present invention, there are provided compounds of Formula (I):

$$D_1-(L_1)_a-L_2-(L_3)_b-D_2$$
$$|$$
$$R_1$$
$$|$$
$$A$$
(I)

wherein:

$R_1$ is a substantially non-antigenic water-soluble polymer;

A is a capping group or $$D_1-(L_1)_a-L_2-(L_3)_b-D_2;$$

each $D_1$ is independently selected from among targeting moieties, functional groups and leaving groups, preferably targeting moieties;

each $D_2$ is independently selected from among biologically active moieties, functional groups and leaving groups, preferably biologically active moieties;

each $L_1$ is an independently a permanent linker or a releasable linker, preferably permanent linker;

$L_2$ is a multifunctional linker;

each $L_3$ is an independently a permanent linker or a releasable linker, preferably releasable linker; and (a) and (b) are independently zero or a positive integer, preferably zero or 1.

In one preferred aspect of the invention, the targeted polymeric delivery systems include compounds having formula:

(IIa), (IIb), (IIc), (IId), (IIe), (IIf), (IIg), (IIh), (IIi), and (IIj)

wherein $R_2$ and $R'_2$ are independently selected from among hydrogen, $C_{1-6}$ alkyl, $C_{2-6}$ alkenyl, $C_{2-6}$ alkynyl, $C_{3-19}$ branched alkyl, $C_{3-8}$ cycloalkyl, $C_{1-6}$ substituted alkyl, $C_{2-6}$ substituted alkenyl, $C_{2-6}$ substituted alkynyl, $C_{3-8}$ substituted cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-6}$ substituted alkanoyl, substituted arylcarbonyl, $C_{2-6}$ substituted alkanoyloxy, substituted aryloxycarbonyl, $C_{2-6}$ substituted alkanoyloxy and substituted arylcarbonyloxy;

(c1), (c2), (c3), (c4), (c5), (c6), (c'6), (c"6), (c7) and (c8) are independently zero or a positive integer, preferably zero or an integer from about 1 to about 10, and more preferably zero, 1 or 2;

(d1), (d2), (d3), (d4), (d5) and (d7) are independently zero or a positive integer, preferably zero or an integer from about 1 to about 10, and more preferably zero or an integer from about 1 to about 4; and all other variables are previously defined.

In another aspect, the polymeric systems described herein are either capped on one terminal with a $CH_3$ group, i.e. mPEG while in other embodiments, bis-activated PEGs are provided such as those corresponding to the formula:

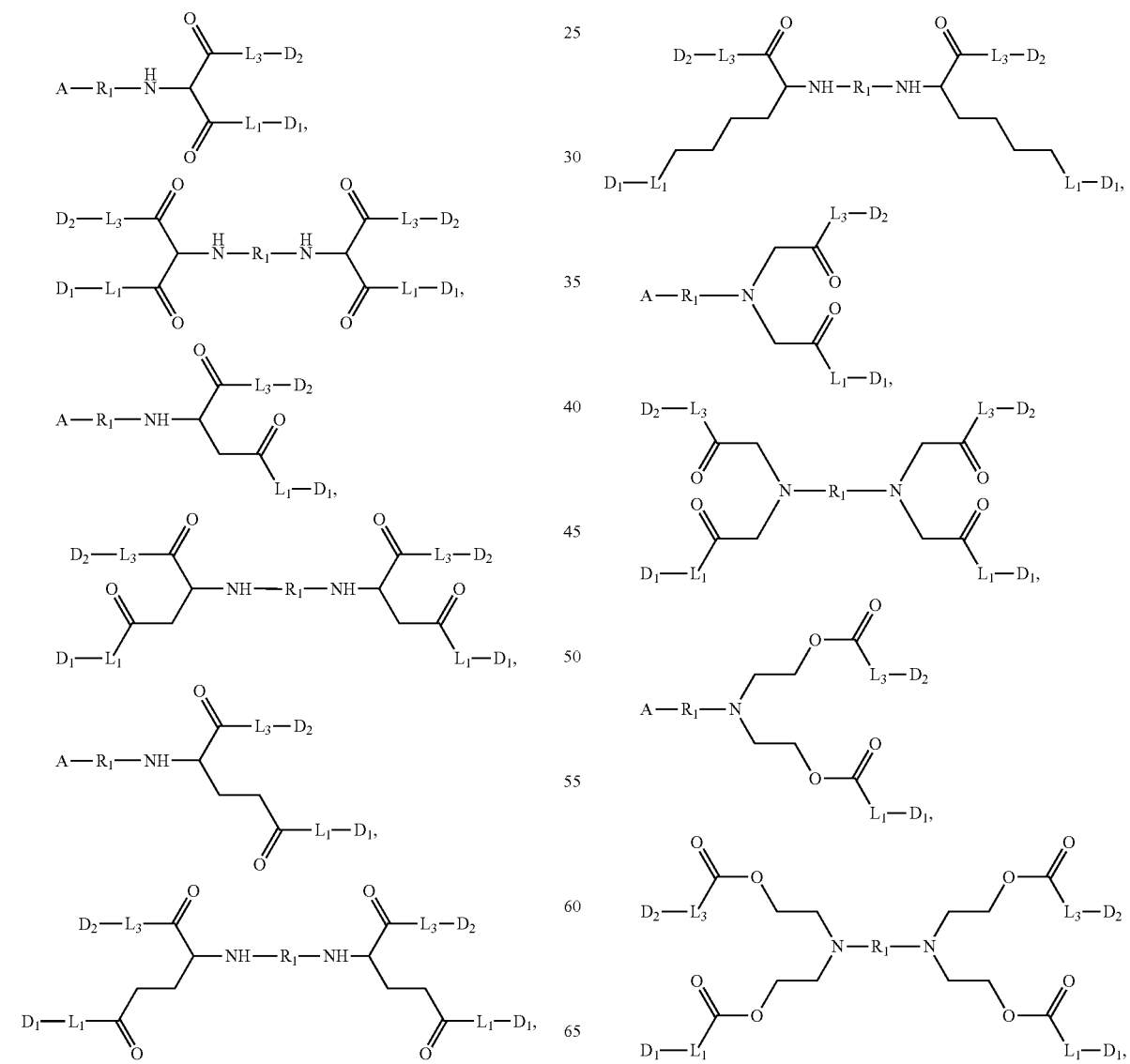

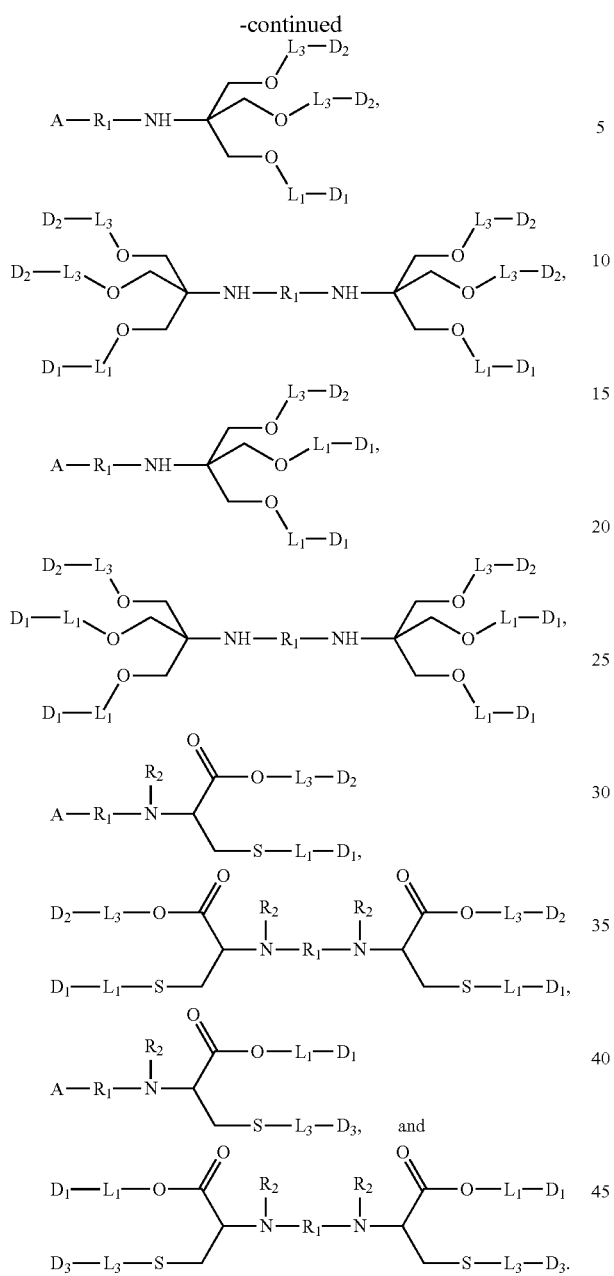

B. Multifunctional Linkers ($L_2$)

In view of the structure of the present invention, the multifunctional linker allows attaching (releasable or permanent) 3 or more components, i.e. a targeting agent, a polymer and a biologically active cytotoxic compound like SN38. The artisan can appreciate that other molecules including at least three independent functional groups can also be used. One preferred multifunctional linker can be a residue of an aspartic acid or a lysine.

The $L_2$ having at least three functional site can be selected from among:

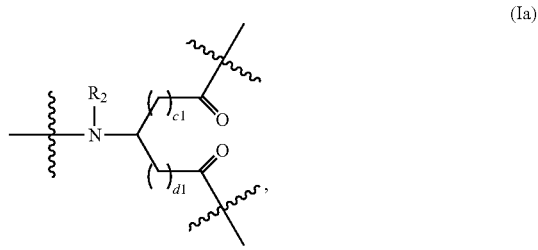

(Ia)

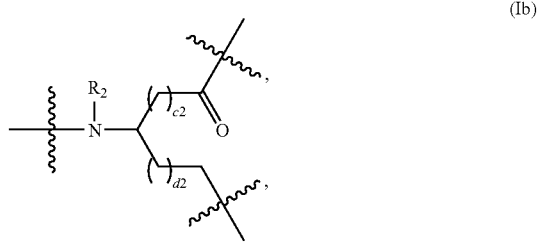

(Ib)

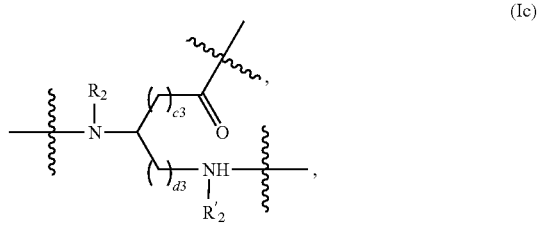

(Ic)

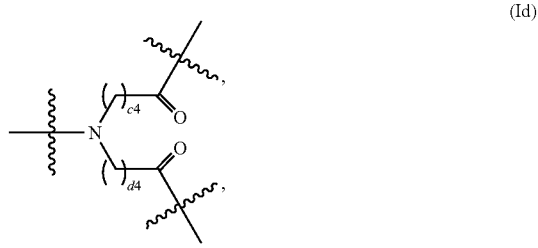

(Id)

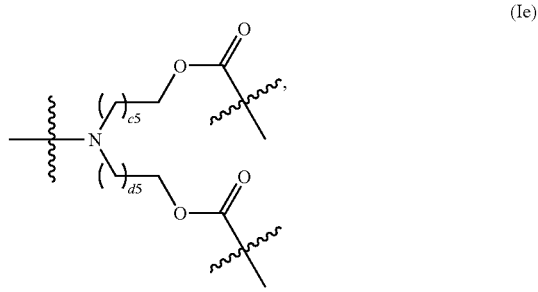

(Ie)

Other optional capping groups include H, $NH_2$, OH, $CO_2H$, $C_{1-6}$ alkoxy and $C_{1-6}$ alkyl. Preferred capping groups include methoxy and methyl.

In most aspects of the invention, the polymers included herein are generally described as substantially non-antigenic polymers. Within this genus of polymers, polyalkylene oxides are preferred and polyethylene glycols (PEG's) are most preferred. For purposes of ease of description rather than limitation, the invention is sometimes described using PEG as the prototypical polymer. It should be understood, however, that the scope of the invention is applicable to a wide variety of polymers which can be linear, substantially linear, branched, etc.

In another aspect of the invention, the biological moieties include —$NH_2$ containing moieties, —OH containing moieties and —SH containing moieties.

-continued (If)
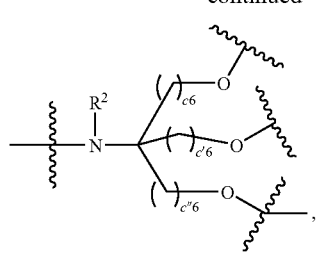

(Ig)
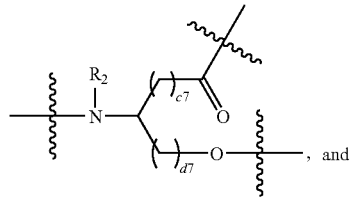
, and (Ih)
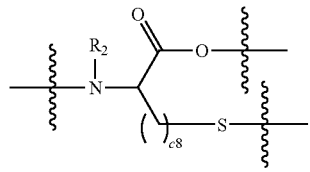

wherein $R_2$ and $R'_2$ are independently selected from among hydrogen, $C_{1-6}$ alkyl, $C_{2-6}$ alkenyl, $C_{2-6}$ alkynyl, $C_{3-19}$ branched alkyl, $C_{3-8}$ cycloalkyl, $C_{1-6}$ substituted alkyl, $C_{2-6}$ substituted alkenyl, $C_{2-6}$ substituted alkynyl, $C_{3-8}$ substituted cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-6}$ substituted alkanoyl, substituted arylcarbonyl, $C_{2-6}$ substituted alkanoyloxy, substituted aryloxycarbonyl, $C_{2-6}$ substituted alkanoyloxy and substituted arylcarbonyloxy;

(c1), (c2), (c3), (c4), (c5), (c6), (c'6), (c"6), (c7) and (c8) are previously defined; and (d1), (d2), (d3), (d4), (d5) and (d7) are also previously defined.

Preferred embodiments include:

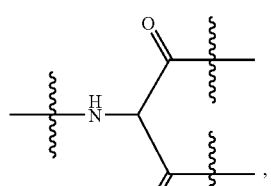
,

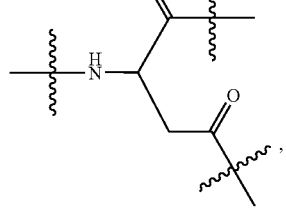
,

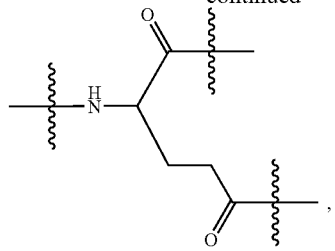
,

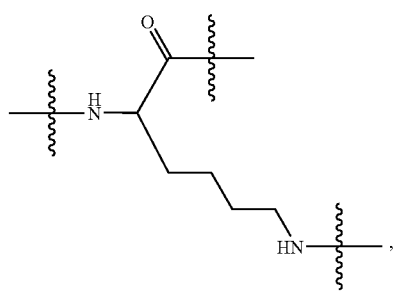
,

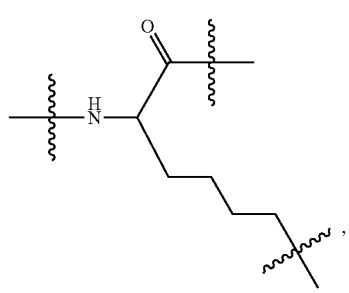
,

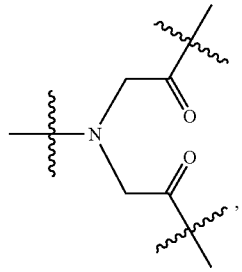
,

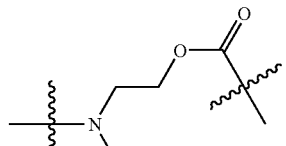
,

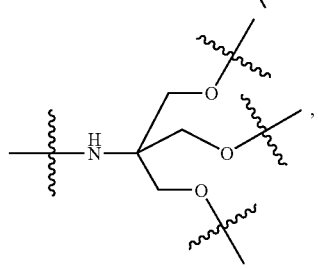
,

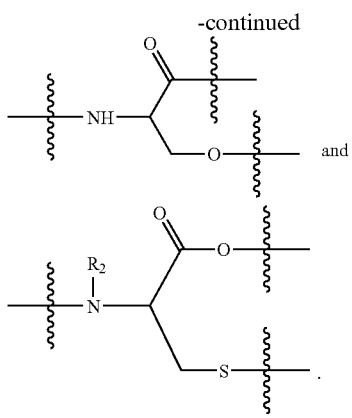

and

C. Substantially Non-Antigenic Water-Soluble Polymers ($R_1$)

The prodrugs of the present invention include a polymer residue $R_1$, preferably water-soluble and substantially non-antigenic polymers. Suitable examples of such polymers include polyalkylene oxides (PAO) such as polyethylene glycols. Certain preferred polymers are polyethylene glycols such as mPEG. A non-limiting list of such polymers therefore includes polyalkylene oxide homopolymers such as polyethylene glycol (PEG) or polypropylene glycols, polyoxyethylenated polyols, copolymers thereof and block copolymers thereof.

The polymer portion of the compounds described herein has an average molecular weight from about 2,000 to about 100,000 daltons, preferably from about 5,000 to about 60,000 daltons. In some aspects, the polyalkylene oxide can be from about 5,000 to about 25,000, and preferably from about 12,000 to about 20,000 daltons when proteins or oligonucleotides are attached or alternatively from about 20,000 to about 45,000 daltons, and preferably from about 30,000 to about 40,000 daltons when pharmaceutically active compounds (small molecules such as those having an average molecular weight of less than about 1,500 daltons) are employed in the compounds described herein.

Polyethylene glycol (PEG) is generally represented by the structure:

—O—(CH$_2$CH$_2$O)$_n$— where (n) is an integer from about 10 to about 2,300, and is dependent on the number of polymer arms when multi-arm polymers are used. It will be understood that the water-soluble polymer will be functionalized for attachment to linkers.

Alternatively, the polyethylene glycol (PEG) residue portion of the invention can be represented by the structure:

—Y$_{71}$—(CH$_2$CH$_2$O)$_n$—CH$_2$CH$_2$Y$_{71}$—,
—Y$_{71}$—(CH$_2$CH$_2$O)$_n$—CH$_2$C(=Y$_{72}$)—Y$_{71}$—,
—Y$_{71}$—C(=Y$_{72}$)—(CH$_2$)$_{a71}$—Y$_{73}$—(CH$_2$CH$_2$O)$_n$—CH$_2$CH$_2$—Y$_{73}$—(CH$_2$)$_{a71}$—C(=Y$_{72}$)—Y$_{71}$—,
—Y$_{71}$—(CR$_{71}$R$_{72}$)$_{a72}$—Y$_{73}$—(CH$_2$)$_{b71}$—O—(CH$_2$CH$_2$O)$_n$—(CH$_2$)$_{b71}$—Y$_{73}$—(CR$_{71}$R$_{72}$)$_{a72}$—Y$_{71}$—,
—Y$_{71}$—(CH$_2$CH$_2$O)$_n$—CH$_2$CH$_2$—,
—Y$_{71}$—(CH$_2$CH$_2$O)$_n$—CH$_2$C(=Y$_{72}$)—,
—C(=Y$_{72}$)—(CH$_2$)$_{a71}$—Y$_{73}$—(CH$_2$CH$_2$O)$_n$—CH$_2$CH$_2$—Y$_{73}$—(CH$_2$)$_{a71}$—C(=Y$_{72}$)—, and
—(CR$_{71}$R$_{72}$)$_{a72}$—Y$_{73}$—(CH$_2$)$_{b71}$—O—(CH$_2$CH$_2$O)$_n$—(CH$_2$)$_{b71}$—Y$_{73}$—(CR$_{71}$R$_{72}$)$_{a72}$—, wherein:

$Y_{71}$ and $Y_{73}$ are independently O, S, SO, SO$_2$, NR$_{73}$ or a bond;

$Y_{72}$ is O, S, or NR$_{74}$;

$R_{71-74}$ are independently the same moieties which can be used for $R_2$;

(a71), (a72), and (b71) are independently zero or a positive integer, preferably 0-6, and more preferably 1; and (n) is an integer from about 10 to about 2300.

As an example, the PEG can be functionalized in the following non-limiting manner:

—C(=Y$_{74}$)—(CH$_2$)$_m$—(CH$_2$CH$_2$O)$_n$—,
—C(=Y$_{74}$)—Y—(CH$_2$)$_m$—(CH$_2$CH$_2$O)$_n$—,
—C(=Y$_{74}$)—NR$_{11}$—(CH$_2$)$_m$—(CH$_2$CH$_2$O)$_n$—,
—CR$_{75}$R$_{76}$—(CH$_2$)$_m$—(CH$_2$CH$_2$O)$_n$— wherein $R_{75}$ and $R_{76}$ are independently selected from among of H, $C_{1-6}$ alkyls, aryls, substituted aryls, aralkyls, heteroalkyls, substituted heteroalkyls and substituted $C_{1-6}$ alkyls;

m is zero or is a positive integer, and preferably 1;

$Y_{74}$ is O or S; and n represents the degree of polymerization.

Although, the prodrugs of the present invention can be formed using any of the substantially non-antigenic polymers described herein, some preferred polyalkylene oxides include:

CH$_3$O-PEG-O—(CH$_2$)$_m$—CO$_2$H;
PEG-NHS;
CH$_3$O-PEG-O—(CH$_2$)$_m$—NR$_{11}$R$_{12}$; and
CH$_3$O-PEG-O—(CH$_2$)$_2$—S—(CH$_2$)$_m$—CO2H;
SC-PEG; or
any of the art recognized activated PEGs.

In particular, polyethylene glycols (PEG's), mono-activated, $C_{1-4}$ alkyl-terminated PAO's such as mono-methyl-terminated polyethylene glycols (mPEG's) are preferred when mono-substituted polymers are desired; bis-activated polyethylene oxides are preferred when disubstituted prodrugs are desired.

In order to provide the desired linkage, mono- or di-acid activated polymers such as PEG acids or PEG diacids are used. Suitable PAO acids can be synthesized by converting mPEG-OH to an ethyl ester. See also Gehrhardt, H., et al. Polymer Bulletin 18: 487 (1987) and Veronese, F. M., et al., J. Controlled Release 10; 145 (1989). Alternatively, the PAO-acid can be synthesized by converting mPEG-OH into a t-butyl ester. See, for example, commonly assigned U.S. Pat. Nos. 5,605,976 and 5,965,566. The disclosures of each of the foregoing are incorporated by reference herein.

Branched or U-PEG derivatives are described in U.S. Pat. Nos. 5,643,575, 5,919,455, 6,113,906 and 6,566,506, the disclosure of each of which is incorporated herein by reference. A non-limiting list of such polymers corresponds to polymer systems (i)-(vii) with the following structures:

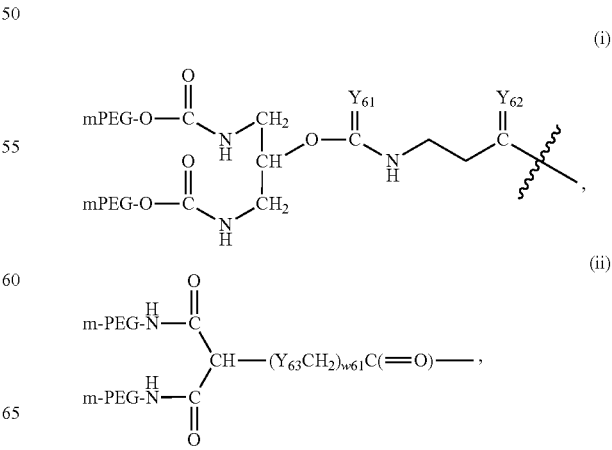

-continued

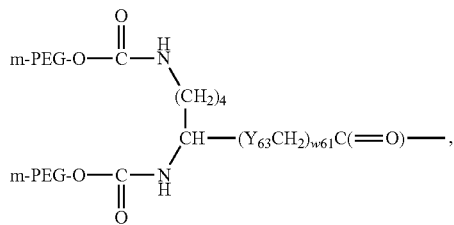
(iii)

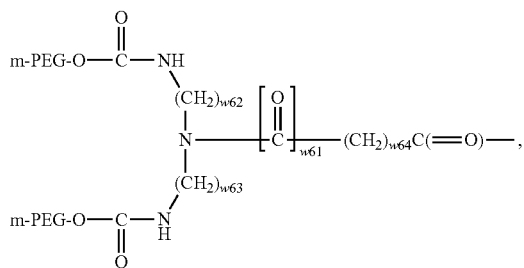
(iv)

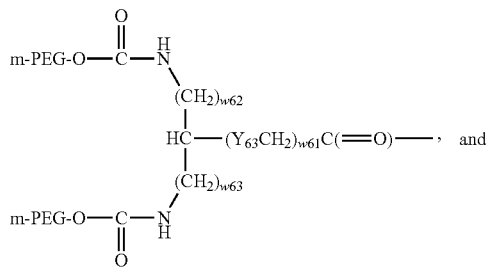
(v)

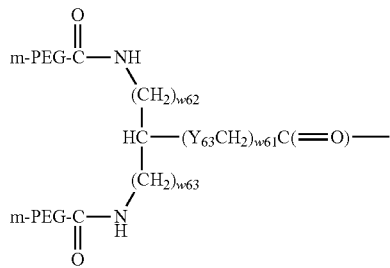
(vi)

wherein:
$Y_{61-62}$ are independently O, S or $NR_{61}$;
$Y_{63}$ is O, $NR_{62}$, S, SO or $SO_2$
(w62), (w63) and (w64) are independently 0 or a positive integer, preferably from about 0 to about 10, more preferably from about 1 to about 6;
(w61) is 0 or 1;
mPEG is methoxy PEG
wherein PEG is previously defined and a total molecular weight of the polymer portion is from about 2,000 to about 100,000 daltons; and
$R_{61}$ and $R_{62}$ are independently selected from among hydrogen, $C_{1-6}$ alkyl, $C_{2-6}$ alkenyl, $C_{2-6}$ alkynyl, $C_{3-19}$ branched alkyl, $C_{3-8}$ cycloalkyl, $C_{1-6}$ substituted alkyl, $C_{2-6}$ substituted alkenyl, $C_{2-6}$ substituted alkynyl, $C_{3-8}$ substituted cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-6}$ substituted alkanoyl, substituted arylcarbonyl, $C_{2-6}$ substituted alkanoyloxy, substituted aryloxycarbonyl, $C_{2-6}$ substituted alkanoyloxy, and substituted and arylcarbonyloxy.

In yet another aspect, the polymers include multi-arm PEG-OH or "star-PEG" products such as those described in NOF Corp. Drug Delivery System catalog, Ver. 8, April 2006, the disclosure of which is incorporated herein by reference. The multi-arm polymer conjugates contain four or more polymer arms and preferably four or eight polymer arms.

For purposes of illustration and not limitation, the multi-arm polyethylene glycol (PEG) residue can be

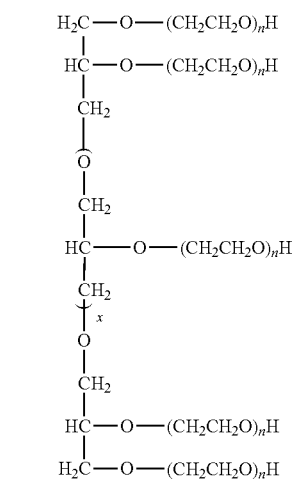

wherein:

(x) is 0 and a positive integer, i.e. from about 0 to about 28; and (n) is the degree of polymerization.

In one particular embodiment of the present invention, the multi-arm PEG has the structure:

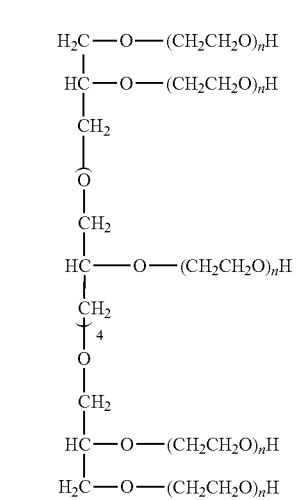

wherein n is a positive integer. In one preferred embodiment of the invention, the polymers have a total molecular weight of from about 5,000 Da to about 60,000 Da, and preferably from 12,000 Da to 40,000 Da.

In yet another particular embodiment, the multi-arm PEG has the structure:

17

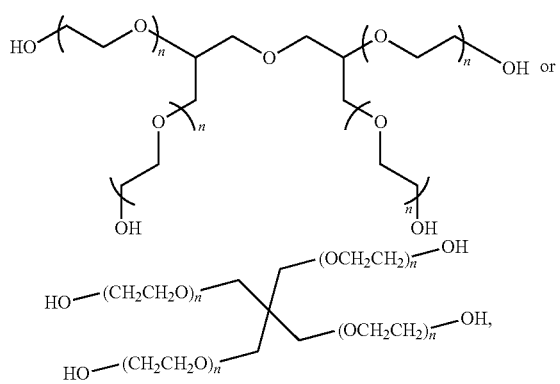

18 wherein n is a positive integer. In one preferred embodiment of the invention, the degree of polymerization for the multi-arm polymer (n) is from about 28 to about 350 to provide polymers having a total molecular weight of from about 5,000 Da to about 60,000 Da, and preferably from about 65 to about 270 (12,000-45,000 daltons) to provide polymers having a total molecular weight of from 12,000 Da to 45,000 Da. This represents the number of repeating units in the polymer chain and is dependent on the molecular weight of the polymer.

The polymers can be converted into a suitably activated polymer, using the activation techniques described in U.S. Pat. Nos. 5,122,614 or 5,808,096. Specifically, such PEG can be of the formula:

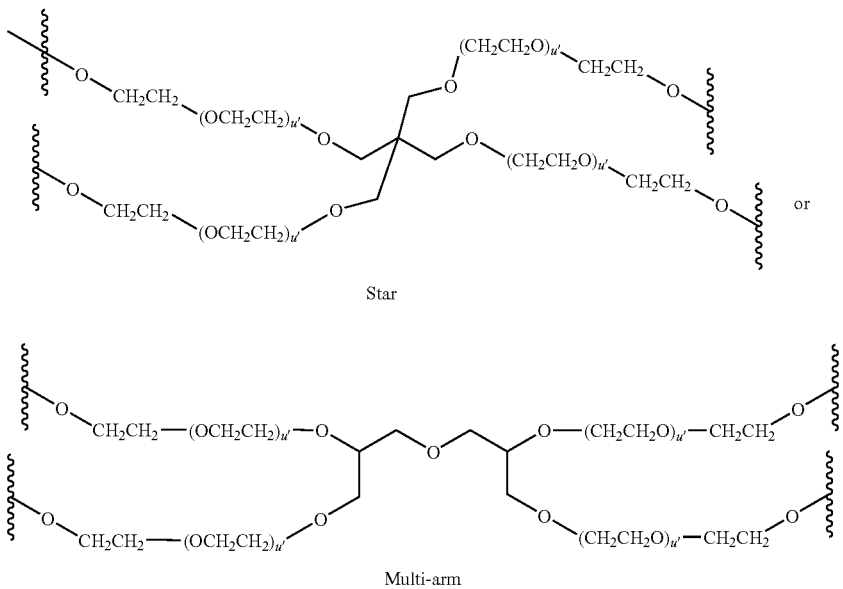

Star

Multi-arm wherein:

(u') is an integer from about 4 to about 455; and up to 3 terminal portions of the residue is/are capped with a methyl or other lower alkyl.

In some preferred embodiments, all four of the PEG arms can be converted to suitable activating groups, for facilitating attachment to aromatic groups. Such compounds prior to conversion include:

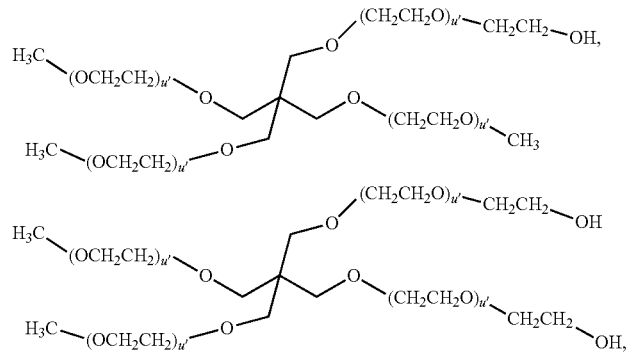

-continued
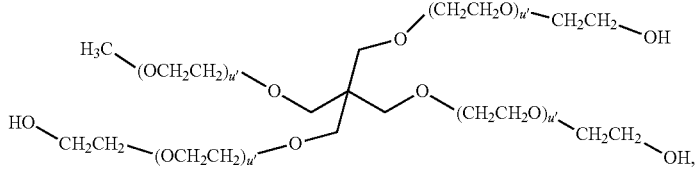
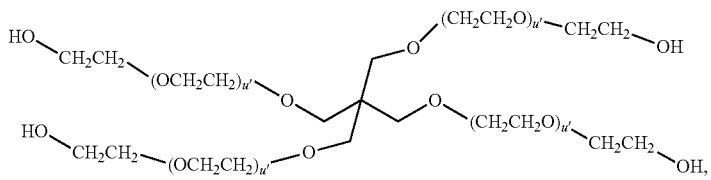
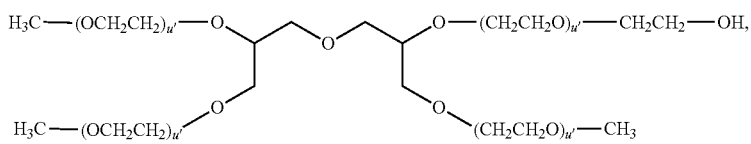
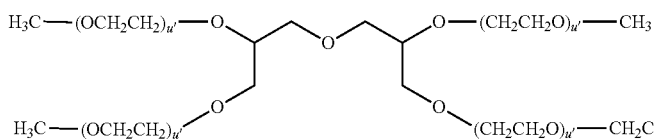
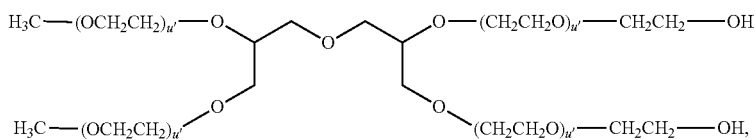
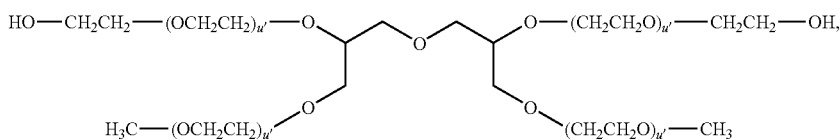
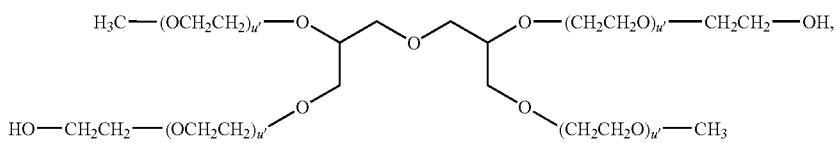
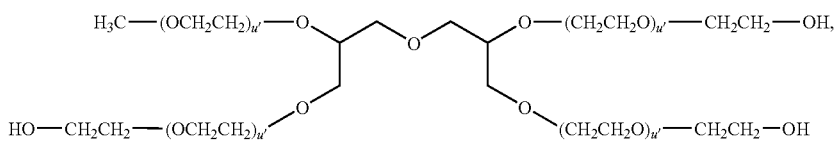
 and
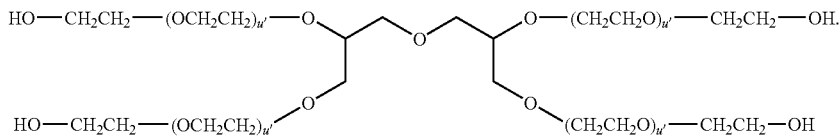

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

In a further embodiment, and as an alternative to PAO-based polymers, one or more effectively non-antigenic materials such as dextran, polyvinyl alcohols, carbohydrate-based polymers, hydroxypropylmethacrylamide (HPMA), polyalkylene oxides, and/or copolymers thereof can be used. See also commonly-assigned U.S. Pat. No. 6,153,655, the contents of which are incorporated herein by reference. It will be understood by those of ordinary skill that the same type of activation is employed as described herein as for PAO's such as PEG. Those of ordinary skill in the art will further realize that the foregoing list is merely illustrative and that all polymeric materials having the qualities described herein are contemplated. For purposes of the present invention, "substantially or effectively non-antigenic" means all materials understood in the art as being nontoxic and not eliciting an appreciable immunogenic response in mammals.

In some aspects, polymers having terminal amine groups can be employed to make the compounds described herein. The methods of preparing polymers containing terminal amines in high purity are described in U.S. patent application Ser. Nos. 11/508,507 and 11/537,172, the contents of each of which are incorporated by reference. For example, polymers having azides react with phosphine-based reducing agent such as triphenylphosphine or an alkali metal borohydride reducing agent such as $NaBH_4$. Alternatively, polymers including leaving groups react with protected amine salts such as potassium salt of methyl-tert-butyl imidodicarbonate (KNMeBoc) or the potassium salt of di-tert-butyl imidodicarbonate ($KNBoc_2$) followed by deprotecting the protected amine group. The purity of the polymers containing the terminal amines formed by these processes is greater than about 95% and preferably greater than 99%.

In alternative aspects, polymers having terminal carboxylic acid groups can be employed in the polymeric delivery systems described herein. Methods of preparing polymers having terminal carboxylic acids in high purity are described in U.S. patent application Ser. No. 11/328,662, the contents of which are incorporated herein by reference. The methods include first preparing a tertiary alkyl ester of a polyalkylene oxide followed by conversion to the carboxylic acid derivative thereof. The first step of the preparation of the PAO carboxylic acids of the process includes forming an intermediate such as t-butyl ester of polyalkylene oxide carboxylic acid. This intermediate is formed by reacting a PAO with a t-butyl haloacetate in the presence of a base such as potassium t-butoxide. Once the t-butyl ester intermediate has been formed, the carboxylic acid derivative of the polyalkylene oxide can be readily provided in purities exceeding 92%, preferably exceeding 97%, more preferably exceeding 99% and most preferably exceeding 99.5% purity.

D. Targeting Agents ($D_1$)

Targeting agents can be attached to the polymeric compounds described herein to guide the conjugates to the target area in vivo. The targeting agents allow biologically active moieties such as pharmaceutically active compounds and oligonucleotides to have therapeutic efficacies at the target area, i.e. tumor site. The targeted delivery in vivo enhances the cellular uptake of these molecules to have better therapeutic efficacies. In certain aspects, some cell penetrating peptides can be replaced with a variety of targeting peptides for targeted delivery to the tumor site.

In one aspect of the invention, the targeting moiety, such as a single chain antibody (SCA) or single-chain antigen-binding antibody, monoclonal antibody, cell adhesion peptides such as RGD peptides and Selectin, cell penetrating peptides (CPPs) such as TAT, Penetratin and $(Arg)_9$, receptor ligands, targeting carbohydrate molecules or lectins, oligonucleotide, oligonucleotide derivatives such as locked nucleic acid (LNA) and aptamers, or the like, allows cytotoxic drugs to be specifically directed to targeted regions. See *Curr Opin Pharmacol*. October 2006;6(5):509-14, Cell-penetrating peptides as vectors for peptide, protein and oligonucleotide delivery; see also *J Pharm Sci*. September 2006;95(9):1856-72 Cell adhesion molecules for targeted drug delivery, the contents of each of which are incorporated herein by reference.

The targeting moieties can be labeled such as biotinylated compounds, fluorescent compounds, radiolabelled compounds. A suitable tag is prepared by linking any suitable moiety, e.g., an amino acid residue, to any art-standard emitting isotope, radio-opaque label, magnetic resonance label, or other non-radioactive isotopic labels suitable for magnetic resonance imaging, fluorescence-type labels, labels exhibiting visible colors and/or capable of fluorescing under ultraviolet, infrared or electrochemical stimulation, to allow for imaging tumor tissue during surgical procedures, and so forth. Optionally, the diagnostic tag is incorporated into and/or linked to a conjugated therapeutic moiety, allowing for monitoring of the distribution of a therapeutic biologically active material within an animal or human patient.

In yet a further aspect of the invention, the inventive tagged conjugates are readily prepared, by art-known methods, with any suitable label, including, e.g., radioisotope labels. Simply by way of example, these include $^{131}$Iodine, $^{125}$Iodine, $^{99m}$Technetium and/or $^{111}$Indium to produce radioimmunoscintigraphic agents for selective uptake into tumor cells, in vivo. For instance, there are a number of art-known methods of linking peptide to Tc-99m, including, simply by way of example, those shown by U.S. Pat. Nos. 5,328,679; 5,888, 474; 5,997,844; and 5,997,845, incorporated by reference herein.

Preferred targeting moieties are single-chain antibodies (SCA's) or single-chain variable fragments of antibodies (sFv). The SCA contains domains of antibodies which can bind or recognize specific molecules of targeting tumor cells. In addition to maintaining an antigen binding site, a PEGylated SCA through linkers can reduce antigenicity and increase the half life of the SCA in the bloodstream.

The terms "single chain antibody" (SCA), "single-chain antigen-binding molecule or antibody" or "single-chain Fv" (sFv) are used interchangeably. The single chain antibody has binding affinity for the antigen. Single chain antibody (SCA) or single-chain Fvs can and have been constructed in several ways. A description of the theory and production of single-chain antigen-binding proteins is found in commonly assigned U.S. patent application Ser. No. 10/915,069 and U.S. Pat. No. 6,824,782, the contents of each of which are incorporated by reference herein.

Typically, SCA or Fv domains can be selected among monoclonal antibodies known by their abbreviations in the literature as 26-10, MOPC 315, 741F8, 520C9, McPC 603, D1.3, murine phOx, human phOx, RFL3.8 sTCR, 1A6, Se155-4,18-2-3,4-4-20,7A4-1, B6.2, CC49,3C2,2c, MA-15C5/$K_{12}G_O$, Ox, etc. (see, Huston, J. S. et al., Proc. Natl. Acad. Sci. USA 85:5879-5883 (1988); Huston, J. S. et al., SIM News 38(4) (Supp):11 (1988); McCartney, J. et al., ICSU Short Reports 10:114 (1990); McCartney, J. E. et al., unpublished results (1990); Nedelman, M. A. et al., J. Nuclear Med. 32 (Supp.):1005 (1991); Huston, J. S. et al., In: Molecular Design and Modeling: Concepts and Applications, Part B, edited by J. J. Langone, Methods in Enzymology 203:46-88 (1991); Huston, J. S. et al., In: Advances in the Applications of Monoclonal Antibodies in Clinical Oncology, Epenetos, A. A. (Ed.), London, Chapman & Hall (1993); Bird, R. E. et al., Science 242:423-426 (1988); Bedzyk, W. D. et al., J. Biol. Chem. 265:18615-18620 (1990); Colcher, D. et al., J. Nat. Cancer Inst. 82:1191-1197 (1990); Gibbs, R. A. et al., Proc. Natl. Acad. Sci. USA 88:4001-4004 (1991); Milenic, D. E. et al., Cancer Research 51:6363-6371 (1991); Pantoliano, M. W. et al., Biochemistry 30:10117-10125 (1991); Chaudhary, V. K. et al., Nature 339:394-397 (1989); Chaudhary, V. K. et al., Proc. Natl. Acad. Sci. USA 87:1066-1070 (1990); Batra, J. K. et al., Biochem. Biophys. Res. Comm. 171:1-6 (1990); Batra, J. K. et al., J. Biol. Chem. 265:15198-15202 (1990); Chaudhary, V. K. et al., Proc. Natl. Acad Sci. USA 87:9491-9494 (1990); Batra, J. K. et al., Mol. Cell. Biol. 11:2200-2205 (1991); Brinkmann, U. et al., Proc. Natl. Acad. Sci. USA 88:8616-8620 (1991); Seetharam, S. et al., J. Biol. Chem. 266:17376-17381 (1991); Brinkmann, U. et al., Proc. Natl. Acad. Sci. USA 89:3075-3079 (1992); Glockshuber, R. et al., Biochemistry 29:1362-1367 (1990); Skerra, A. et al., Bio/Technol. 9:273-278 (1991); Pack, P. et al., Biochemistry 31:1579-1534 (1992); Clackson, T. et al., Nature 352:624-628 (1991); Marks, J. D. et al., J. Mol. Biol. 222:581-597 (1991); Iverson, B. L. et al., Science 249:659-662 (1990); Roberts, V. A. et al., Proc. Natl. Acad. Sci. USA 87:6654-6658 (1990); Condra, J. H. et al., J. Biol. Chem. 265:2292-2295 (1990); Laroche, Y. et al., J. Biol. Chem. 266:16343-16349 (1991); Holvoet, P. et al., J. Biol. Chem. 266:19717-19724 (1991); Anand, N. N. et al., J. Biol. Chem. 266:21874-21879 (1991); Fuchs, P. et al., Biol Technol. 9:1369-1372 (1991); Breitling, F. et al., Gene 104:104-153 (1991); Seehaus, T. et al., Gene 114:235-237 (1992); Takkinen, K. et al., Protein Engng. 4:837-841 (1991); Dreher, M. L. et al., J. Immunol. Methods 139:197-205 (1991); Mottez, E. et al., Eur. J. Immunol. 21:467-471 (1991); Traunecker, A. et al., Proc. Natl. Acad. Sci. USA 88:8646-8650 (1991); Traunecker, A. et al., EMBO J. 10:3655-3659 (1991); Hoo, W. F. S. et al., Proc. Natl. Acad. Sci. USA 89:4759-4763 (1993)). Each of the forgoing publications is incorporated herein by reference.

Alternatively, the targeting moieties can be oligonucleotides or oligonucleotide derivatives. The oligonucleotides (analogs) are not limited to a single species of oligonucleotide but, instead, are designed to work with a wide variety of such moieties, it being understood that linkers can attach to one or more of the 3'- or 5'-terminals, usually $PO_4$ or $SO_4$ groups of a nucleotide. The oligonucleotides include antisense or complementary oligonucleotides, short interfering RNA (siRNA), locked nucleic acid (LNA), micro RNA (miRNA), peptide nucleic acid (PNA), phosphorodiamidate morpholino oligo (PMO) and aptamer, etc.

For example, a non-limiting list of targeting groups includes vascular endothelial cell growth factor, FGF2, somatostatin and somatostatin analogs, transferrin, melanotropin, ApoE and ApoE peptides, von Willebrand's Factor and von Willebrand's Factor peptides, adenoviral fiber protein and adenoviral fiber protein peptides, PD1 and PD1 peptides, EGF and EGF peptides, RGD peptides, folate, etc. Other optional targeting agents appreciated by artisans in the art can be also employed in the compounds described herein.

Preferably, the targeting agents include single chain antibody (SCA), RGD peptides, selectin, TAT, penetratin, Oligo (Arg), preferably $(Arg)_9$, folic acid, etc. For purposes of the present invention, the term "TAT" can be understood to mean a portion of trans-activator of transcription activation protein including a peptide sequence of YGRKKRRQRRR, for example. List of the sequences and structures of peptides used in the specification and examples includes:

C-TAT: (SEQ ID NO: 1)     CYGRKKRRQRRR;

C-(Arg)$_9$: (SEQ ID NO: 2)    CRRRRRRRRR;

RGD can be linear or cyclic:

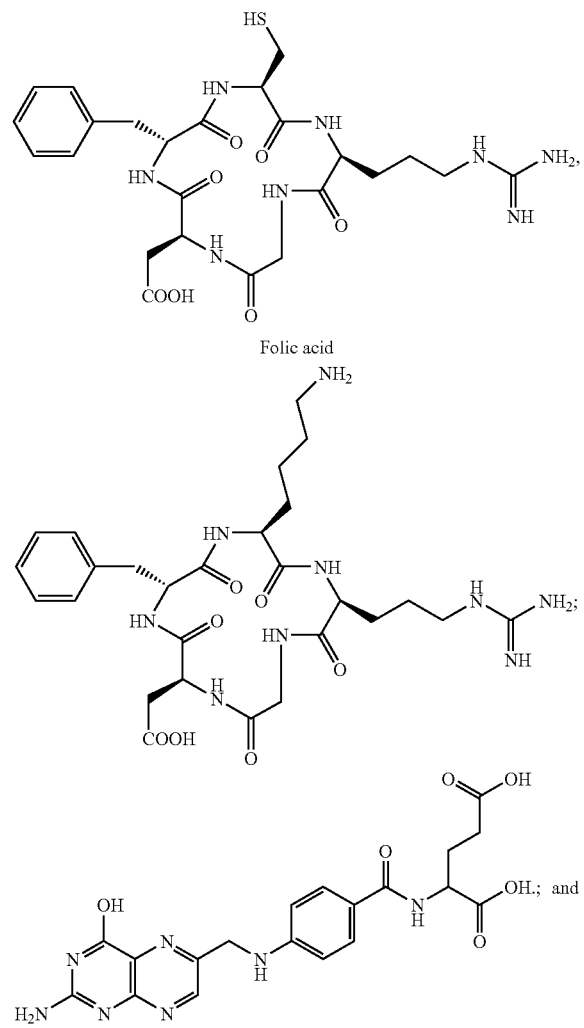

Folic acid $(Arg)_9$ can include a cysteine for conjugating such as CRRRRRRRRR and TAT can add an additional cysteine at the end of the peptide such as CYGRKKRRQRRRC.

E. Biologically Active Moieties ($D_2$)

A wide variety of biologically active moieties can be attached to the activated polymers described herein. The biologically active moieties include pharmaceutically active compounds, enzymes, proteins, oligonucleotides, antibodies, monoclonal antibodies, single chain antibodies and peptides.

Any cytotoxic or chemotherapeutic agent, i.e. folic acid, etc. capable of being attached to a polymer, including but not limited to those biologically active moieties are described in commonly assigned U.S. Pat. No. 5,965,566, the contents of which are incorporated by reference herein.

In one aspect of the invention, the biologically active compounds are suitable for medicinal or diagnostic use in the treatment of animals, e.g., mammals, including humans, for conditions for which such treatment is desired.

In another aspect, amine- hydroxyl- or thiol-containing biologically active moieties are within the scope of the present invention. The only limitations on the types of the biologically active moieties suitable for inclusion herein is that there is available at least one hydroxyl- or thiol-group which can react and link with a carrier portion and that there is not substantial loss of bioactivity in the form of conjugated to the polymeric delivery systems described herein.

Alternatively, parent compounds suitable for incorporation into the polymeric transport conjugate compounds of the invention, may be active after hydrolytic release from the linked compound, or not active after hydrolytic release but which will become active after undergoing a further chemical process/reaction. For example, an anticancer drug that is delivered to the bloodstream by the polymeric transport system, may remain inactive until entering a cancer or tumor cell, whereupon it is activated by the cancer or tumor cell chemistry, e.g., by an enzymatic reaction unique to that cell.

In one preferred embodiment, the polymeric transport systems described herein include pharmaceutically active compounds.

For purposes of the present invention, it shall be understood to mean that the pharmaceutically active compounds include small molecular weight molecules. Typically, the pharmaceutically active compounds have a molecular weight of less than about 1,500 daltons. A non-limiting list of such compounds includes DNA topoisomerase I inhibitors such as camptothecin and analogs, taxanes and paclitaxel derivatives, nucleosides including AZT and acyclovir, anthracycline compounds including daunorubicin and doxorubicin, related antimetabolite compounds including Ara-C (cytosine arabinoside) and gemcitabine, etc.

1. Taxanes and Taxane Derivatives

One class of compounds included in the prodrug compositions of the present invention is taxanes. For purposes of the present invention, the term "taxane" includes all compounds within the taxane family of terpenes. Thus, taxol® (paclitaxel), 3'-substituted tert-butoxy-carbonyl-amine derivatives (taxotere®) and the like as well as other analogs available from, for example, Sigma Chemical of St. Louis, Mo., are within the scope of the present invention.

These compounds have been found to be effective anticancer agents. Numerous studies indicate that the agents have activity against several malignancies. To date, their use has been severely limited by, among other things, their short supply, poor water solubility and hypersensitivity. It is to be understood that other taxanes including the 7-aryl-carbamates and 7-carbazates disclosed in commonly assigned U.S. Pat. Nos. 5,622,986 and 5,547,981 can also be included in the prodrugs of the present invention. The contents of the foregoing U.S. patents are incorporated herein by reference.

Although the examples describe inter alia paclitaxel for illustrative purposes, it is to be understood that the methods described herein are suitable for all taxanes and related molecules.

2. Camptothecin and Related Topoisomerase I Inhibitors

Camptothecin is a water-insoluble cytotoxic alkaloid produced by camptoteca accuminata trees indigenous to China and nothapodytes foetida trees indigenous to India. Camptothecin and related compounds and analogs are also known to be potential anticancer or antitumor agents and have been shown to exhibit these activities in vitro and in vivo. Camptothecin and related compounds are also candidates for conversion to the prodrugs of the present invention. See, for example, U.S. Pat. No. 5,004,758 and Hawkins, *Oncology*, December 1992, pages 17-23. Camptothecin and related analogues are, for example, Topotecan, Irinotecan (CPT-11) or SN38.

Additional camptothecin analogs include those reported in the literature including the 10-hydroxycamptothecins, 11-hydroxycamptothecins and/or 10,11-dihydroxycamptothecins, 7- and/or 9-alkyl, substituted alkyl, cycloalkyl, alkoxy, alkenyl, aminoalkyl, etc. camptothecins, A-ring substituted camptothecins such as 10,11-alkylenedioxycamptothecins, such as those disclosed in U.S. Pat. No. 5,646,159, the contents of which are incorporated herein by reference, etc.

In one preferred embodiment of the invention, the cytotoxic agent is SN38.

3. Oligonucleotides

In order to more fully appreciate the scope of the present invention, the following terms are defined. The artisan will appreciate that the terms, "nucleic acid" or "nucleotide" apply to deoxyribonucleic acid ("DNA"), ribonucleic acid, ("RNA) whether single-stranded or double-stranded, unless otherwise specified, and any chemical modifications thereof. An "oligonucleotide" is generally a relatively short polynucleotide, e.g., ranging in size from about 2 to about 200 nucleotides, or more preferably from about 10 to about 30 nucleotides in length. The oligonucleotides according to the invention are generally synthetic nucleic acids, and are single stranded, unless otherwise specified. The terms, "polynucleotide" and "polynucleic acid" may also be used synonymously herein.

Modifications to the oligonucleotides contemplated in the invention include, for example, the addition to or substitution of selected nucleotides with functional groups or moieties that permit covalent linkage of an oligonucleotide to a desirable polymer, and/or the addition or substitution of functional moieties that incorporate additional charge, polarizability, hydrogen bonding, electrostatic interaction, and functionality to an oligonucleotide. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodouracil, backbone modifications, methylations, base-pairing combinations such as the isobases isocytidine and isoguanidine, and analogous combinations. Oligonucleotide modifications can also include 3' and 5' modifications such as capping. A non-limiting list of nucleoside analogs include:

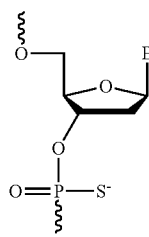

Phosphorthioate

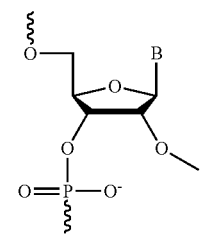

2'-O-Methyl

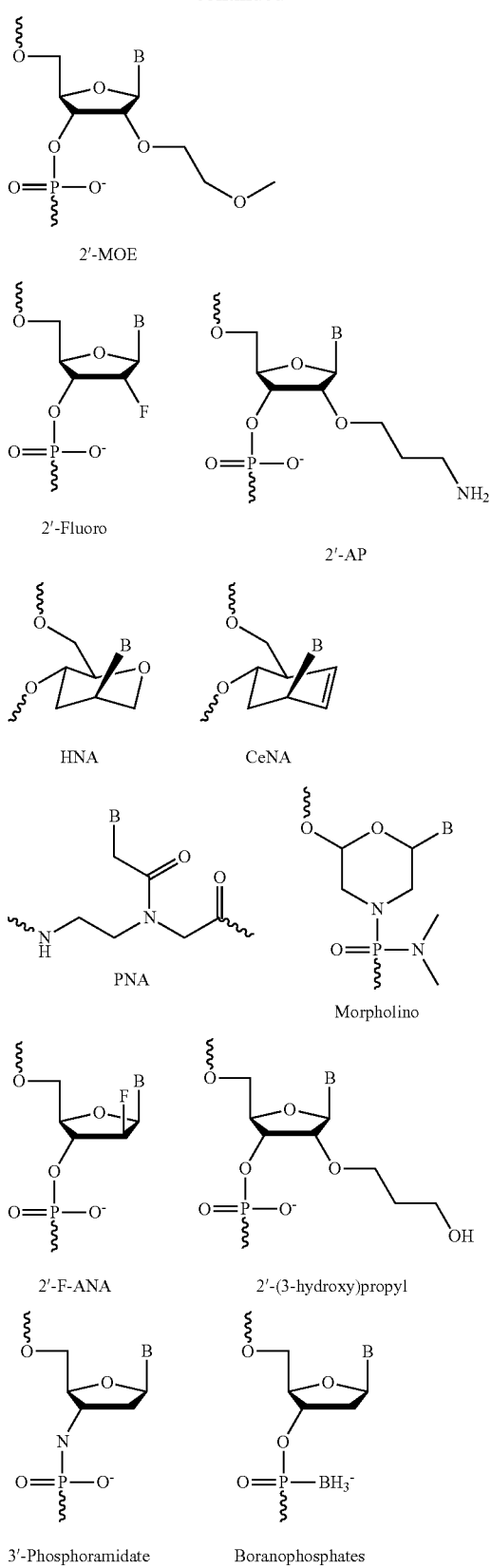

See more examples of nucleoside analogues described in Freier & Altmann; *Nucl. Acid Res.*, 1997, 25, 4429-4443 and Uhlmann; *Curr. Opinion in Drug Development*, 2000, 3(2), 293-213, the contents of each of which are incorporated herein by reference.

The term "antisense," as used herein, refers to nucleotide sequences which are complementary to a specific DNA or RNA sequence that encodes a gene product or that encodes a control sequence. The term "antisense strand" is used in reference to a nucleic acid strand that is complementary to the "sense" strand. In the normal operation of cellular metabolism, the sense strand of a DNA molecule is the strand that encodes polypeptides and/or other gene products. The sense strand serves as a template for synthesis of a messenger RNA ("mRNA") transcript (an antisense strand) which, in turn, directs synthesis of any encoded gene product. Antisense nucleic acid molecules may be produced by any art-known methods, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designations "negative" or (−) are also art-known to refer to the antisense strand, and "positive" or (+) are also art-known to refer to the sense strand In one preferred embodiment, the choice for conjugation is an oligonucleotide (or "polynucleotide") and after conjugation, the target is referred to as a residue of an oligonucleotide. The oligonucleotides can be selected from among any of the known oligonucleotides and oligodeoxynucleotides with phosphorodiester backbones or phosphorothioate backbones.

The oligonucleotides or oligonucleotide derivatives can include from about 10 to about 1000 nucleic acids, and preferably relatively short polynucleotides, e,g., ranging in size from about 2 to about 200 nucleotides, or more preferably from about 10 to about 30 nucleotides in length.

Further, oligonucleotides and oligodeoxynucleotides useful according to the invention include, but are not limited to, the following:

Oligonucleotides and oligodeoxynucleotides with natural phosphorodiester backbone or phosphorothioate backbone or any other modified backbone analogues;

LNA (Locked Nucleic Acid);

PNA (nucleic acid with peptide backbone);

short interfering RNA (siRNA);

microRNA (miRNA);

nucleic acid with peptide backbone (PNA);

phosphorodiamidate morpholino oligonucleotides (PMO);

tricyclo-DNA;

decoy ODN (double stranded oligonucleotide);

catalytic RNA sequence (RNAi);

ribozymes;

aptamers;

spiegelmers (L-conformational oligonucleotides);

CpG oligomers, and the like, such as those disclosed at:

Tides 2002, Oligonucleotide and Peptide Technology Conferences, May 6-8, 2002, Las Vegas, Nev. and Oligonucleotide & Peptide Technologies, 18 & 19 Nov. 2003, Hamburg, Germany, the contents of which are incorporated herein by reference.

Oligonucleotides according to the invention can also optionally include any suitable art-known nucleotide analogs and derivatives, including those listed by Table 1, below:

TABLE 1

Representative Nucleotide Analogs And Derivatives

| | |
|---|---|
| 4-acetylcytidine | 5-methoxyaminomethyl-2-thiouridine |
| 5-(carboxyhydroxymethyl)uridine | beta, D-mannosylqueuosine |
| 2'-O-methylcytidine | 5-methoxycarbonylmethyl-2-thiouridine |
| 5-carboxymethylaminomethyl-2-thiouridine | 5-methoxycarbonylmethyluridine |
| 5-carboxymethylaminomethyluridine | 5-methoxyuridine |
| Dihydrouridine | 2-methylthio-N6-isopentenyladenosine |
| 2'-O-methylpseudouridine | N-((9-beta-D-ribofuranosyl-2-methylthiopurine-6-yl)carbamoyl)threonine |
| D-galactosylqueuosine | N-((9-beta-D-ribofuranosylpurine-6-yl)N-methylcarbamoyl)threonine |
| 2'-O-methylguanosine | uridine-5-oxyacetic acid-methylester |
| Inosine | uridine-5-oxyacetic acid |
| N6-isopentenyladenosine | wybutoxosine |
| 1-methyladenosine | pseudouridine |
| 1-methylpseudouridine | queuosine |
| 1-methylguanosine | 2-thiocytidine |
| 1-methylinosine | 5-methyl-2-thiouridine |
| 2,2-dimethylguanosine | 2-thiouridine |
| 2-methyladenosine | 4-thiouridine |
| 2-methylguanosine | 5-methyluridine |
| 3-methylcytidine | N-((9-beta-D-ribofuranosylpurine-6-yl)-carbamoyl)threonine |
| 5-methylcytidine | 2'-O-methyl-5-methyluridine |
| N6-methyladenosine | 2'-O-methyluridine |
| 7-methylguanosine | wybutosine |
| 5-methylaminomethyluridine | 3-(3-amino-3-carboxy-propyl)uridine |
| Locked-adenosine | Locked-cytidine |
| Locked-guanosine | Locked-thymine |
| Locked-uridine | Locked-methylcytidine |

Preferably, the oligonucleotide is involved in targeted tumor cells or downregulating a protein implicated in the resistance of rumor cells to anticancer therapeutics. For example, any art-known cellular proteins such as BCL-2 for downregulation by antisense oligonucleotides, for cancer therapy, can be used for the present invention. See U.S. patent application Ser. No. 10/822,205 filed Apr. 9, 2004, the contents of which are incorporated by reference herein. A non-limiting list of preferred therapeutic oligonucleotides include antisense HIF-1a oligonucleotides and antisense Survivin oligonucleotides.

In one preferred embodiment, the oligonucleotide can be, for example, an oligonucleotide that has the same or substantially similar nucleotide sequence as does Genasense (a/k/a oblimersen sodium, produced by Genta Inc., Berkeley Heights, N.J.). Genasense is an 18-mer phosphorothioate antisense oligonucleotide, TCTCCCAGCGTGCGCCAT (SEQ ID NO: 6), that is complementary to the first six codons of the initiating sequence of the human bcl-2 mRNA (human bcl-2 mRNA is art-known, and is described, e.g., as SEQ ID NO: 19 in U.S. Pat. No. 6,414,134, incorporated by reference herein). The U.S. Food and Drug Administration (FDA) gave Genasense Orphan Drug status in August 2000. Preferred embodiments include:

(i) antisense Survivin LNA (SEQ ID NO: 3)
$^mC_s$-$T_s$-$^mC_s$-$A_s$-$a_s$-$t_s$-$c_s$-$c_s$-$a_s$-$t_s$-$g_s$-$g_s$-$^mC_s$-$A_s$-$G_s$-c;

where the upper case letter represents LNA, the "s" represents a phosphorothioate backbone;

(ii) antisense Bcl2 siRNA:

```
SENSE
5'-GCAUGCGGCCUCUGUUUGAdTdT-3'    (SEQ ID NO: 4)

ANTISENSE
3'-dTdTCGUACGCCGGAGACAAACU-5'    (SEQ ID NO: 5)
``` where dT represents DNA;

(iii) Genasense (phosphorothioate antisense oligonucleotide):

(SEQ ID NO: 6)
$t_s$-$c_s$-$t_s$-$c_s$-$c_s$-$c_s$-$a_s$-$g_s$-$c_s$-$g_s$-$t_s$-$g_s$-$c_s$-$g_s$-$c_s$-$c_s$-$c_s$-$a_s$-t where the lower case letter represents DNA and and "s" represents phosphorothioate backbone;

(iv) antisense HIF1α LNA (SEQ ID: 7)

(SEQ ID NO: 7)
5'-$_s$T$_s$G$_s$G$_s$c$_s$a$_s$a$_s$g$_s$c$_s$a$_s$t$_s$c$_s$c$_s$T$_s$G$_s$T$_s$a-3' where the upper case letter represents LNA and the "s" represents phosphorothioate backbone.

LNA includes 2'-O, 4'-C methylene bicyclonucleotide as shown below:

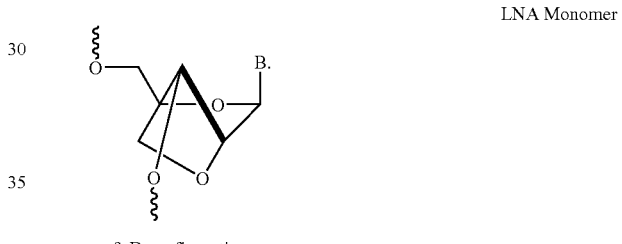

LNA Monomer

β-D configuration

See detailed description of Survivin LNA disclosed in U.S. patent application Ser. No. 11/272,124, entitled "LNA Oligonucleotides and the Treatment of Cancer" and U.S. Ser. No. 10/776,934, entitled "Oligomeric Compounds for the Modulation Survivin Expression", the contents of each of which is incorporated herein by reference. See also U.S. patent application Ser. No. 10/407,807, entitled "Oligomeric Compounds for the Modulation HIF-1 Alpha Expression" and U.S. Ser. No. 11/271,686, entitled "Potent LNA Oligonucleotides for Inhibition of HIF-1A Expression", the contents of which are also incorporated herein by reference.

The oligonucleotides employed in the compounds described herein can be modified with $(CH_2)_w$ amino linkers at 5' or 3' end of the oligonucleotides, where w in this aspect is a positive integer of preferably from about 1 to about 10, preferably 6. The modified oligonucleotides contemplated in the compounds described herein can be NH—$(CH_2)_w$-Oligonucleotide.

In one preferred embodiment, 5' end of the sense strand of siRNA is modified. For example, siRNA employed in the polymeric conjugates is modified with a 5'-$C_6$—$NH_2$. One particular embodiment of the present invention employs Bcl2-siRNA having the sequence of

```
SENSE       5'-(NH_2-C_6)GCAUGCGGCCUCUGUUUGAdTdT-3'

ANTISENSE   3'-dTdTCGUACGCCGGAGACAAACU-5'.
```

In another preferred embodiment, the compounds described herein can include oligonucleotides modified with hindered ester-containing $(CH_2)_w$ amino linkers. See U.S. Provisional Application No. 60/844,942 entitled "Polyalkylene Oxides Having Hindered Ester-Based Biodegradable Linkers", the contents of which are incorporated by reference. The polymeric compounds can release the oligonucleotides without amino tail. For example, the oligonucleotides can have the structure:

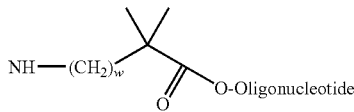

wherein w is a positive integer from about 1 to about 10, preferably about 6.

In yet another preferred embodiment, oligonucleotides can be modified with $(CH_2)_w$ sulfhydryl linkers (thio oligonucleotides). The thio oligonucletides can be used for conjugating directly to cysteine of the positively charge peptide or via maleimidyl group. The thio oligonucleotides can have the structure SH—$(CH_2)_w$-Oligonucleotide. The thio oligonucleotides can also include hindered ester having the structure:

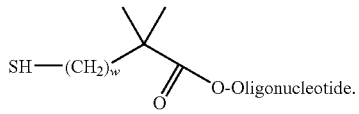

Exemplenary of the modified oligonucleotides include:
(i) Genasense modified with a $C_6$—$NH_2$ tail:

5'-$NH_2$—$C_6$-$_st_sc_st_sc_sc_sc_sa_sg_sc_sg_st_sg_sc_sg_sc_sc_sa_st$-3'

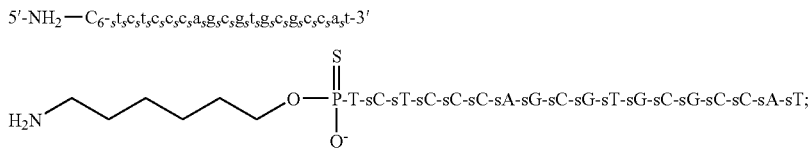

(ii) antisense HIF1a LNA modified with a $C_6$—$NH_2$ tail:
5'-$NH_2$—$C_6$-$_sT_sG_sG_sc_sa_sa_sg_sc_sa_st_sc_sc_sT_sG_sT_s$a-3';
(iii) antisense Survivin LNA modified with a $C_6$—$NH_2$ tail:
5'-$NH_2$—$C_6$—$_s^mC_sT_s^mC_sA_sa_st_sc_sc_sa_st_sg_sg_s^mC_sA_sG_sc$-3';
(iv) antisense Survivin LNA modified with a $C_6$—SH tail
5'-HS—$C_6$—$_s^mC_sT_s^mC_sA_sa_st_sc_sc_sa_st_sg_sg_s^mC_sA_sG_sc$-3';
(v) Genasense modified with a hindered ester tail

4. Additional Biologically-Active Moieties

In addition to the foregoing molecules, the compounds of the present invention can be prepared using many other compounds. For example, biologically-active compounds such as cis-platin derivatives containing OH groups, floxuridine, podophyllotoxin, and related compounds can be included.

Other useful parent compounds include, for example, certain low molecular weight biologically active proteins, enzymes and peptides, including peptido glycans, as well as other anti-tumor agents, cardiovascular agents such as for-skolin, anti-neoplastics such as combretastatin, vinblastine, vincristine, doxorubicin, AraC, maytansine, etc. anti-infectives such as vancomycin, etc. anti-fungals such as nystatin or amphoteracin B, anti-inflammatory agents, steroidal agents, and the like.

The foregoing is illustrative of the biologically active moieties which are suitable for the prodrugs of the present invention.

F. Permanent and Releasable Linkers: ($L_1$ and $L_3$)

The $L_1$ and $L_3$ linkers include bifunctional linkers. The bifunctional can be permanent or releasable linkers. The bifunctional linkers include amino acids or amino acid derivatives. The amino acids can be among naturally occurring and non-naturally occurring amino acids. Derivatives and analogs of the naturally occurring amino acids, as well as various art-known non-naturally occurring amino acids (D or L), hydrophobic or non-hydrophobic, are also contemplated to be within the scope of the invention. A suitable non-limiting list of the non-naturally occurring amino acids includes 2-aminoadipic acid, 3-aminoadipic acid, beta-alanine, beta-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4-aminobutyric acid, desmosine, 2,2-diaminopimelic acid, 2,3-diaminopropionic acid, N-ethylglycine, N-ethylasparagine, 3-hydroxyproline, 4-hydroxyproline, isodesmosine, allo-isoleucine, N-methylglycine, sarcosine, N-methyl-isoleucine, 6-N-methyl-lysine, N-methylvaline, norvaline, norleucine, and ornithine. Some preferred amino acid residues are selected from glycine, alanine, methionine and sarcosine, and more preferably, glycine.

Alternatively, The $L_1$ and $L_3$ can be selected from among:

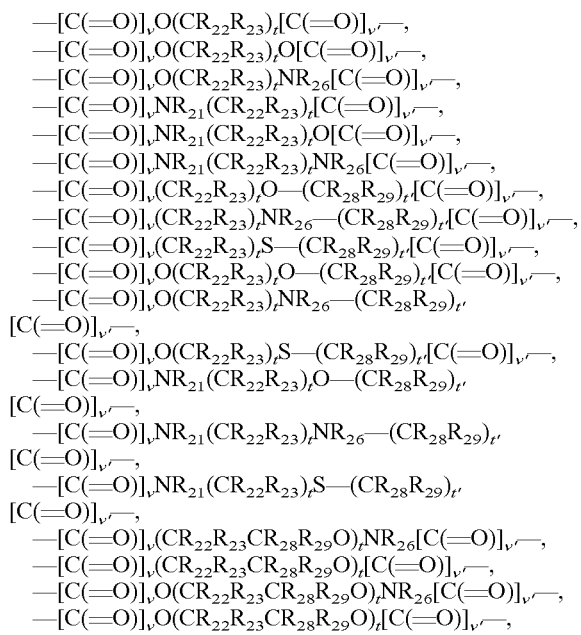

—[C(=O)]$_v$NR$_{21}$(CR$_{22}$R$_{23}$CR$_{28}$R$_{29}$O)$_t$NR$_{26}$[C(=O)]$_{v'}$—,
—[C(=O)]$_v$NR$_{21}$(CR$_{22}$R$_{23}$CR$_{28}$R$_{29}$O)$_t$[C(=O)]$_{v'}$—,
—[C(=O)]$_v$(CR$_{22}$R$_{23}$CR$_{28}$R$_{29}$O)$_t$(CR$_{24}$R$_{25}$)$_{t'}$[C(=O)]$_{v'}$—,
—[C(=O)]$_v$O(CR$_{22}$R$_{23}$CR$_{28}$R$_{29}$O)$_t$(CR$_{24}$R$_{25}$)$_{t'}$[C(=O)]$_{v'}$—,
—[C(=O)]$_v$NR$_{21}$(CR$_{22}$R$_{23}$CR$_{28}$R$_{29}$O)$_t$(CR$_{24}$R$_{25}$)$_{t'}$[C(=O)]$_{v'}$—,
—[C(=O)]$_v$(CR$_{22}$R$_{23}$CR$_{28}$R$_{29}$O)$_t$(CR$_{24}$R$_{25}$)$_t$O[C(=O)]$_{v'}$—,
—[C(=O)]$_v$(CR$_{22}$R$_{23}$)$_t$(CR$_{24}$R$_{25}$CR$_{28}$R$_{29}$O)$_{t'}$[C(=O)]$_{v'}$—,
—[C(=O)]$_v$(CR$_{22}$R$_{23}$)$_t$(CR$_{24}$R$_{25}$CR$_{28}$R$_{29}$O)$_t$NR$_{26}$[C(=O)]$_{v'}$—,
—[C(=O)]$_v$O(CR$_{22}$R$_{23}$CR$_{28}$R$_{29}$O)$_t$(CR$_{24}$R$_{25}$)$_t$O[C(=O)]$_{v'}$—,
—[C(=O)]$_v$O(CR$_{22}$R$_{23}$)$_t$(CR$_{24}$R$_{25}$CR$_{28}$R$_{29}$O)$_{t'}$[C(=O)]$_{v'}$—,
—[C(=O)]$_v$O(CR$_{22}$R$_{23}$)$_t$(CR$_{24}$CR$_{25}$CR$_{28}$R$_{29}$O)$_t$NR$_{26}$[C(=O)]$_{v'}$—,
—[C(=O)]$_v$NR$_{21}$(CR$_{22}$R$_{23}$CR$_{28}$R$_{29}$O)$_t$(CR$_{24}$R$_{25}$)$_t$O[C(=O)]$_{v'}$—,
—[C(=O)]$_v$NR$_{21}$(CR$_{22}$R$_{23}$)$_t$(CR$_{24}$R$_{25}$CR$_{28}$R$_{29}$O)$_{t'}$[C(=O)]$_{v'}$—,
—[C(=O)]$_v$NR$_{21}$(CR$_{22}$R$_{23}$)$_t$(CR$_{24}$R$_{25}$CR$_{28}$R$_{29}$O)$_t$NR$_{26}$[C(=O)]$_{v'}$—,

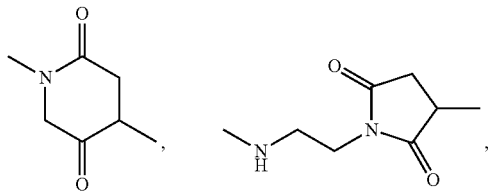

—[C(=O)]$_v$O(CR$_{22}$R$_{23}$)$_t$—⟨R$_{27}$ phenyl⟩—(CR$_{24}$R$_{25}$)$_{t'}$NR$_{26}$[C(=O)]$_{v'}$—, —[C(=O)]$_v$O(CR$_{22}$R$_{23}$)$_t$—⟨R$_{27}$ phenyl⟩—(CR$_{24}$R$_{25}$)$_{t'}$O[C(=O)]$_{v'}$—, —[C(=O)]$_v$NR$_{21}$(CR$_{22}$R$_{23}$)$_t$—⟨R$_{27}$ phenyl⟩—(CR$_{24}$R$_{25}$)$_{t'}$NR$_{26}$[C(=O)]$_{v'}$— and

—[C(=O)]$_v$NR$_{21}$(CR$_{22}$R$_{23}$)$_t$—⟨R$_{27}$ phenyl⟩—(CR$_{24}$R$_{25}$)$_{t'}$O[C(=O)]$_{v'}$—, wherein:
R$_{21-29}$ are independently selected from among hydrogen, C$_{1-6}$ alkyls, C$_{3-12}$ branched alkyls, C$_{3-8}$ cycloalkyls, C$_{1-6}$ substituted alkyls, C$_{3-8}$ substituted cyloalkyls, aryls, substituted aryls, aralkyls, C$_{1-6}$ heteroalkyls, substituted C$_{1-6}$ heteroalkyls, C$_{1-6}$ alkoxy, phenoxy and C$_{1-6}$ heteroalkoxy;

(t) and (t') are independently zero or a positive integer, preferably zero or an integer from about 1 to about 12, more preferably an integer from about 1 to about 8, and most preferably 1 or 2; and (v) and (v') are independently zero or 1.

Preferably, the bifunctional linkers can be selected from among:
—[C(=O)]$_r$NH(CH$_2$)$_2$CH=N—NHC(=O)—(CH$_2$)$_2$—,
—[C(=O)]$_r$NH(CH$_2$)$_2$(CH$_2$CH$_2$O)$_2$(CH$_2$)$_2$NH[C(=O)]$_{r'}$—,
—[C(=O)]$_r$NH(CH$_2$CH$_2$)(CH$_2$CH$_2$O)$_2$NH[C(=O)]$_{r'}$—,
—[C(=O)]$_r$NH(CH$_2$CH$_2$)$_s$NH(CH$_2$CH$_2$)$_s$[C(=O)]$_{r'}$—,
—[C(=O)]$_r$NH(CH$_2$CH$_2$)$_s$S(CH$_2$CH$_2$)$_s$[C(=O)]$_{r'}$—,
—[C(=O)]$_r$NH(CH$_2$CH$_2$)(CH$_2$CH$_2$O)[C(=O)]$_{r'}$—,
—[C(=O)]$_r$NH(CH$_2$CH$_2$)$_s$O(CH$_2$CH$_2$)$_s$[C(=O)]$_{r'}$—,
—[C(=O)]$_r$NH(CH$_2$CH$_2$O)(CH$_2$)NH[C(=O)]$_{r'}$—,
—[C(=O)]$_r$NH(CH$_2$CH$_2$O)$_2$(CH$_2$)[C(=O)]$_{r'}$—,
—[C(=O)]$_r$NH(CH$_2$CH$_2$O)$_s$(CH$_2$)$_s$[C(=O)]$_{r'}$—,
—[C(=O)]$_r$NHCH$_2$CH$_2$NH[C(=O)]$_{r'}$—,
—[C(=O)]$_r$NH(CH$_2$CH$_2$)$_2$O[C(=O)]$_{r'}$—,
—[C(=O)]$_r$NH(CH$_2$CH$_2$O)[C(=O)]$_{r'}$—,
—[C(=O)]$_r$NH(CH$_2$CH$_2$O)$_2$[C(=O)]$_{r'}$—,
—[C(=O)]$_r$NH(CH$_2$)$_3$[C(=O)]$_{r'}$—,
—[C(=O)]$_r$O(CH$_2$CH$_2$O)$_2$(CH$_2$)[C(=O)]$_{r'}$—,
—[C(=O)]$_r$O(CH$_2$)$_2$NH(CH$_2$)$_2$[C(=O)]$_{r'}$—,
—[C(=O)]$_r$O(CH$_2$CH$_2$O)$_2$NH[C(=O)]$_{r'}$—,
—[C(=O)]$_r$O(CH$_2$)$_2$O(CH$_2$)$_2$[C(=O)]$_{r'}$—,
—[C(=O)]$_r$O(CH$_2$)$_2$S(CH$_2$)$_2$[C(=O)]$_{r'}$—,
—[C(=O)]$_r$O(CH$_2$CH$_2$)NH[C(=O)]$_{r'}$—,
—[C(=O)]$_r$O(CH$_2$CH$_2$)O[C(=O)]$_{r'}$—,
—[C(=O)]$_r$O(CH$_2$)$_3$NH[C(=O)]$_{r'}$—,
—[C(=O)]$_r$O(CH$_2$)$_3$O[C(=O)]$_{r'}$—,
—[C(=O)]$_r$O(CH$_2$)$_3$[C(=O)]$_{r'}$—,
—[C(=O)]$_r$CH$_2$NHCH$_2$[C(=O)]$_{r'}$—,
—[C(=O)]$_r$CH$_2$OCH$_2$[C(=O)]$_{r'}$—,
—[C(=O)]$_r$CH$_2$SCH$_2$[C(=O)]$_{r'}$—,
—[C(=O)]$_r$S(CH$_2$)$_3$[C(=O)]$_{r'}$—,
—[C(=O)]$_r$(CH$_2$)$_3$[C(=O)]$_{r'}$—,

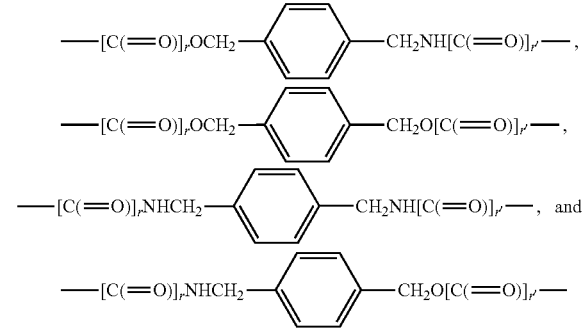

wherein (r) and (r') are independently zero or 1, provided that both (r) and (r') are not simultaneously zero.

1. Releasable Linkers

In one preferred embodiment of the invention, the compounds described herein contain a biologically active moiety attached to a releasable linker. One advantage of the invention is that the biologically active moiety can be released in a controlled manner.

Among the releasable linkers can be benzyl elimination-based linkers, trialkyl lock-based linkers (or trialkyl lock lactonization based), bicine-based linkers, acid labile linkers, lysosomally cleavable peptides and capthepsin B cleavable peptides. Among the acid labile linkers can be disulfide bond, hydrazone-containing linkers and thiopropionate-containing linkers.

Alternatively, the releasable linkers are intracellular labile linkers, extracellular linkers and acidic labile linkers. The acidic labile linkers, such as hydrazone linkages, can be hydrolyzed in the acidic lysosome environment. Some suitable releasable linkers are oligopeptides including such as Val-Cit, Ala-Leu-Ala-Leu, Gly-Phe-Leu-Gly and Phe-Lys. One preferred releasable linker is a peptidyl linker (Val-Cit) which can be specifically degraded by capthesin B. Preferably, the L$_3$ include releasable linker.

The preferred releasable linkers include:

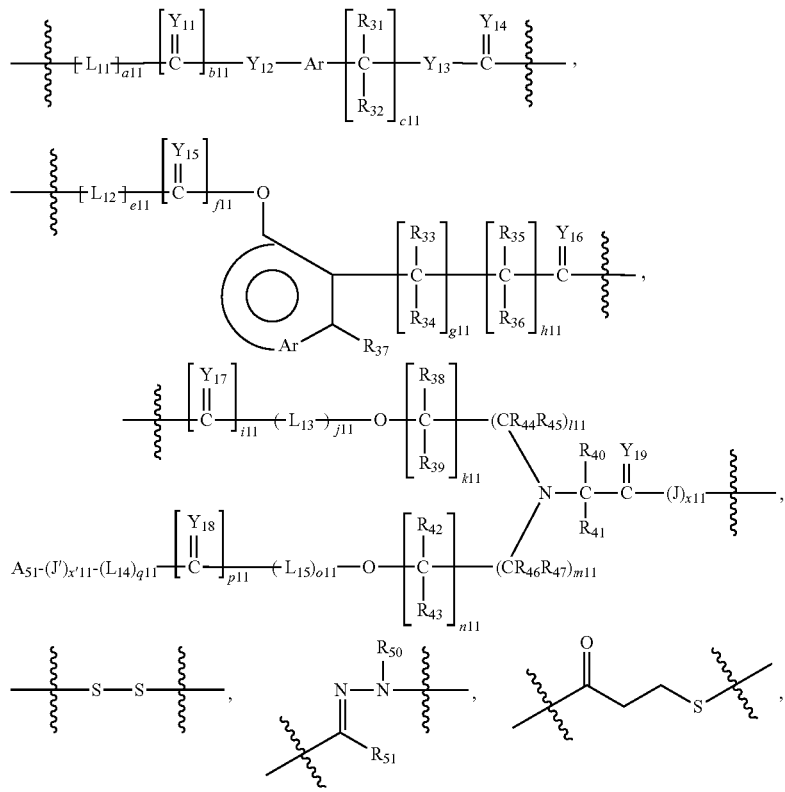

-Val-Cit-,
-Gly-Phe-Leu-Gly-,
-Ala-Leu-Ala-Leu-,
-Phe-Lys-,

-Val-Cit-C(=O)—CH$_2$OCH$_2$—C(=O)—,
-Val-Cit-C(=O)—CH$_2$SCH$_2$—C(=O)—, and
—NHCH(CH$_3$)—C(=O)—NH(CH$_2$)$_6$—C(CH$_3$)$_2$—C(=O)— wherein, $Y_{11-19}$ are independently O, S or $NR_{48}$;

$R_{31-48}$, $R_{50-51}$ and $A_{51}$ are independently selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cyloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

Ar is an aryl or heteroaryl moiety;

$L_{11-15}$ are independently selected bifunctional spacers;

J and J' are independently selected from selected from among moieties actively transported into a target cell, hydrophobic moieties, bifunctional linking moieties and combinations thereof;

(c11), (h11), (k11), (l11), (m11) and (n11) are independently selected positive integers, preferably 1;

(a11), (e11), (g11), (j11), (o11) and (q11) are independently either zero or a positive integers, preferably 1; and (b11), (x11), (x'11), (f11), (i11) and (p11) are independently zero or one.

Various releasable linkers, benzyl elimination based or trialkyl lock based, are described, for example, in commonly assigned U.S. Pat. Nos. 6,180,095, 6,720,306, 5,965,119, 6,624,142 and 6,303,569, the contents of each of which are incorporated herein by reference. The bicine-based linkers are also described in commonly assigned U.S. Pat. Nos. 7,122,189 and 7,087,229 and U.S. patent application Ser. Nos. 10/557,522, 11/502,108, and 11/011,818, the contents of each of which are incorporated herein by reference.

Preferably, the biologically active compounds including oligonucleotides are linked to the polymeric portion of the compounds described herein via acid labile linkers. Without being bound by any theory, the acid labile linkers facilitate release of the oligonucleotides from the parent polymeric compounds within cells and specifically in lysosome, endosome, or macropinosome.

2. Permanent Linkers

In preferred aspects of the invention, the targeting moiety such as the SCA is attached to the multifunctional linker through a permanent linker. The permanent linkers are capable of conjugating the targeting moiety and the multifunctional linker. One preferred permanent linker can be a molecule like a maleimidyl-containing molecule which can provide a thio-ether bond.

The permanent linkers containing maleimidyl groups can be selected from among:

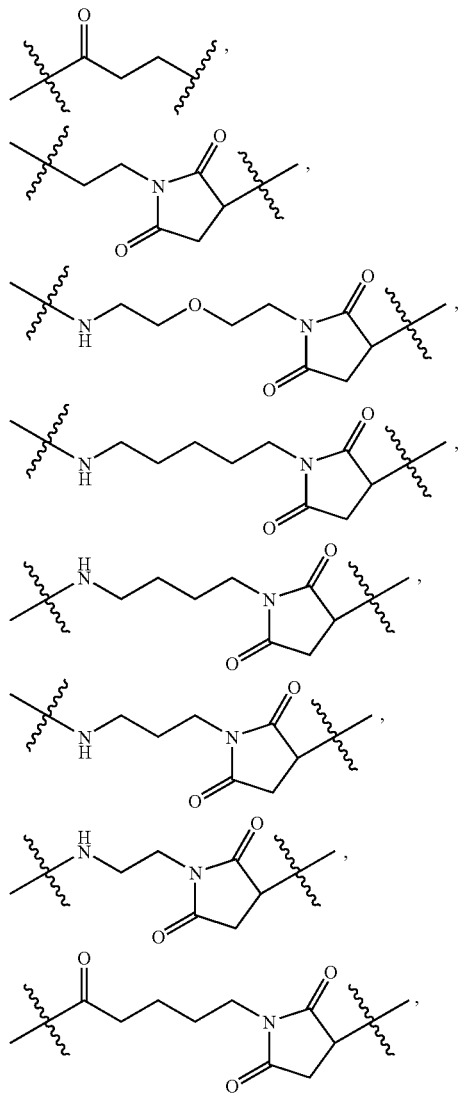

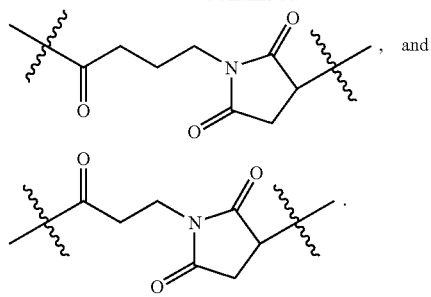

In an alternative embodiment, the permanent linkers include structures corresponding to those shown above but instead of maleimidyl group have groups such as vinyl, residues of sulfone, amino, carboxy, mercapto, hydrazide, carbamate and the like instead of maleimidyl.

G. Leaving Groups and Functional Groups

In some aspects, suitable leaving groups include, without limitations, halogen (Br, Cl), activated carbonate, carbonyl imidazole, cyclic imide thione, isocyanate, N-hydroxysuccinimidyl, para-nitrophenoxy, N-hydroxyphtalimide, N-hydroxybenzotriazolyl, imidazole, tosylate, mesylate, tresylate, nosylate, $C_1$-$C_6$ alkyloxy, $C_1$-$C_6$ alkanoyloxy, arylcarbonyloxy, ortho-nitrophenoxy, N-hydroxybenzotriazolyl, imidazole, pentafluorophenoxy, 1,3,5-trichlorophenoxy, and 1,3,5-trifluorophenoxy or other suitable leaving groups as will be apparent to those of ordinary skill.

For purposes of the present invention, leaving groups are to be understood as those groups which are capable of reacting with a nucleophile found on the desired target, i.e. a biologically active moiety and a targeting moiety.

In some preferred embodiments, functional groups to link the polymeric transport systems to biologically active moieties include maleimidyl, vinyl, residues of sulfone, amino, carboxy, mercapto, hydrazide, carbazate and the like which can be further conjugated to a biologically active group or a targeting group.

For purposes of the present invention, when the $D_1$ or $D_2$ are functional groups, the $L_1$ and $L_3$ groups are not functional moieties.

In one preferred embodiment, the functional group can be maleimidyl and the leaving groups can be selected from among OH, methoxy, tert-butoxy, para-nitrophenoxy and N-hydroxysuccinimidyl.

H. Preferred Embodiments Corresponding to Formula (I)

Some particular embodiments prepared by the methods described herein include:

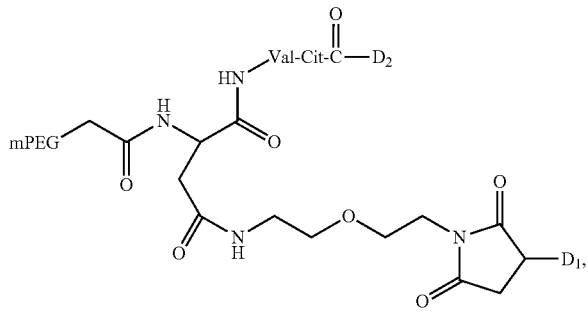

-continued
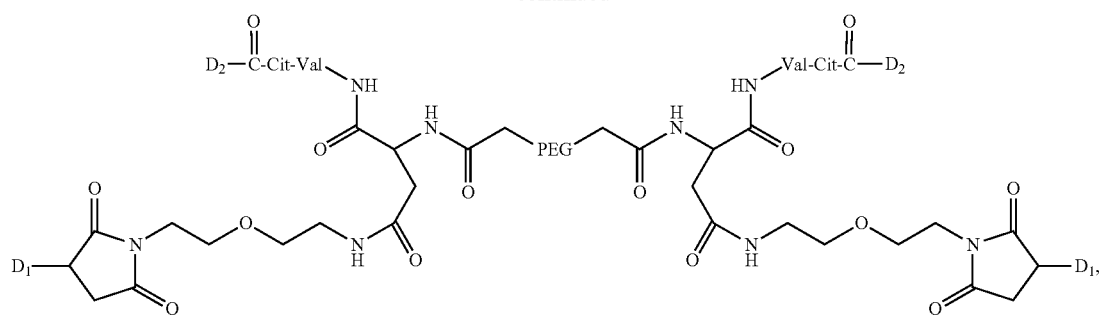
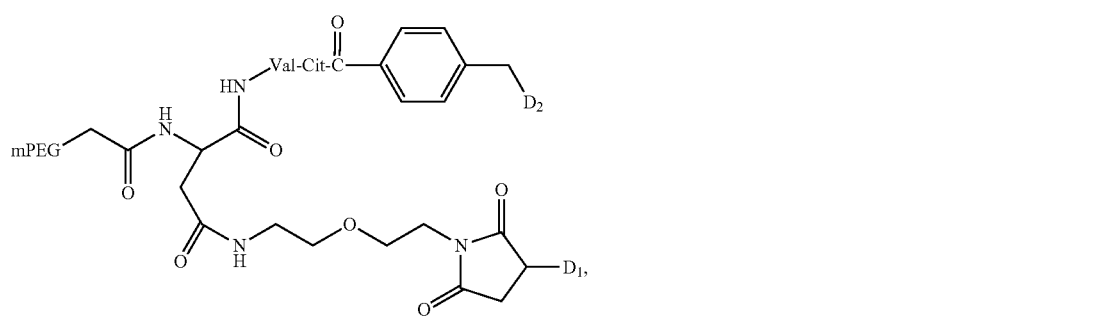
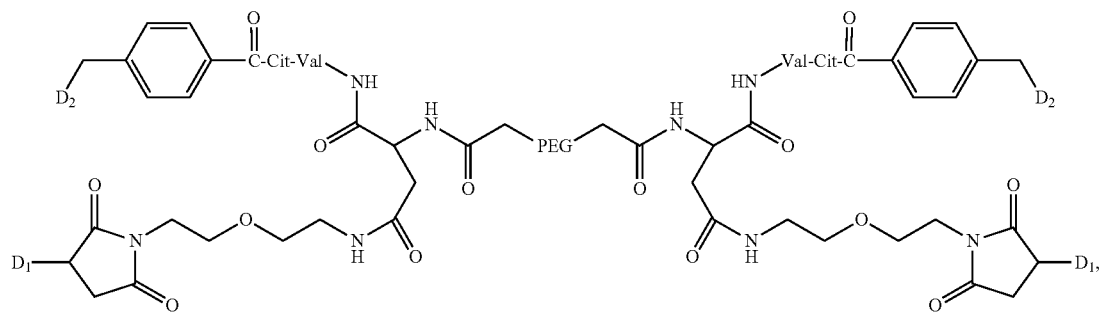
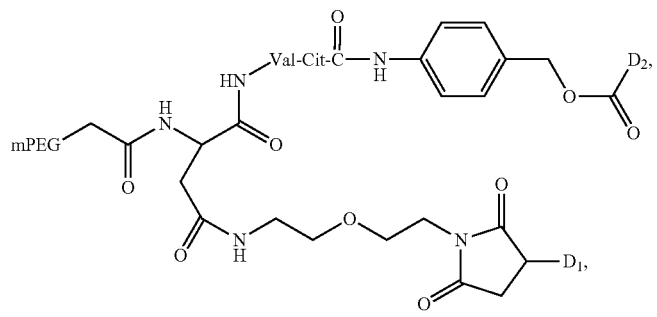
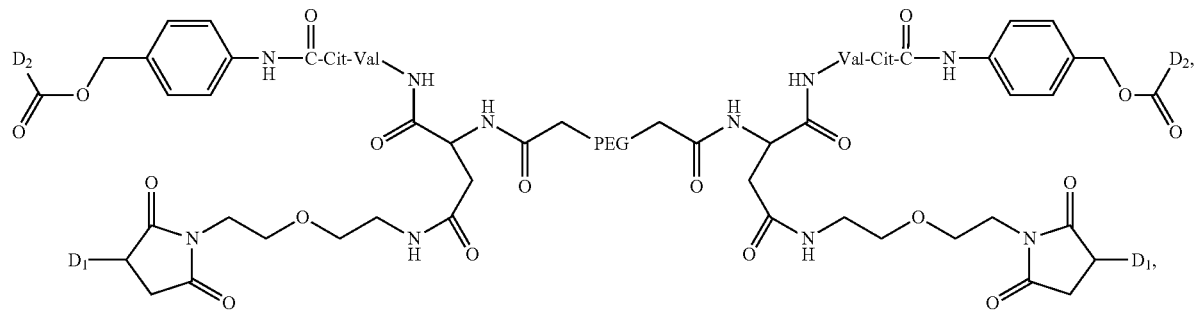

-continued
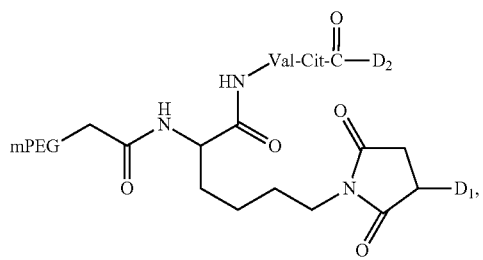
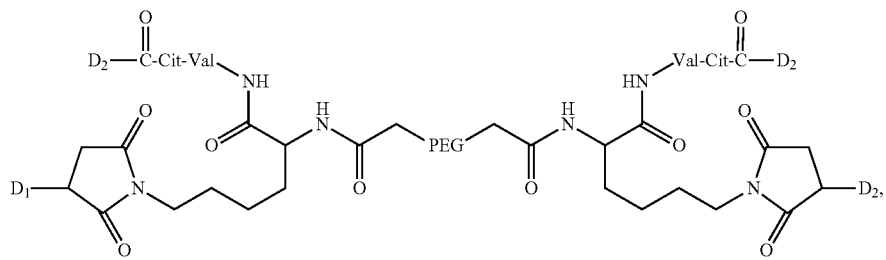
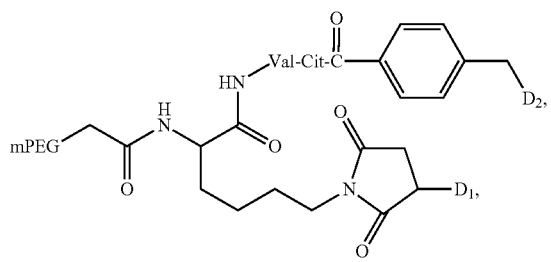
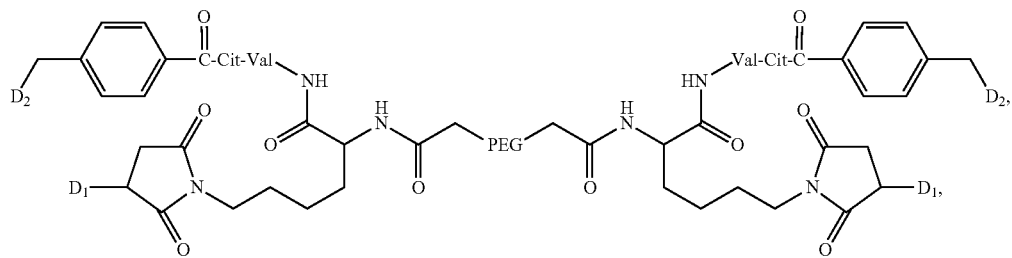
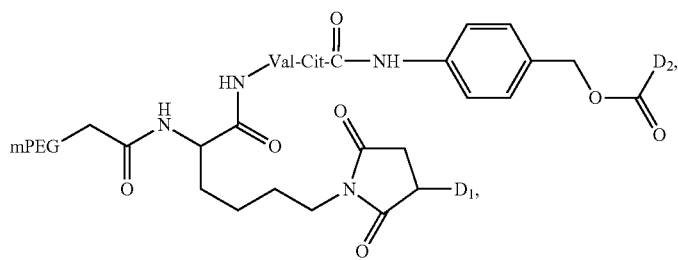
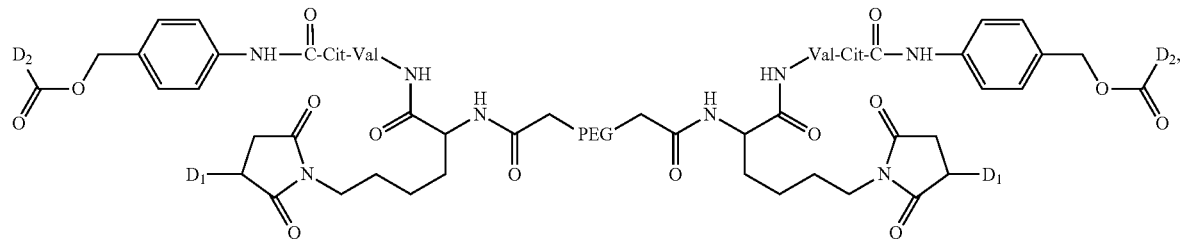

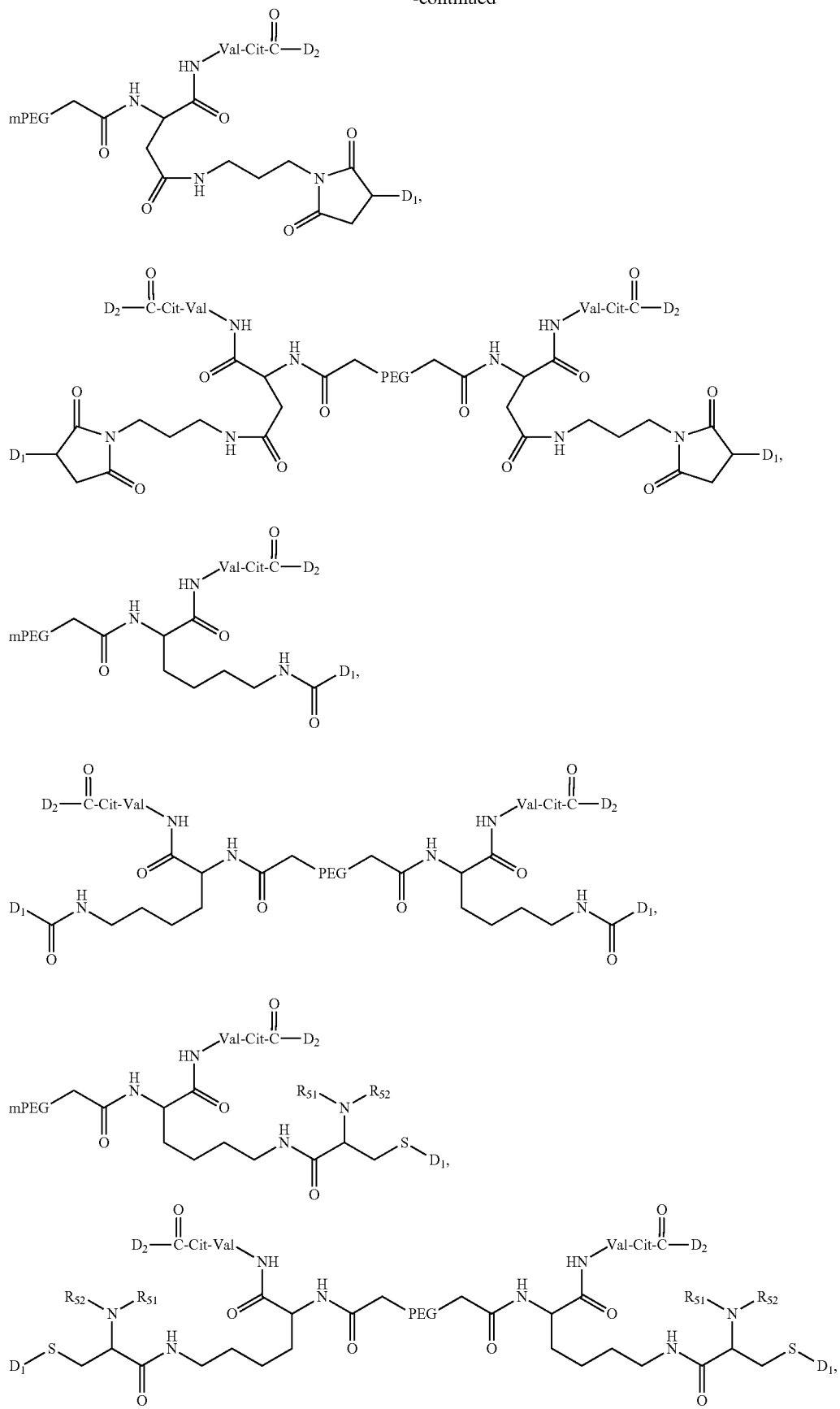

-continued
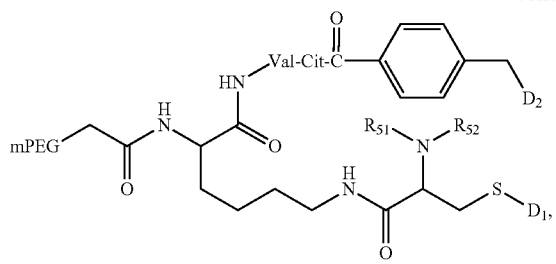
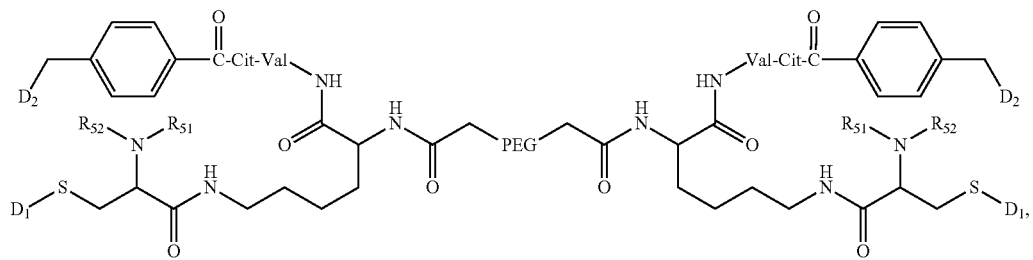
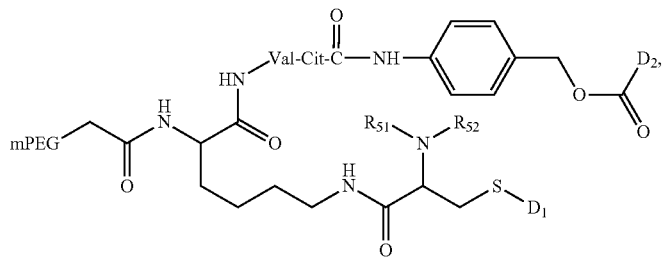
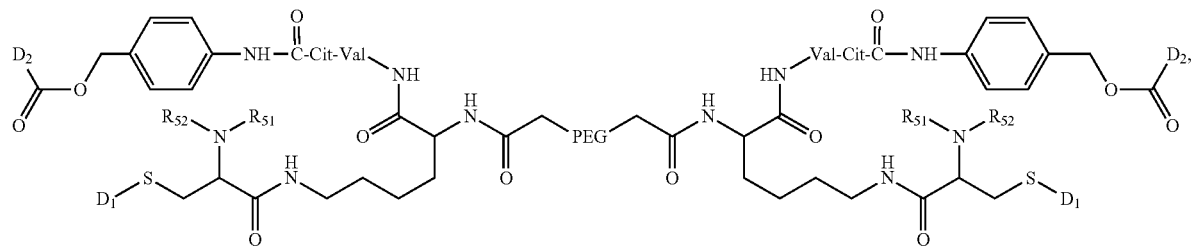
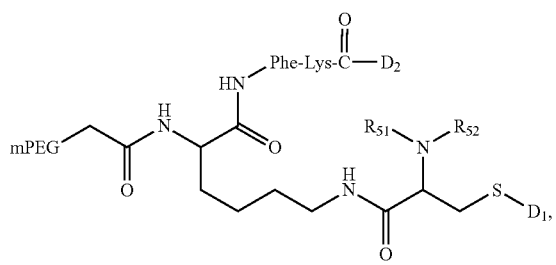
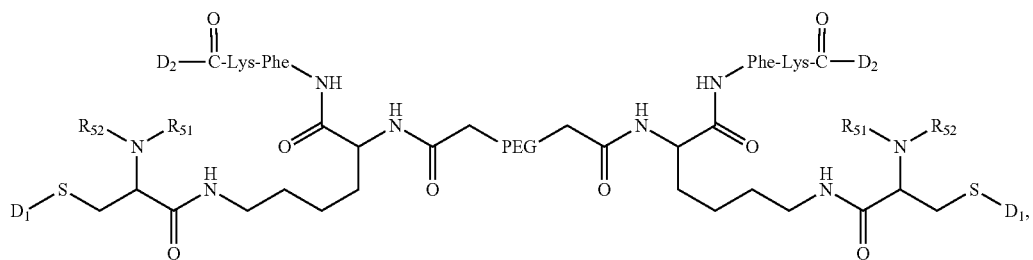

-continued

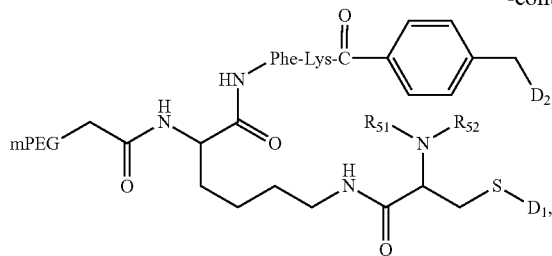

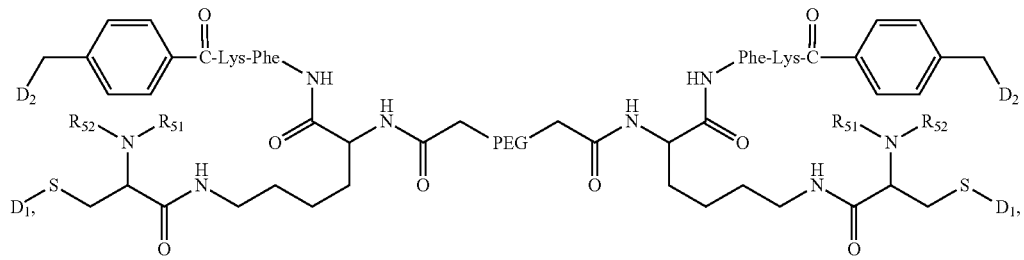

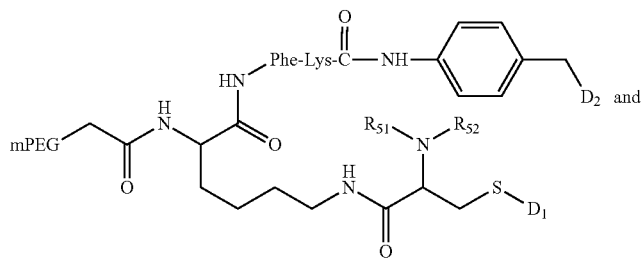

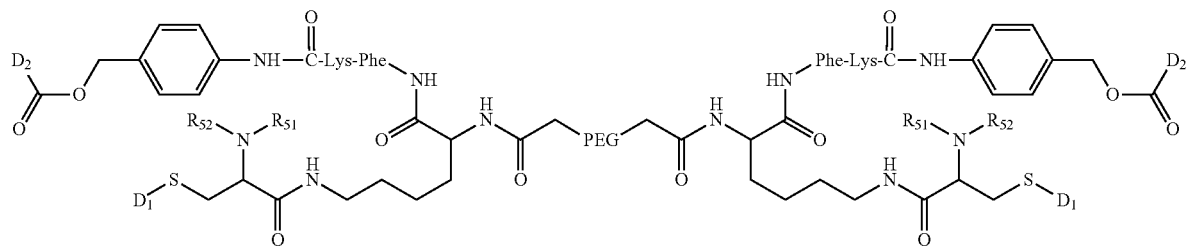

wherein
mPEG has the formula: $CH_3-O(CH_2CH_2O)_n-$;
PEG has the formula $-O(CH_2CH_2O)_n-$;
(n) is a positive integer from about 10 to about 2,300;
$R_{51}$ and $R_{52}$ are independently selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cyloalkyls, aryls, substituted aryls, aralkyls, $C_{1-6}$ heteroalkyls, substituted $C_{1-6}$ heteroalkyls, $C_{1-6}$ alkoxy, $C_{1-6}$ alkyloxycarbonyl, aryloxycarbonyl, phenoxy and $C_{1-6}$ heteroalkoxy;

$D_1$ is a targeting moiety, a functional group or a leaving group; and $D_2$ is a biologically active moiety, a functional group or a leaving group.

Preferred polymeric compounds according to the present invention include:

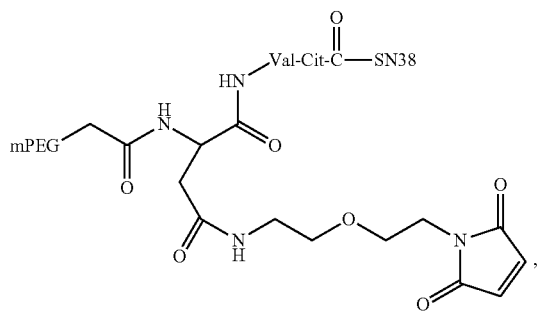

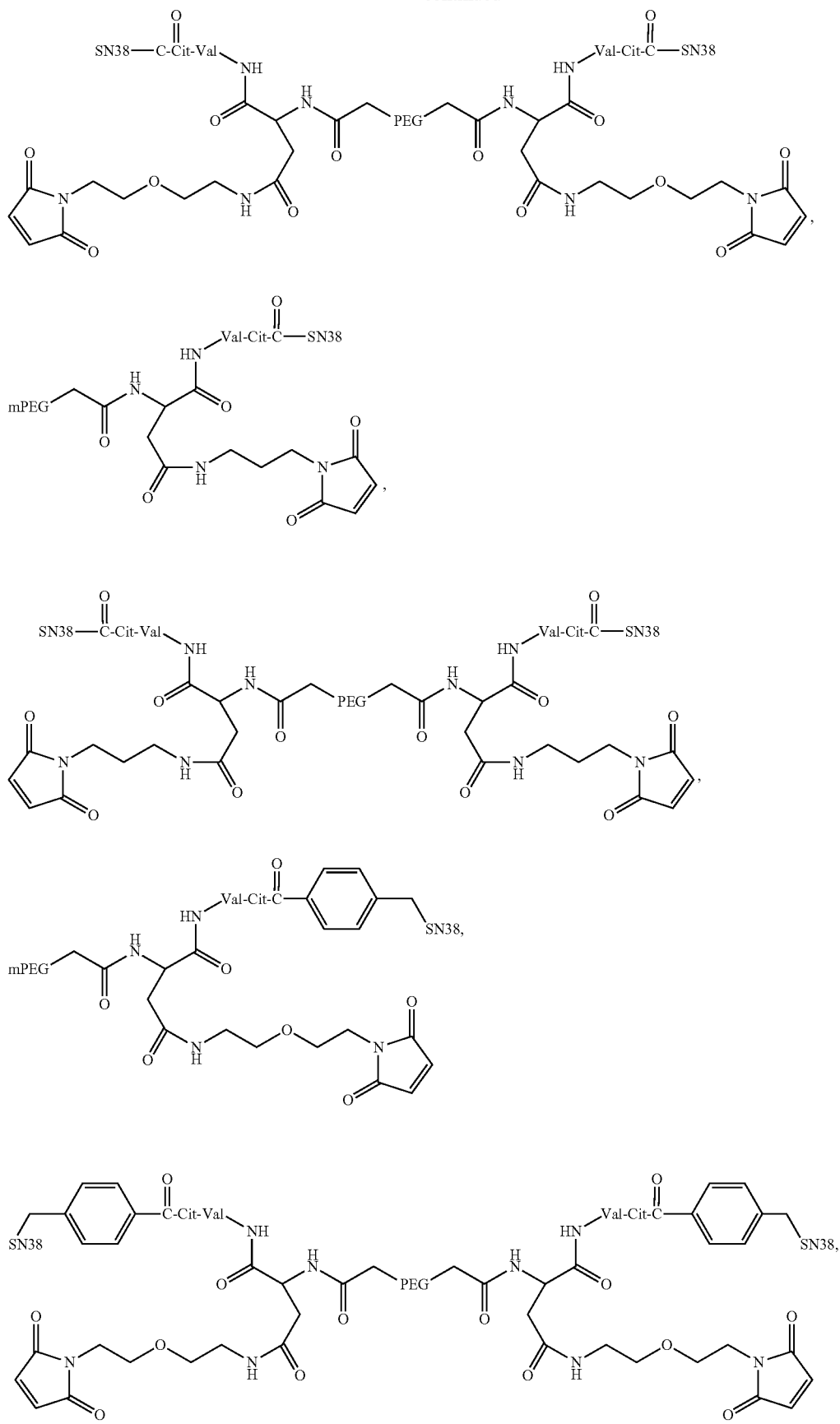

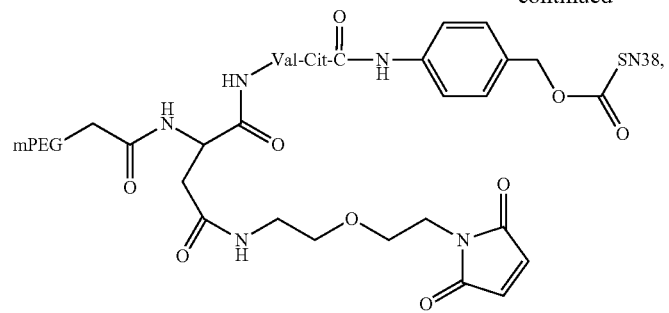
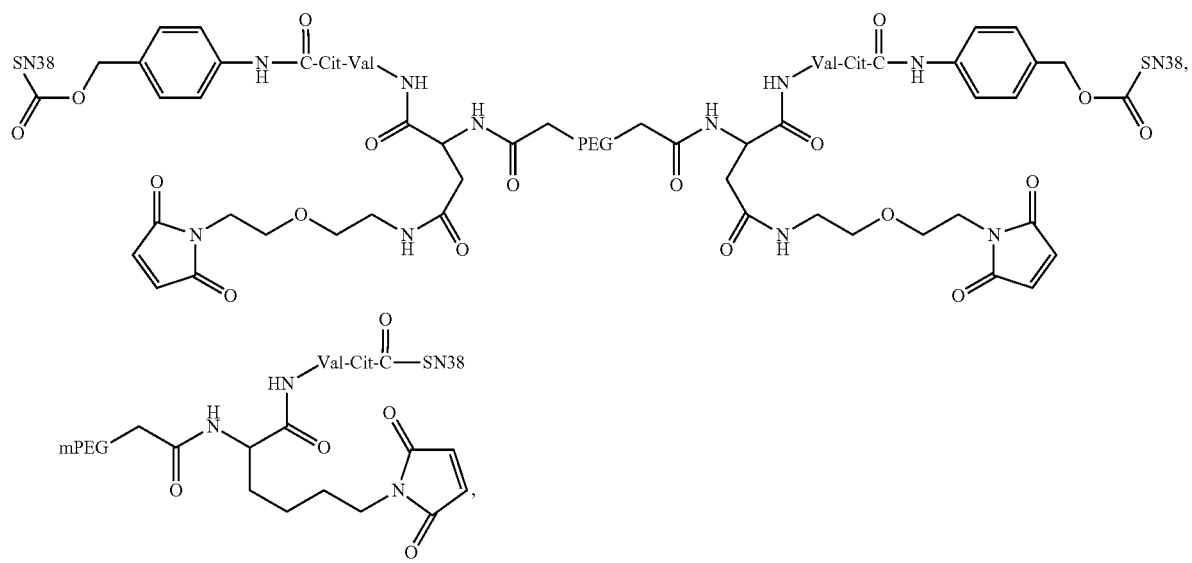
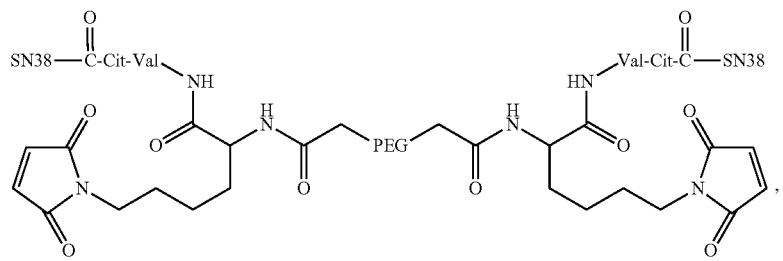
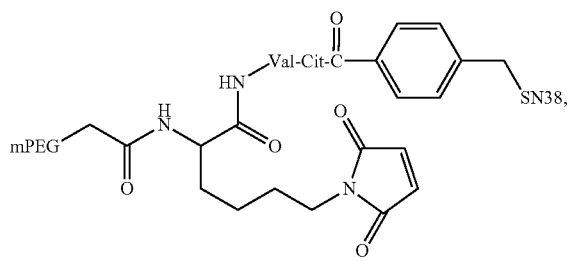
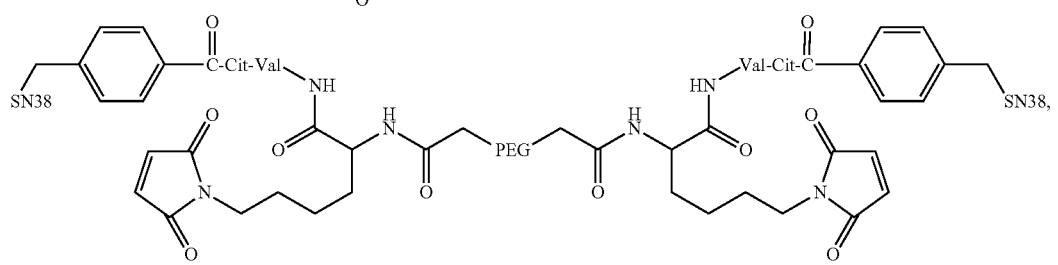

-continued
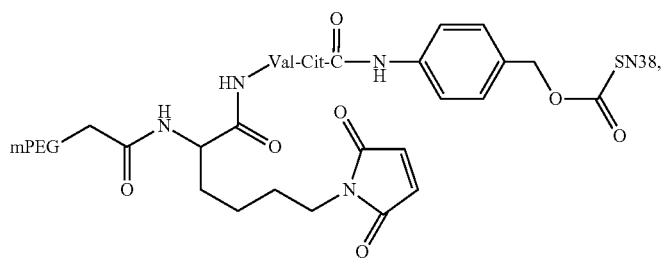
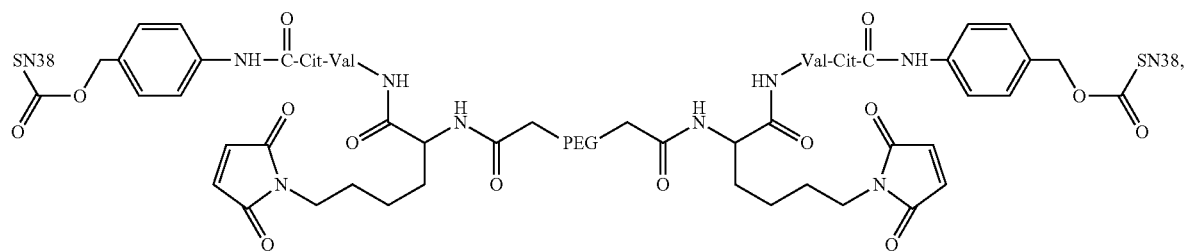
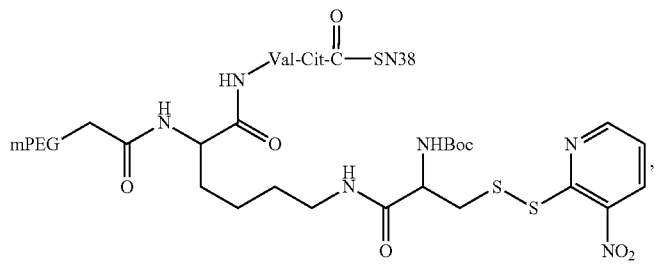
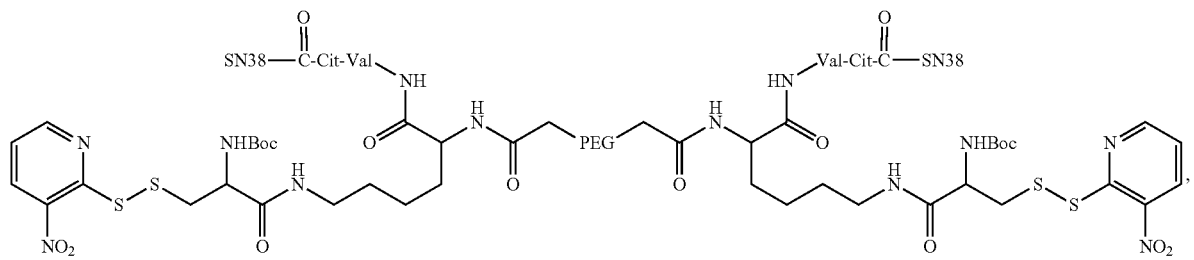
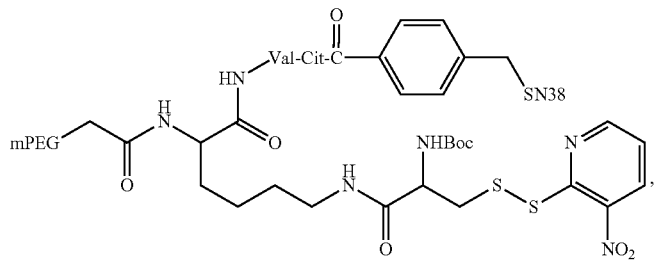
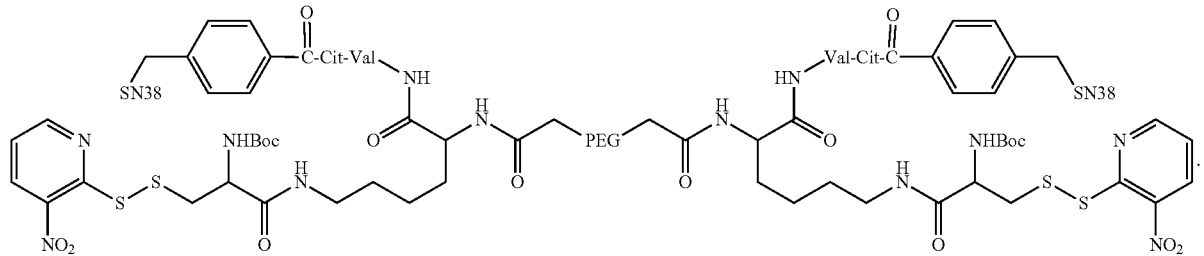

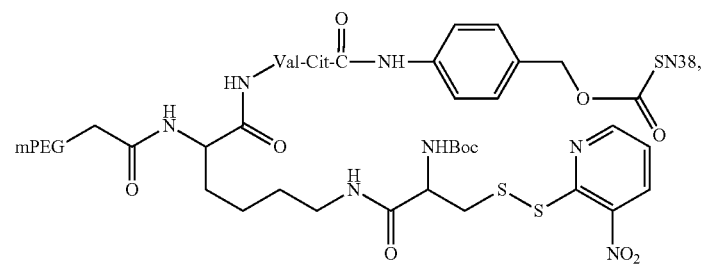
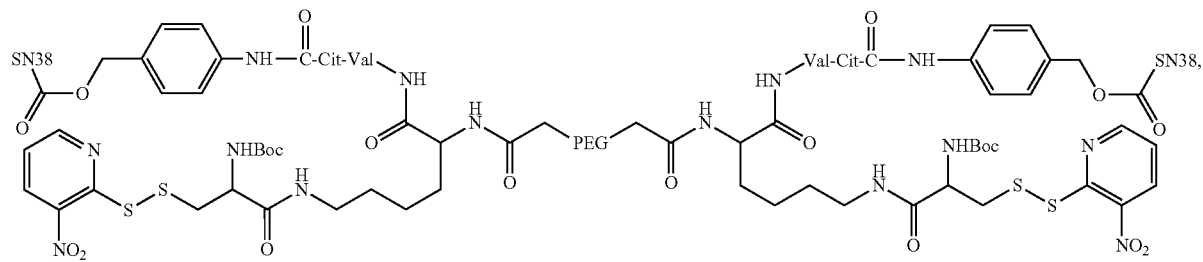
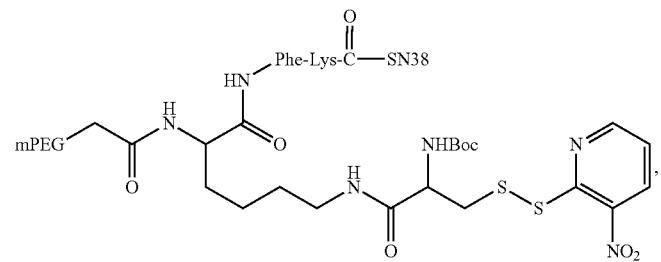
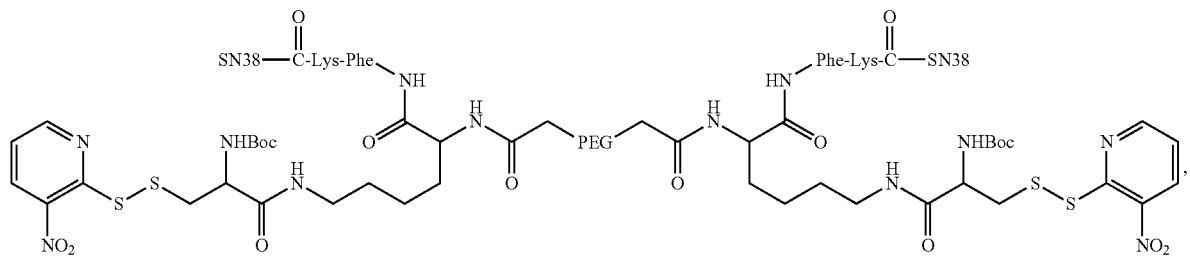
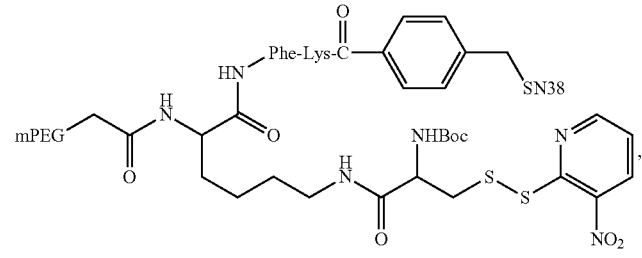
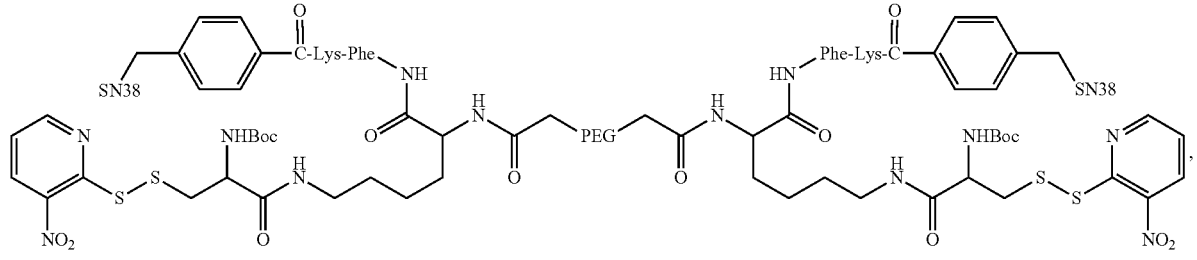

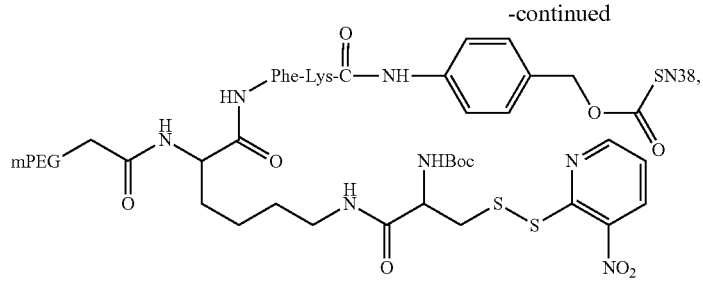
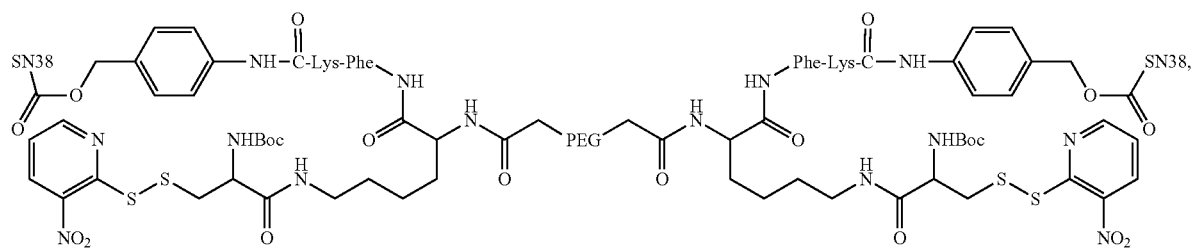
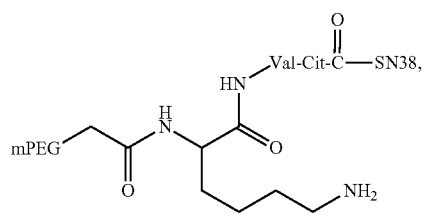
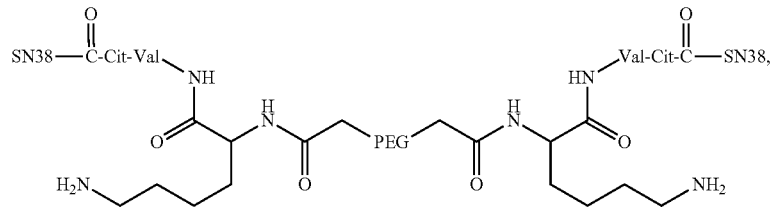
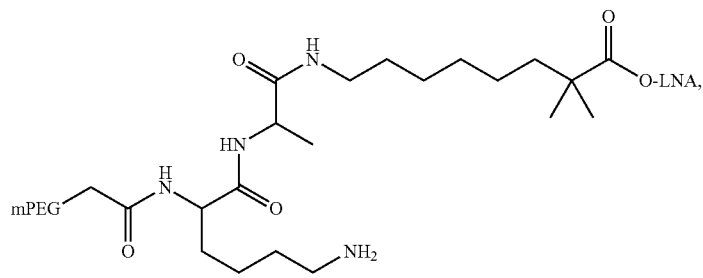
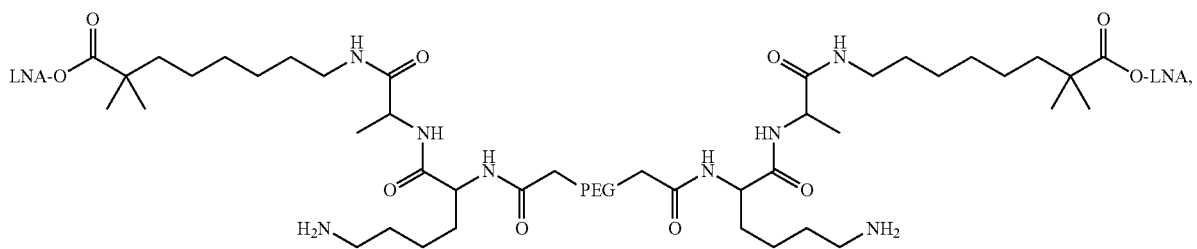

-continued
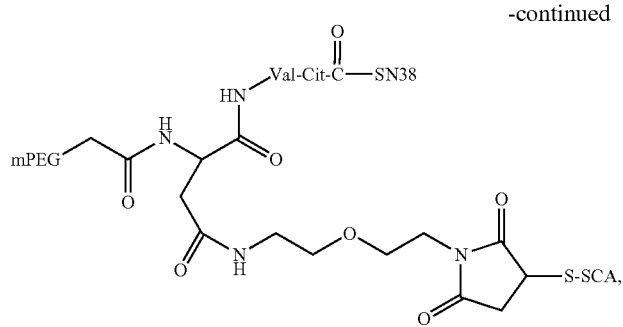
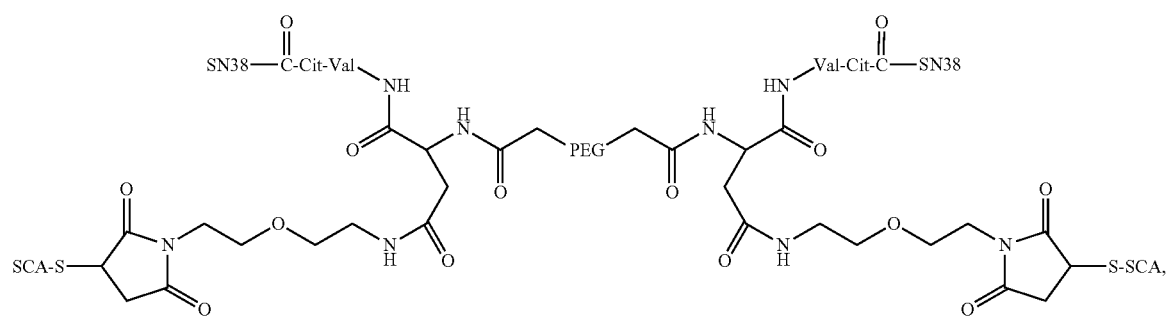
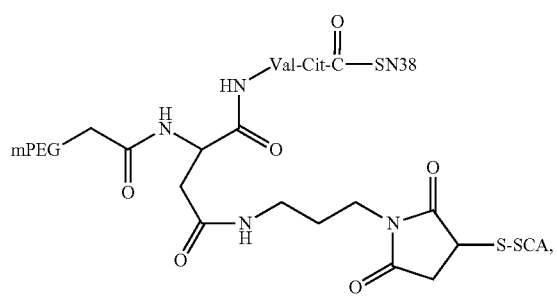
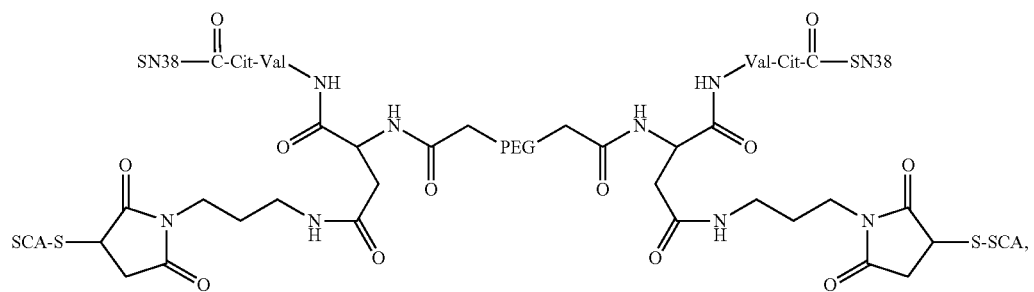
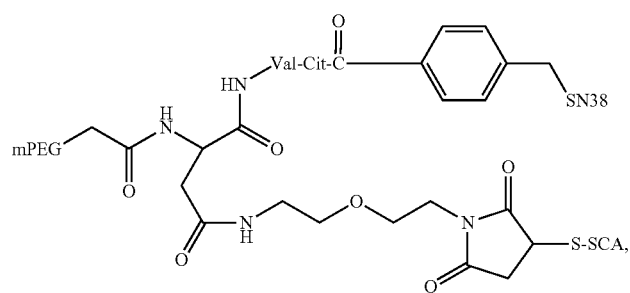

61  62
-continued
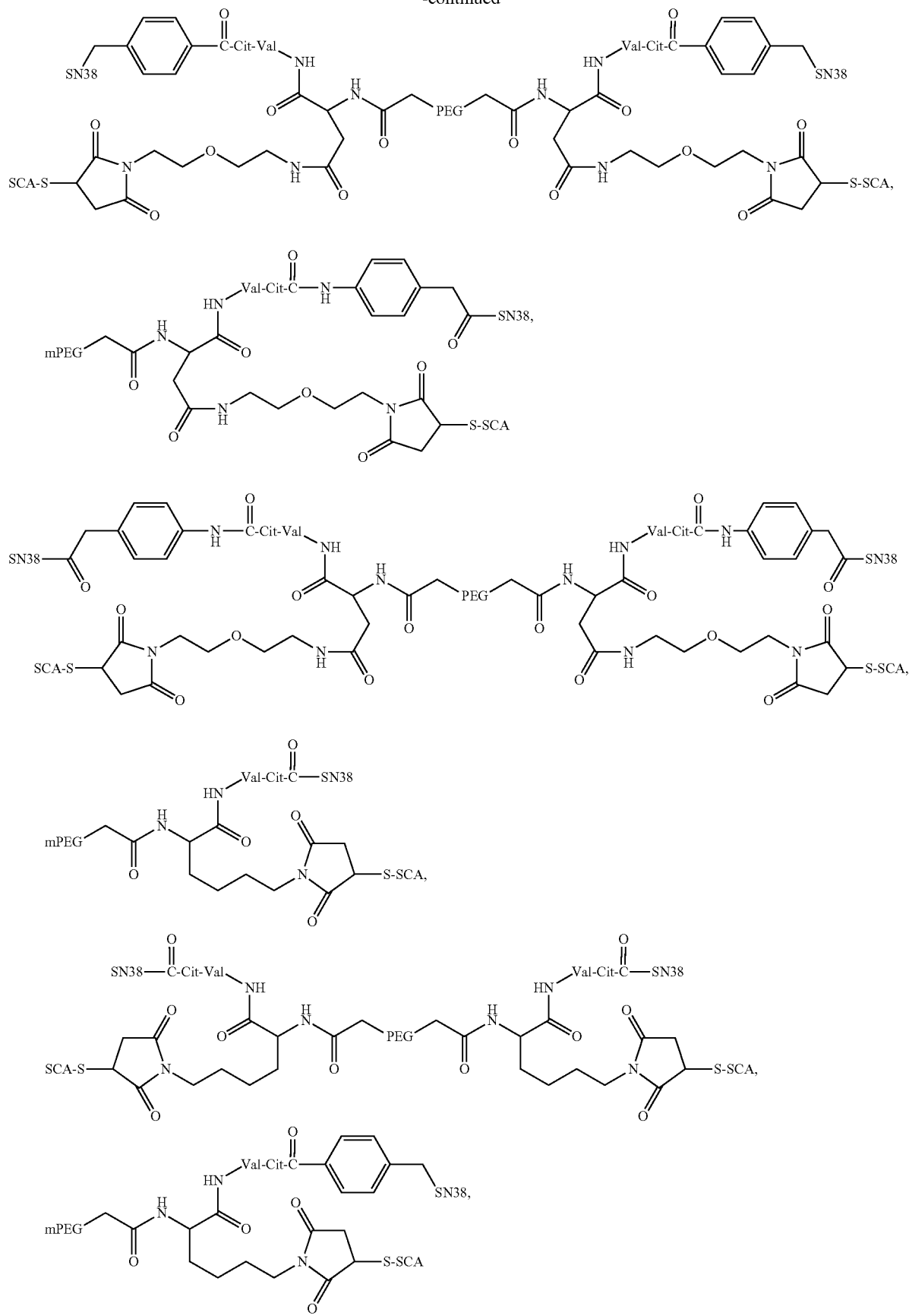

-continued
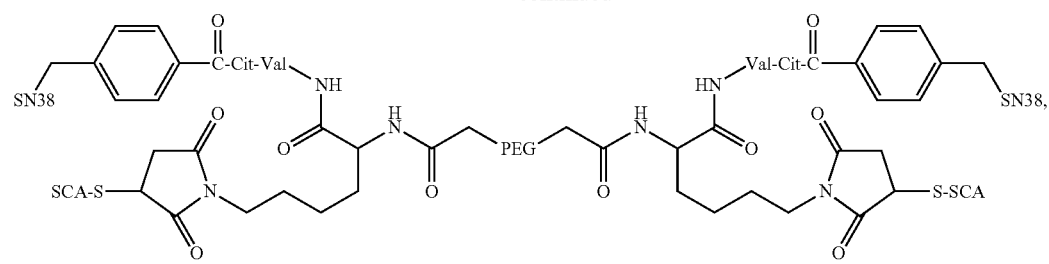
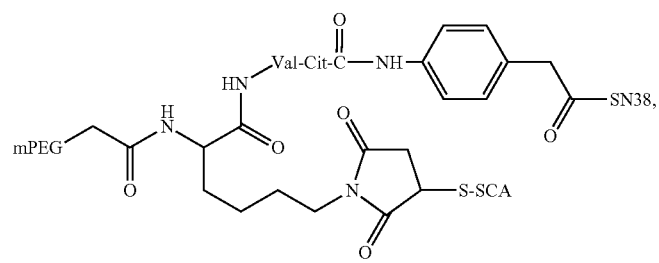
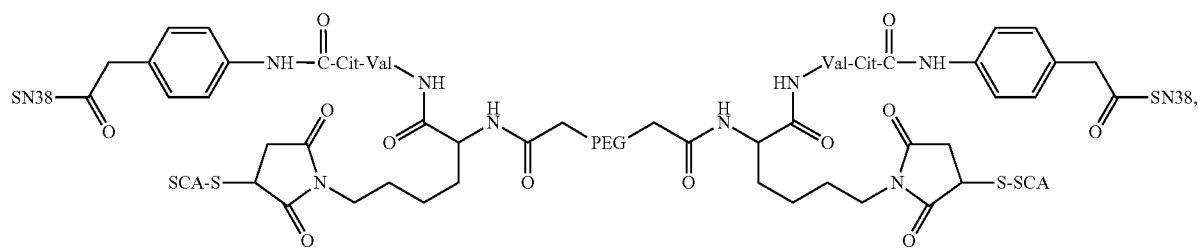
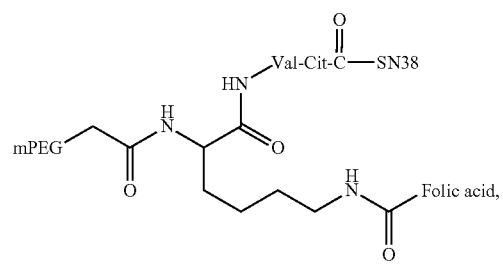
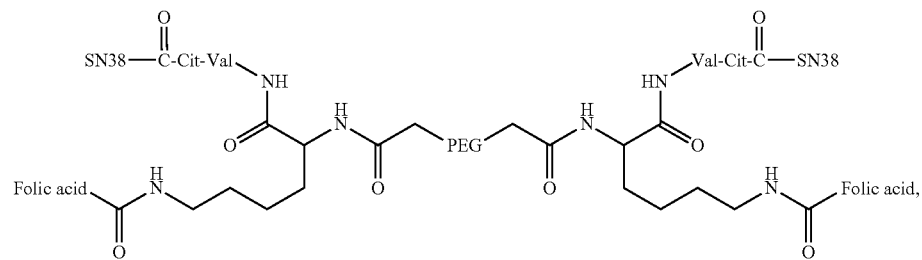
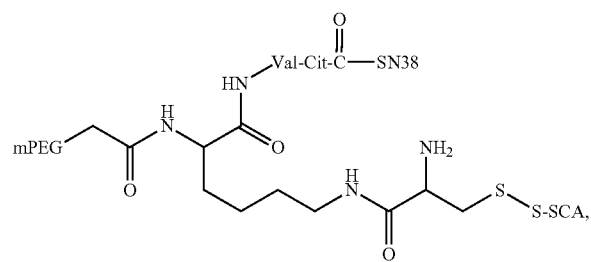

-continued
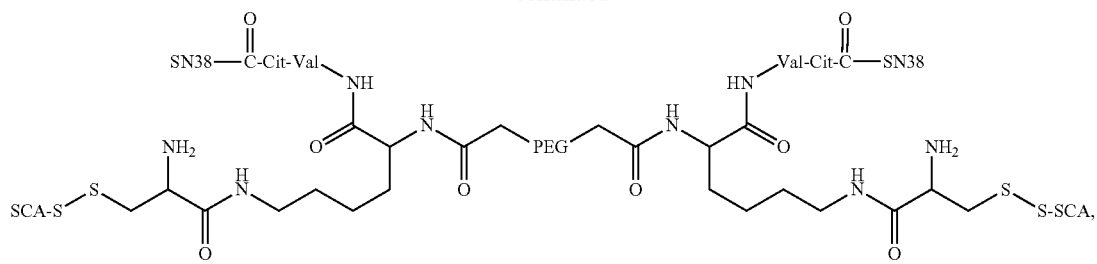
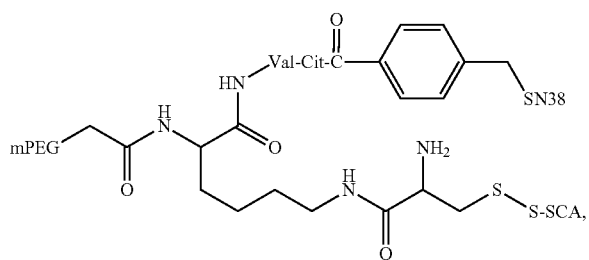
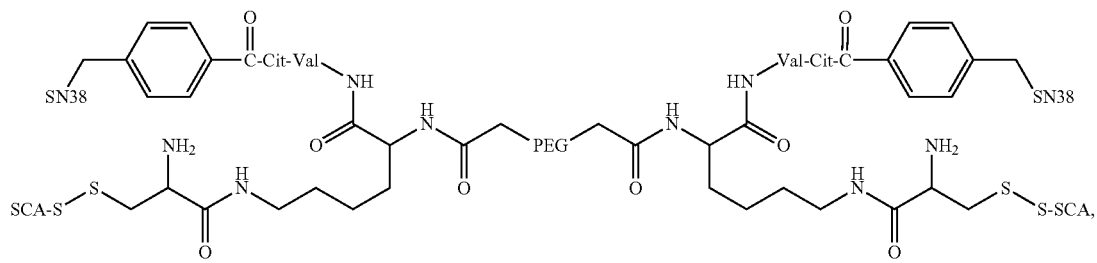
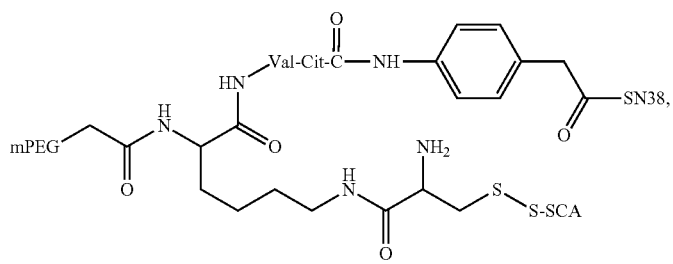
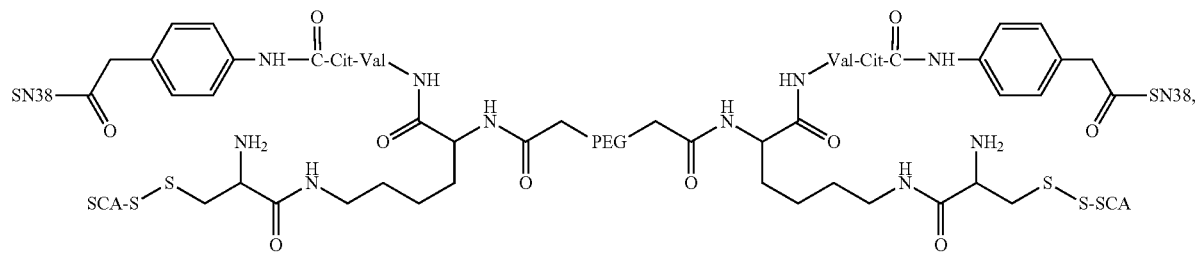
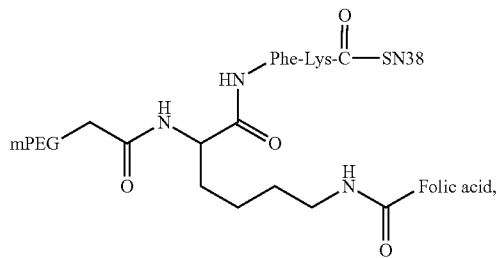

-continued
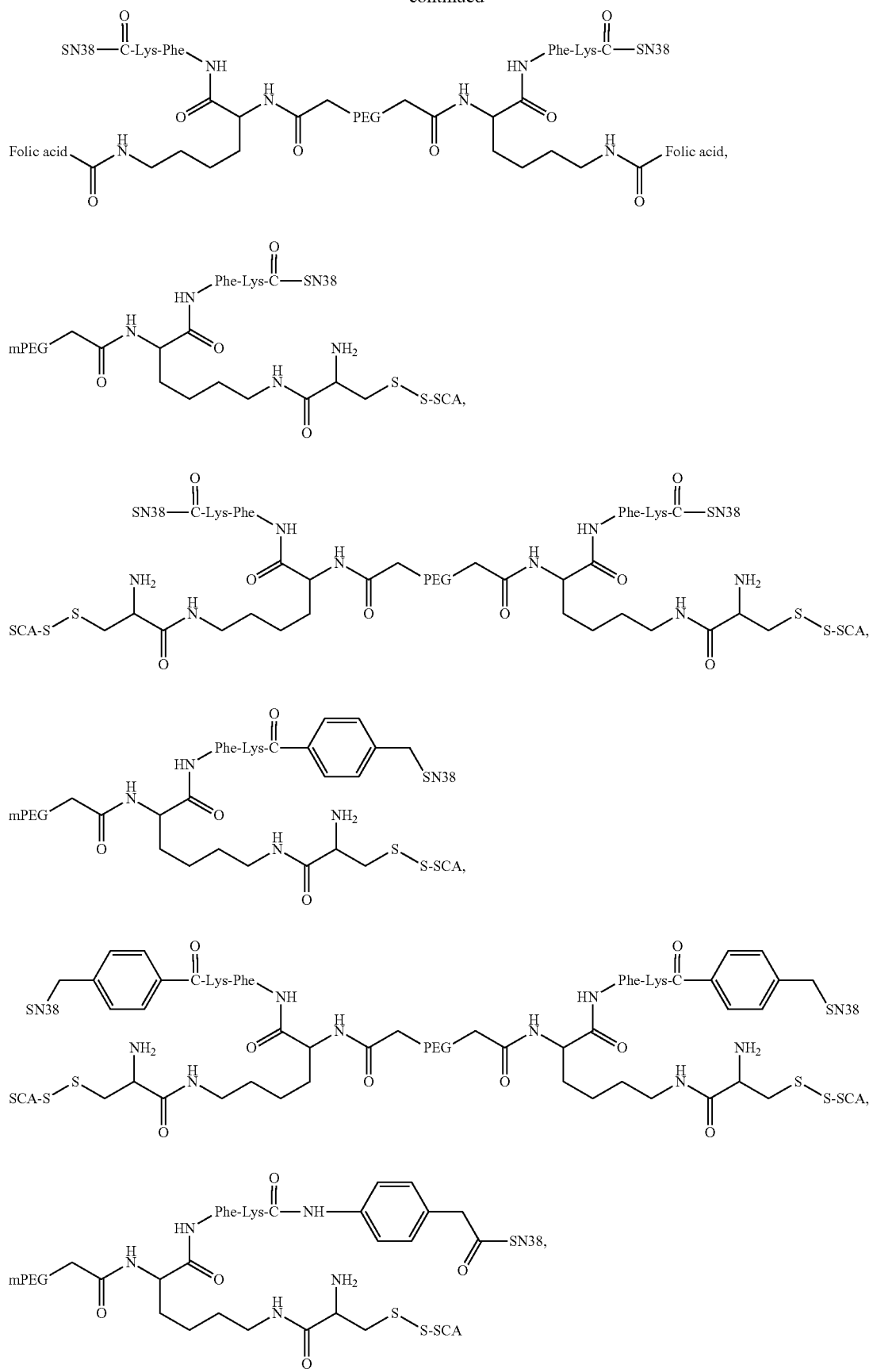

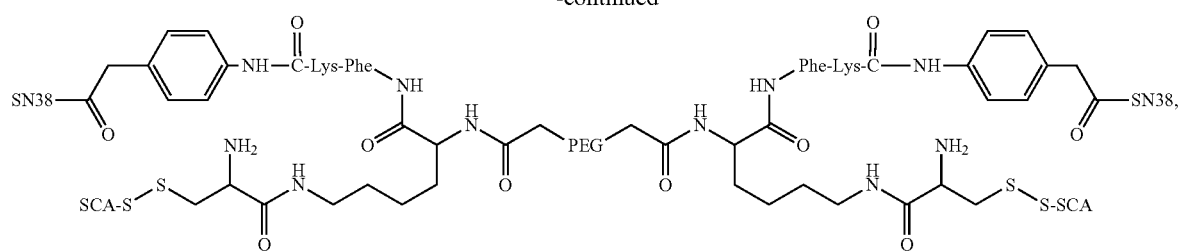
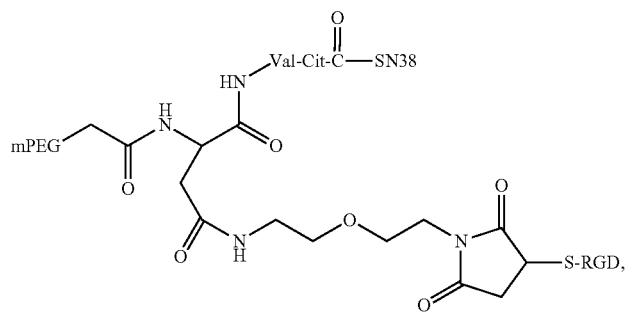
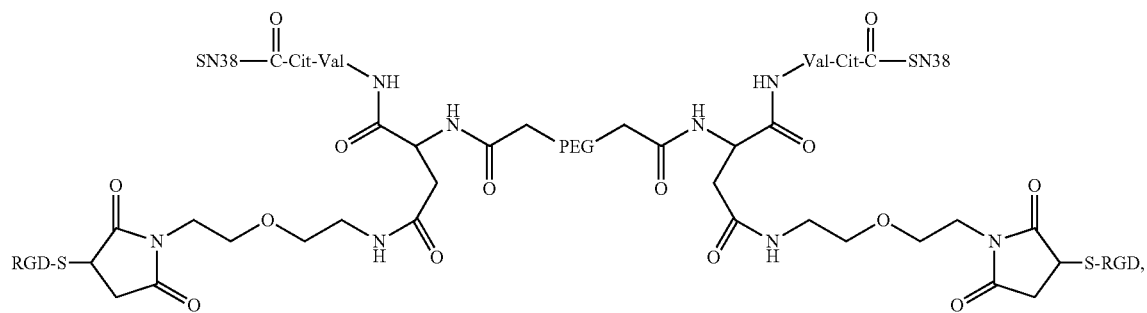
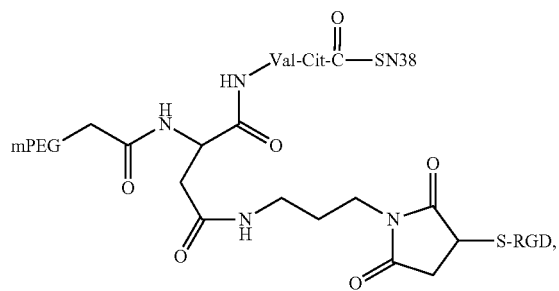
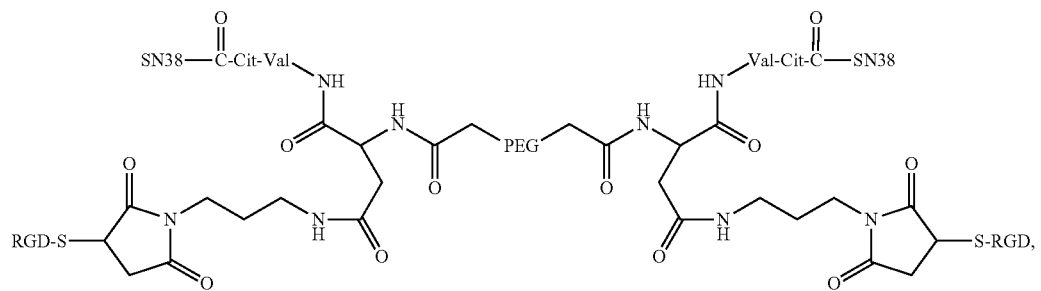

-continued
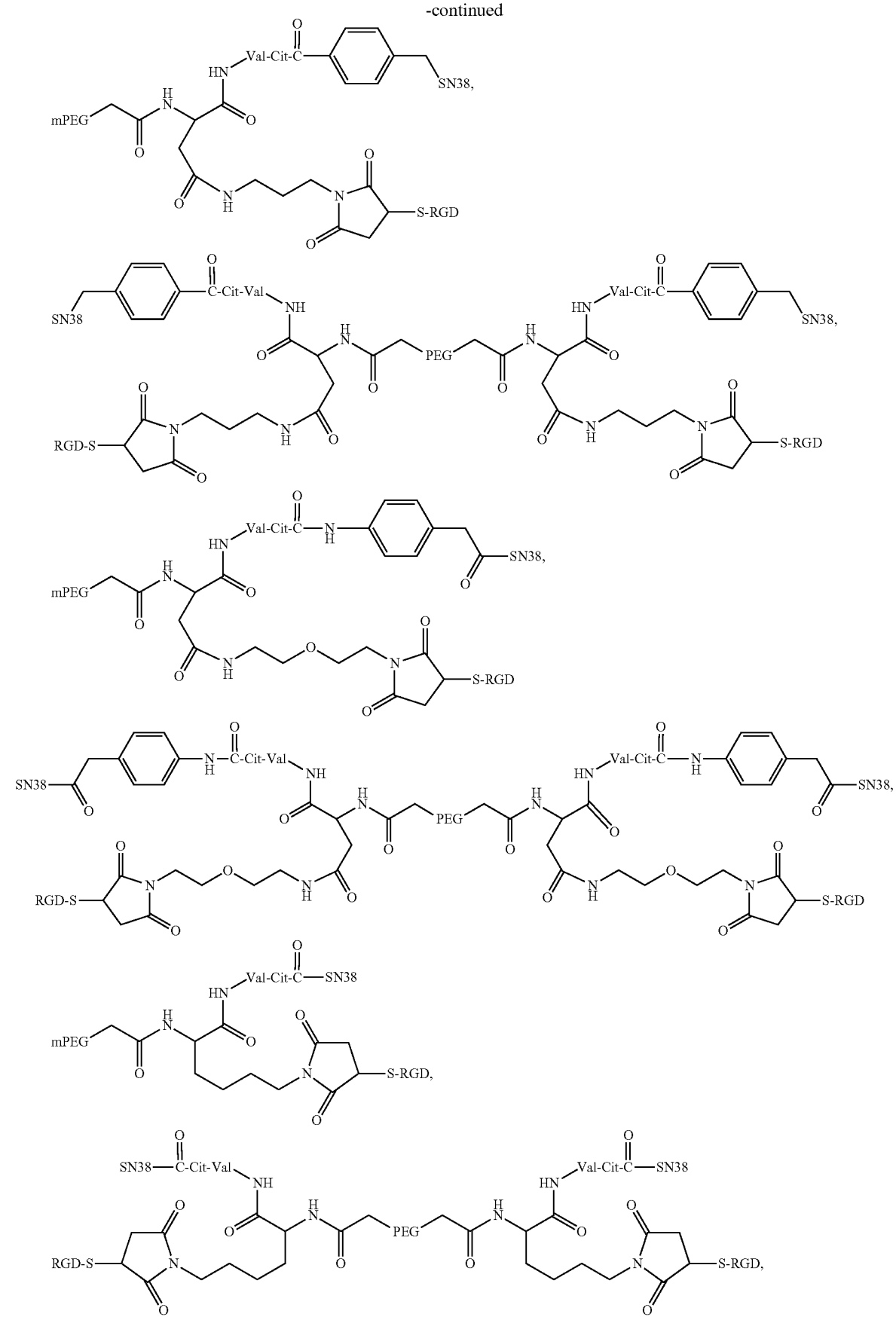

-continued
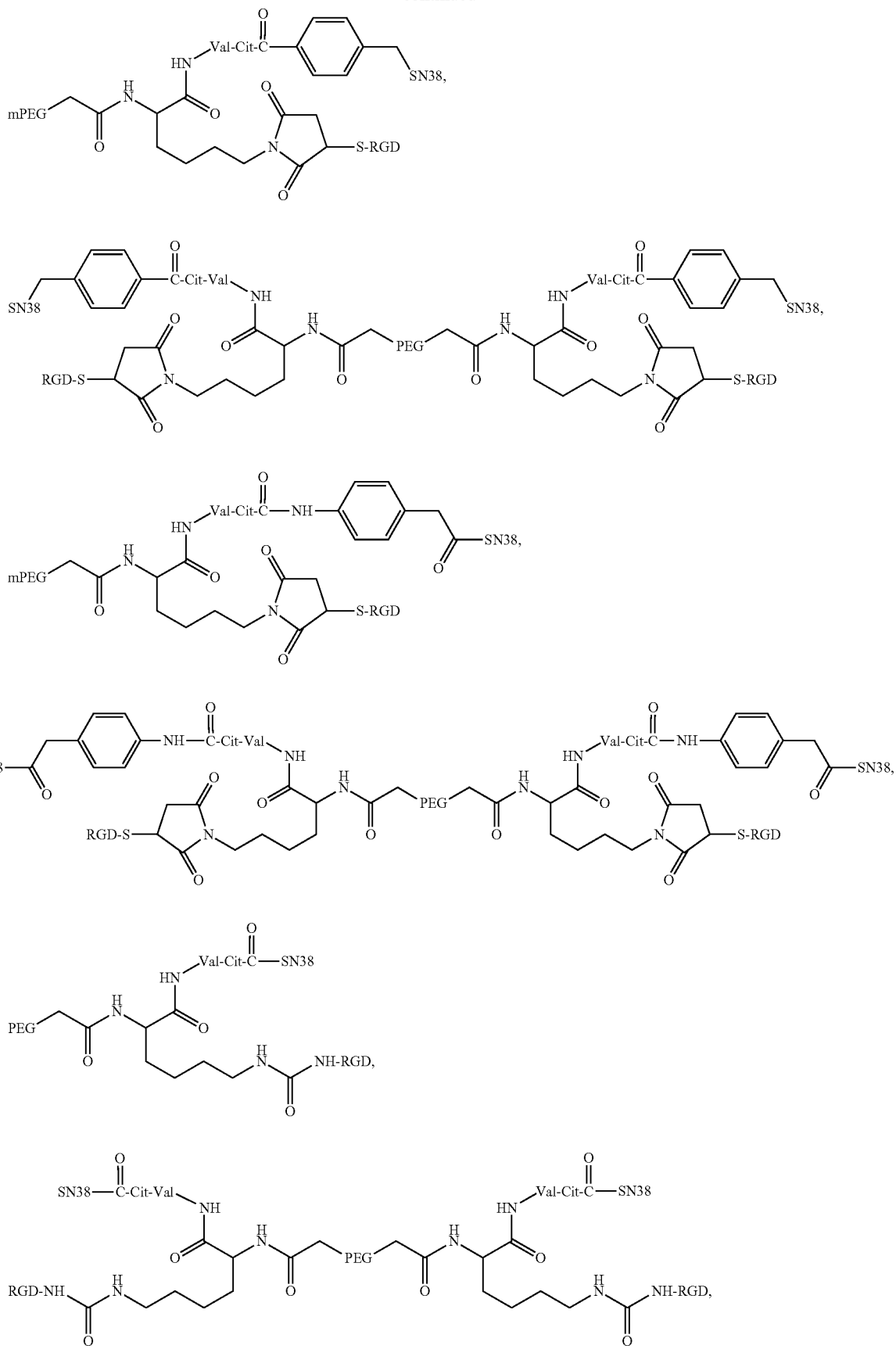

-continued
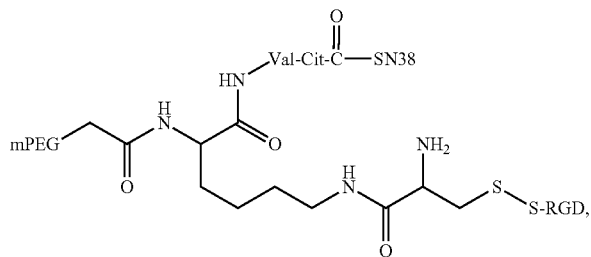
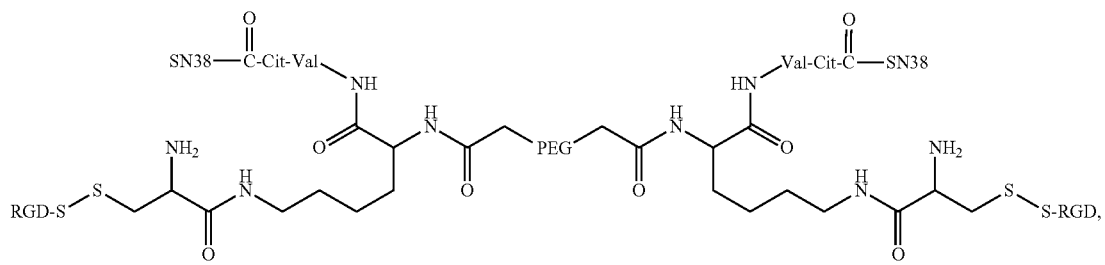
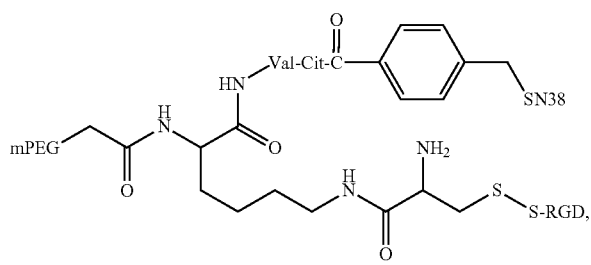
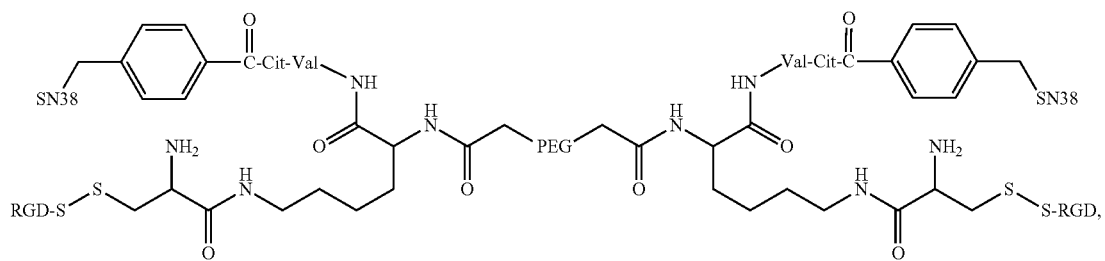
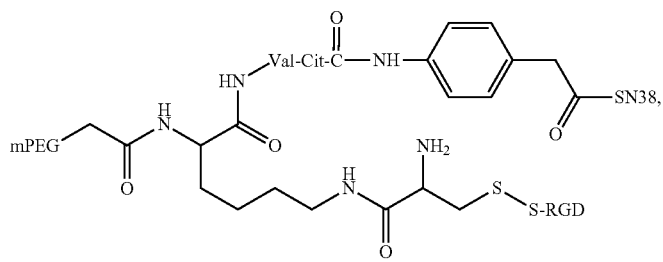
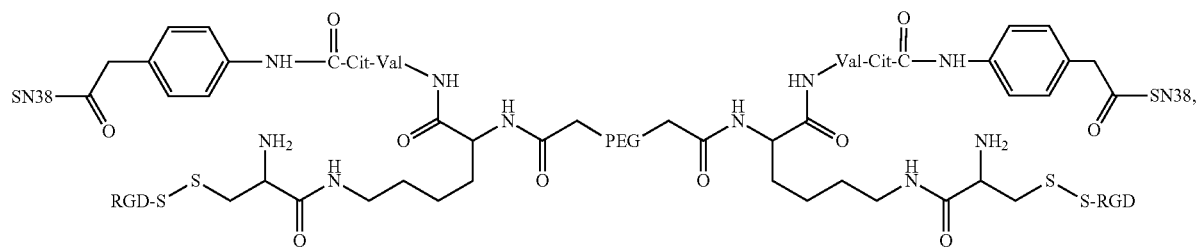

-continued
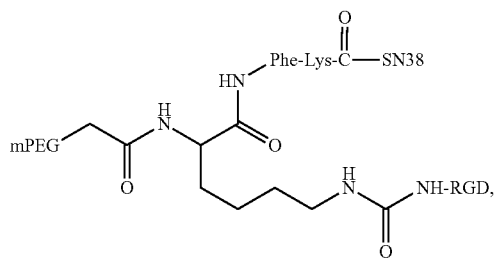
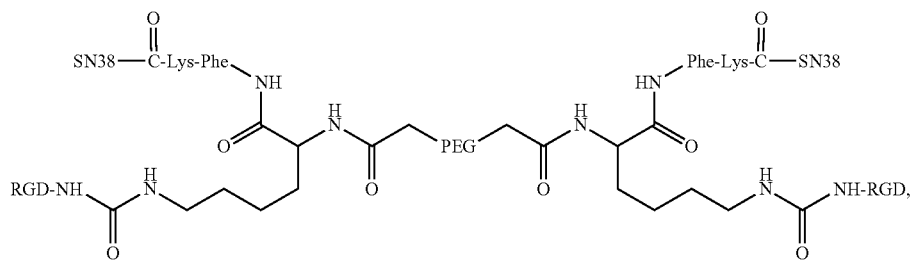
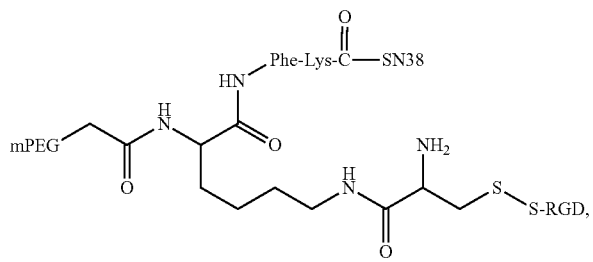
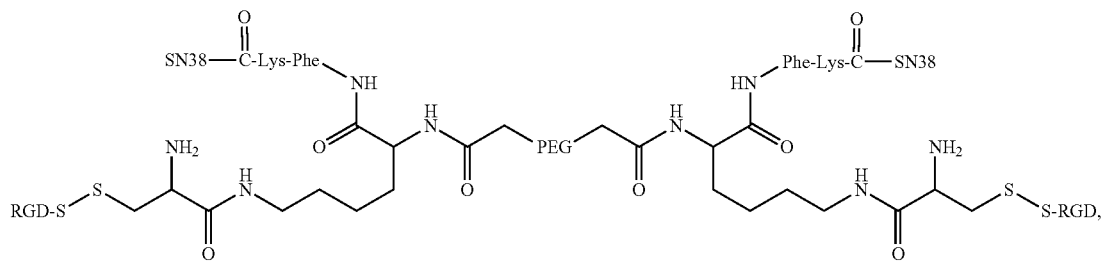
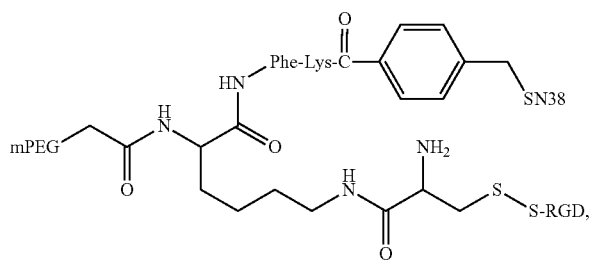
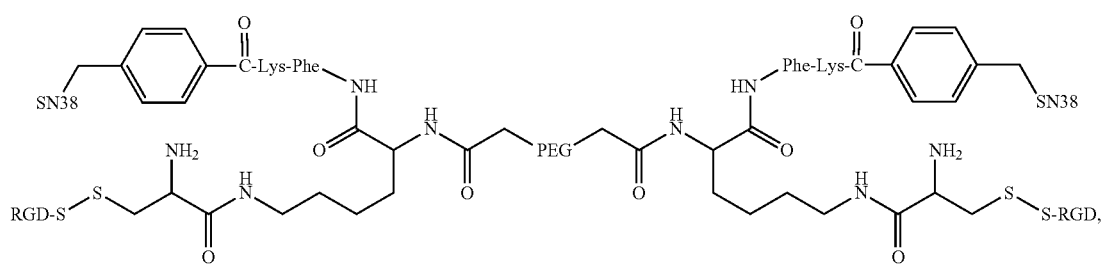

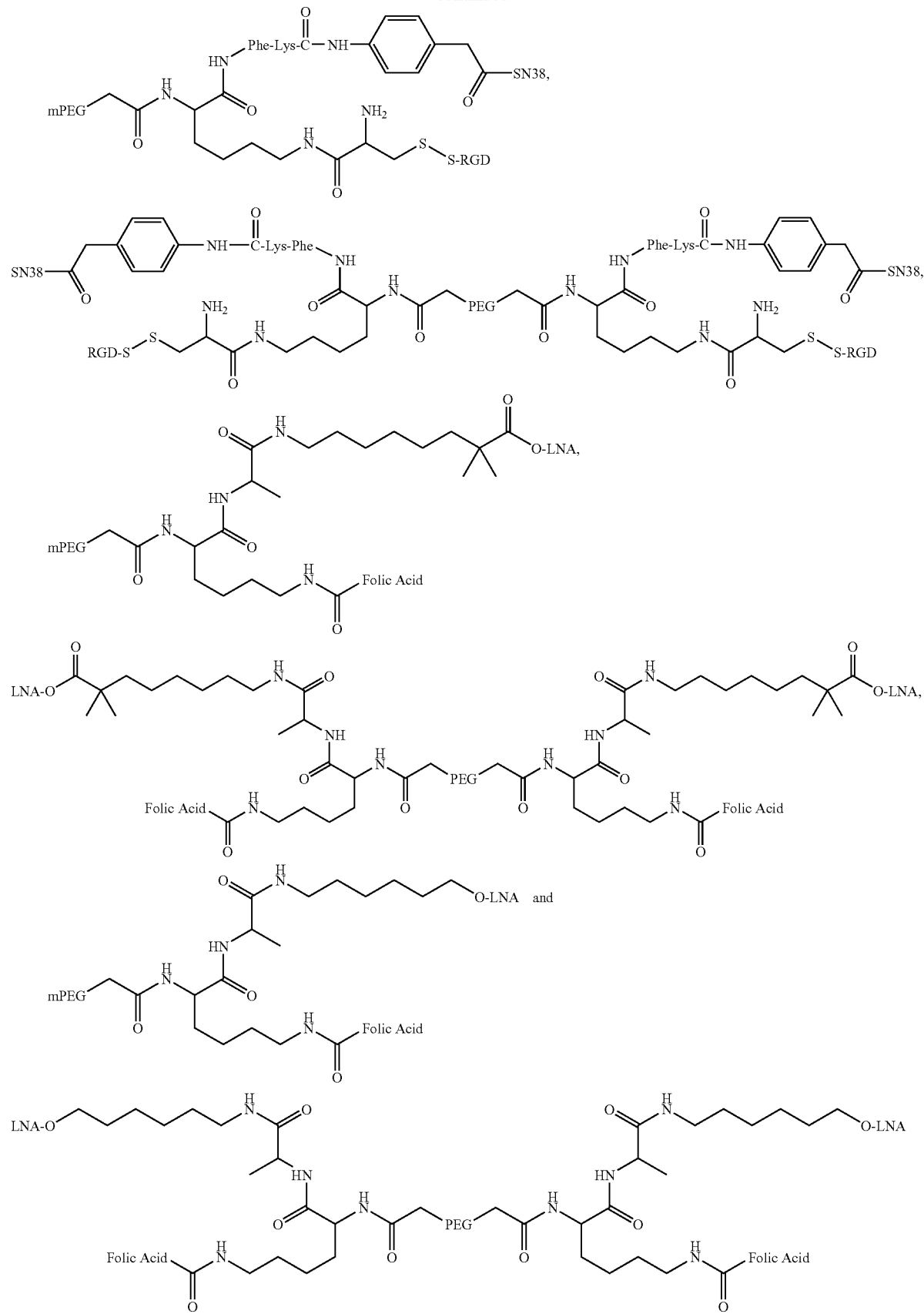

wherein
S-SCA is a single-chain antibody;
RGD is

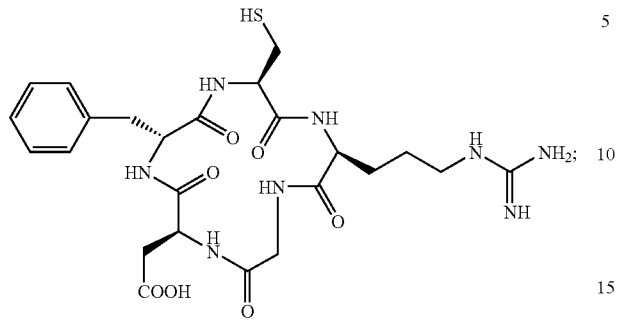

LNA is locked nucleic acids;
Folic acid is a residue of

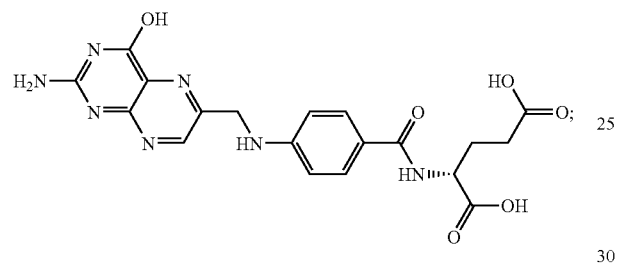

SN38 is 7-ethyl-10-hydroxycamptothecin;
mPEG has the formula: $CH_3-O(CH_2CH_2O)_n-$;
PEG has the formula $-O(CH_2CH_2O)_n-$; and
(n) is a positive integer from about 10 to about 2,300.

I. Methods of Making the Conjugates

Generally, the conjugates can be made by sequentially attaching the polymer, cytotoxic agent and targeting moiety to the multifunctional linker. The exact order of addition is not limited to this order and as will be apparent to those of ordinary skill, there are aspects in which the PEG will be first added to the multifunctional linker followed by the addition of the releasably attached cytotoxic drug followed by the addition of the targeting agent like the monoclonal antibody. Details concerning some preferred aspects of this embodiment are provided in the Examples below.

In one aspect of the invention, the polymeric compound having a multifunctional linker can be prepared by conjugating a polymeric compound having a OH or a leaving group terminal with a nucleophile containing a cytotoxic agent attached through an optional linker. The artisan can use less amount of the nucleohile compare to the number of the leaving groups on the polymer to form a polymeric intermediate containing both cytotoxic agent and leaving groups. This intermediate can further reacted with a targeting moiety to form the polymeric conjugate multisubstituted with cytotoxic agent and targeting agent.

Alternatively, the polymer can be activated with different groups to provide different chemical reactivities toward various nucleophilic moieties. For example, different protecting groups such as tert-Bu ester and methyl ester of carboxylic acid terminals can be deprotected selectively and stepwise to provide various degrees of active group to be conjugated with different biologically active agents such as cytotoxic agent and targeting agent. As shown in FIG. 1, maleimidyl group and succinimidyl ester can react selectively with SH or $NH_2$ containing moieties, respectively.

All reactions described herein are standard chemical reactions with necessary steps and conditions known to those of an ordinary skill. The synthetic reactions described herein therefore do not require undue experimentation.

The methods of preparing a polymeric conjugate containing multifunctional linkers comprising:
reacting a compound of Formula (IIIa):

(IIIa)

with a biologically active moiety-containing compound having Formula (IIIb):

$M_3\text{-}(L_3)_b\text{-}D_{22}$ under conditions sufficient to form a compound of Formula (IIIc):

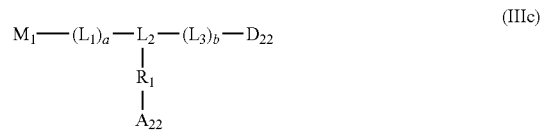

(IIIc)

wherein
$R_1$ is a substantially non-antigenic water-soluble polymer;
$A_{21}$ is a capping group or

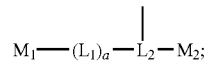

$A_{22}$ is a capping group or

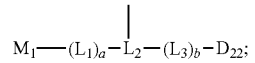

$M_1$ is a functional group;
$D_{22}$ is a biologically active moiety;
$M_2$ is OH or a leaving group;
$M_3$ is OH, $NH_2$, or SH;
$L_1$ is a permanent linker or a releasable linker;
$L_2$ is a multifunctional linker;
$L_3$ is a permanent linker or a releasable linker; and
(a) and (b) are independently zero or a positive integer.
The methods further include
reacting the compound of Formula (IIIc):

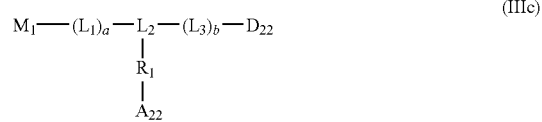

(IIIc)

with a nucleophilic moiety-containing moiety having Formula (IIId)

$D_{21}\text{-}M_4$ (IIId)

under conditions sufficient to form a compound of Formula (IIIe):

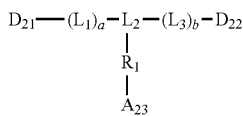

wherein:
A$_{23}$ is a capping group or

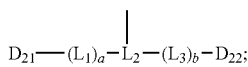

M$_1$ is a functional group;
D$_{21}$ is a targeting moiety; and
M$_4$ is OH, NH$_2$, or SH.

The attachment of the nucleophilic compound such as Formula (IIIb) to the PEG or other polymer can be done using standard chemical synthetic techniques well known to those of ordinary skill. The activated polymer portion such as SC-PEG, PEG-amine, PEG acids, etc. can be obtained from either commercial sources or synthesized by the artisan without undue experimentation.

Attachment of nucleophilic compound such as Formula (IIIb) to the polymer portion is preferably carried out in the presence of a coupling agent. A non-limiting list of suitable coupling agents include 1,3-diisopropylcarbodiimide (DIPC), any suitable dialkyl carbodiimides, 2-halo-1-alkyl-pyridinium halides, (Mukaiyama reagents), 1-(3-dimethylaminopropyl)-3-ethyl carbodiimide (EDC), propane phosphoric acid cyclic anhydride (PPACA) and phenyl dichlorophosphates, etc. which are available, for example from commercial sources such as Sigma-Aldrich Chemical, or synthesized using known techniques.

Preferably, the reactions are carried out in an inert solvent such as methylene chloride, chloroform, DMF or mixtures thereof. The reactions can be preferably conducted in the presence of a base, such as dimethylaminopyridine (DMAP), diisopropylethylamine, pyridine, triethylamine, etc. to neutralize any acids generated. The reactions can be carried out at a temperature from about 0° C. up to about 22° C. (room temperature). Some particular embodiments are prepared by the methods described herein.

H. Methods of Treatment

In alternative aspects of the invention, there are also provided methods of treating a mammal, comprising administering an effective amount of a pharmaceutical composition containing a compound of the present invention of Formula (I) to a patient in need thereof.

In one preferred aspect of the invention, there are also provided methods of treating a patient having a malignancy or cancer, comprising administering an effective amount of a pharmaceutical composition containing the compound of Formula (I) to a patient in need thereof. In some aspects, the cancer being treated can be one or more of the following: solid tumors, lymphomas, small cell lung cancer, acute lymphocytic leukemia (ALL), pancreatic cancer, glioblastoma, ovarian cancer, gastric cancers, etc. The compositions are useful for treating neoplastic disease, reducing tumor burden, preventing metastasis of neoplasms and preventing recurrences of tumor/neoplastic growths in mammals.

Another aspect of the present invention provides methods of treatment for various medical conditions in mammals. Briefly stated, any biologically active moiety which can be attached to the PEG polymer can be administered to a mammal in need of such treatment. Any oligonucleotide, etc. which has therapeutic effects in the unconjugated state can be used in its conjugated form, made as described herein.

The amount of the composition that is administered will depend upon the parent molecule included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. Those skilled in the art will determine the optimal dosing of the polymeric transport conjugates selected based on clinical experience and the treatment indication. Actual dosages will be apparent to the artisan without undue experimentation.

The compounds of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, intraperitoneal, subcutaneous injection and the like. Such administration may also be by infusion into a body space or cavity, as well as by inhalation and/or intranasal routes. In preferred aspects of the invention, however, the polymeric conjugates are parenterally administered to mammals in need thereof.

In a further aspect of the invention, there are provided methods of administering polynucleotides (oligonucleotides), preferably antisense oligonucleotides to mammalian cells. The methods include delivering an effective amount of a conjugate prepared as described herein to the condition being treated will depend upon the polynucleotides efficacy for such conditions. For example, if the unconjugated oligonucleotides (for example antisense BCL2 oligonucleotides, antisense Survivin oligonucleotides) has efficacy against certain cancer or neoplastic cells, the method would include delivering a polymer conjugate containing the oligonucleotides to the cells having susceptibility to the native oligonucleotides. The delivery can be made in vivo as part of a suitable pharmaceutical composition or directly to the cells in an ex vivo environment. In one particular treatment, the polymeric conjugates including oligonucleotides (SEQ ID NO. 1, SEQ ID NOs: 2 and 3, and SEQ ID NO: 4) can be used.

EXAMPLES

The following examples serve to provide further appreciation of the invention but are not meant in any way to restrict the scope of the invention. The bold-faced numbers recited in the Examples correspond to those shown in FIG. 1. Abbreviations are used throughout the examples such as, DCC (dicyclohexylcarbodiimide), DCM (dichloromethane), DCU (Dicyclohexylurea), DIEA (diisopropylethylamine), DIPC (diisopropylcarbodiimide), DMAP (4-dimethylaminopyridine), DMF (N,N'-dimethylformamide), DSC (disuccinimidyl carbonate), EDC (1-(3-dimethylaminopropyl)-3-ethyl carbodiimide), EEDQ (2-ethoxy-1-ethoxycarbonyl-1,2-dihydroquinoline), IPA (isopropanol), NHS (N-hydroxysuccinimide), NMM (N-methylmorpholine), PEG (polyethylene glycol), SCA-SH (single-chain antibody), SN38 (7-ethyl-10-hydroxycamptothecin), TBDPS (tert-butyl-dipropylsilyl), and TEA (triethylamine).

General Procedures. All reactions are run under an atmosphere of dry nitrogen or argon. Commercial reagents are used without further purification. All PEG compounds are dried in vacuo or by azeotropic distillation from toluene prior to use. $^1$H NMR spectra were obtained at 300 MHz and $^{13}$C NMR spectra at 75.46 MHz using a Varian Mercury 300 NMR spectrometer and deuterated chloroform as the solvents unless otherwise specified. Chemical shifts (δ) are reported in parts per million (ppm) downfield from tetramethylsilane (TMS).

HPLC Method. The reaction mixtures and the purity of intermediates and final products are monitored by a Beckman Coulter System Gold® HPLC instrument. It employs a ZORBAX® 300SB C8 reversed phase column (150×4.6 mm) or a Phenomenex Jupiter® 300A C18 reversed phase column (150×4.6 mm) with a 168 Diode Array UV Detector, using a gradient of 10-90% of acetonitrile in 0.05% trifluoroacetic acid (TFA) at a flow rate of 1 mL/min.)

Example 1

N-(Methoxycarbonyl)maleimide (Compound 1)

Methylchloroformate (4.4 mL, 56.7 mmol, 1 eq) was added to a solution of maleimide (5.5 g, 56.7 mmol, 1 eq) and NMM (6.2 mL, 56.7 mmol, 1 eq) in 200 mL of EtOAc at 0° C. The suspension was stirred at 0° C. for 30 minutes, filtered and washed with EtOAc. Filtrate and washings were combined and washed with cold water and dried over anhydrous $Na_2SO_4$. After filtration and evaporation under vacuum a pink solid was obtained. Purification by column chromatography on silica gel (Hexane-EtOAc, 1:1, v/v) provided the product (4.8 g, 55%).

Example 2

$N^\epsilon$-Maleoyl-α-(Boc)-L-lysine (Compound 2)

N-(Methoxycarbonyl)maleimide (315 mg, 2.03 mmol, 1 eq) was added to a solution of Boc-L-lysine (500 mg, 2.03 mmol, 1 eq) in 10 mL of saturated aqueous $NaHCO_3$ at 0° C. The mixture was stirred vigorously at 0° C. for 40 minutes and at room temperature for an additional hour. After cooling to 0° C., the solution was acidified to pH 3.0 with concentrated $H_2SO_4$ before extracting with ethyl acetate. The organic layers were combined and dried over anhydrous $MgSO_4$. After removing the solvent in vacuo, the residue was purified by column chromatography on silica gel using a mixture of $CHCl_3$-MeOH (5:1, v/v) to provide the product (458 mg, 69%): $^1$H NMR δ 1.39-1.87 (6 H, m, $(CH_2)_3$), 1.44 (9H, s, Boc), 3.52 (2H, t, J=7.2 Hz, $NCH_2$), 4.25-4.30 (1H, m, CH), 5.15 (1H, d, NH), 6.70 (2H, s, maleimide).

Example 3

$N^\epsilon$-Maleoyl-α-L-lysine (Compound 3)

A solution of $N^\epsilon$-maleoyl-α-(Boc)-L-lysine (172 mg, 0.53 mmol) in 5 mL anhydrous DCM was treated with 10 mL of 2N HCl in ethyl ether for an hour at room temperature before addition of 10 mL of anhydrous ethyl ether. The resulting solid was filtered to yield 82 mg (59%) of the HCl salt of $N^\epsilon$-Maleoyl-α-L-lysine: $^1$H NMR ($CD_3OD$) δ 1.36-1.54 (2 H, m, $CH_2$), 1.65 (2 H, q, J=7.2 Hz, $CH_2$), 1.83-2.02 (2 H, m, $CH_2$), 1.44 (9H, s, Boc), 3.53 (2H, t, J=6.9 Hz, $NCH_2$), 3.95 (1H, t, 6.2 Hz, CH), 6.82 (2H, s, maleimide); $^{13}$C NMR ($CD_3OD$) δ 23.17, 29.03, 31.01, 37.96, 135.26, 172.34, 175.20.

Example 4

$^{5K}$mPEG-amide-Lys($N^\epsilon$-maleoyl)-COOH (Compound 4)

To a solution of $^{5K}$mPEGCOONHS (805 mg, 0.16 mmol, 1 eq) in 8 mL of anhydrous DCM was added $N^\epsilon$-maleoyl-α-L-lysine (3, 82 mg, 0.31 mmol, 2 eq) in 2 mL of DMF followed by DIEA (109 µL, 0.62 mmol, 4 eq). The reaction mixture was stirred at room temperature overnight, filtered and evaporated under vacuum. The residue was first precipitated with DCM/ether and then, recrystallized with $CH_3CN$/IPA. $^{13}$C NMR ($CDCl_3$): δ 22.53, 28.02, 31.69, 37.32, 51.18, 58.86, 70.11-71.73 (PEG), 133.84, 169.51, 170.38, 172.41.

Example 5

$^{5K}$mPEG-amide-Lys($N^\epsilon$-maleoyl)-NHS (Compound 5)

$^{5K}$mPEG-Lys($N^\epsilon$-maleoyl)-COOH (4) and NHS in DCM at 0° C. are treated with DCC. The mixture is stirred at room temperature overnight. The solvent is evaporated under vacuum and the residue is precipitated with DCM/ether and then, recrystallized with $CH_3CN$/IPA.

Example 6

$^{5K}$mPEG-carbamate-Lys($N^\epsilon$-maleoyl)-COOH (Compound 6)

To a solution of $^{5K}$mPEGCOONHS (5 g, 0.98 mmol, 1 eq) in 45 mL of anhydrous DCM was added $N^\epsilon$-maleoyl-α-L-lysine (3, 514 mg, 1.95 mmol, 2 eq) in 5 mL of DMF followed by DIEA (0.7 mL, 3.92 mmol, 4 eq). The reaction mixture was stirred at room temperature overnight, filtered and evaporated under vacuum. The residue was first precipitated with DCM/ethyl ether and then, recrystallized with $CH_3CN$/IPA to give compound 6: $^{13}$C NMR δ 22.30, 28.01, 31.89, 37.29, 53.26, 58.89, 64.06, 69.31-71.77 (PEG), 133.87, 155.60, 170.42, 172.82.

Example 7

$^{5K}$mPEG-carbamate-Lys($N^\epsilon$-maleoyl)-NHS (Compound 7)

To a solution of $^{5K}$mPEG-carbamate-Lys($N^\epsilon$-maleoyl)-COOH (6, 1 g, 0.19 mmol, 1 eq) and NHS (88 mg, 0.76 mmol, 4 eq) in 10 mL of DCM at 0° C. was added DIPC (118 µL, 0.76 mmol, 4 eq). The mixture was stirred at room temperature overnight. The solvents were evaporated under vacuum and the residue was precipitated with DCM/ether and then, recrystallized with $CH_3CN$/IPA to give compound 7: $^{13}$C NMR δ 22.31, 25.90, 28.25, 32.39, 37.44, 52.42, 59.30, 64.92, 69.64-72.18 (PEG), 134.25, 155.59, 167.75, 168.55, 170.91.

Example 8

Compound 8

To a solution of 5'extGS (5 mg, 0.85 µmol) in PBS buffer (2.5 mL, pH 7.8) was added compound 7 (92 mg, 17 µmol, 20 eq) and the mixture was stirred at room temperature for 2 hours. The reaction mixture was diluted to 10 mL with water, filtered and loaded on a Poros HQ, strong anion exchange column (10 mm×1.5 mm, bed volume ~16 mL) which was pre-equilibrated with 20 mM Tris-HCl buffer, pH 7.0 (buffer A). The column was washed with 3-4 column volumes of buffer A to remove the excess PEG linker. Then the product was eluted with a gradient of 0 to 100% 1 M NaCl in 20 mM Tris-HCl buffer, pH 7.0, buffer B in 10 minutes, followed by 100% buffer B for 10 minutes at a flow rate of 10 mL/min. The eluted product was desalted using HiPrep desalting column (50 mL) and lyophilized to give compound 8 (1 mg oligo equivalent, 40% yield).

Example 9

Compound 9

To a solution of compound 8 (1 mg oligo equivalent) in PBS buffer (1 mL, pH 7.0) was added peptide cRGDfC (1 mg, 1.7 µmol) and the mixture was stirred at room temperature for 2 hours. The reaction mixture was diluted to 20 mL with water and loaded on a Poros HQ, strong anion exchange column (10 mm×1.5 mm, bed volume ~16 mL) which was pre-equilibrated with 20 mM Tris-HCl buffer, pH 7.0 (buffer A). The column was washed with 3-4 column volumes of buffer A to remove the excess PEG linker. Then the product was eluted with a gradient of 0 to 100% 1 M NaCl in 20 mM Tris-HCl buffer, pH 7.0, buffer B in 10 minutes, followed by 100% buffer B for 10 minutes at a flow rate of 10 mL/min. The eluted product was desalted using HiPrep desalting column (50 mL) and lyophilized to give compound 9 (0.78 mg oligo equivalent, 78% yield).

Example 10

Compound 10

To a solution of p-amino-benzylalcohol (1 g, 8.12 mmol, 1 eq) in 80 mL of anhydrous THF were added DIEA (1.4 mL, 8.12 mmol, 1 eq) and Boc$_2$O (1.9 mL, 8.12 mmol, 1 eq). The mixture was heated to reflux overnight, then cooled down and evaporated under vacuum. The residue was dissolved in EtOAc. The organic layer was washed with a 0.1 N HCl solution, dried over MgSO$_4$, filtered and evaporated under vacuum. The crude product was purified by column chromatography on silica gel (Hex-EtOAc, 1:1, v/v) to give 1.85 g of product (quantitative yield): $^1$H NMR δ 0.1.49 (9H, s), 2.17 (1H, s), 4.53 (2H, s), 6.83 (1H, s), 7.19 (2H, d, J=8.5 Hz), 7.28 (2H, d, J=8.2 Hz); $^{13}$C NMR δ 28.28, 64.54, 80.37, 118.49, 127.59, 135.31, 137.46, 152.72.

Example 11

Compound 11

To a −20° C. solution of compound 10 (220 mg, 0.98 mmol, 1 eq) and DIEA (188 µL, 1.08 mmol, 1.1 eq) in 8 mL of anhydrous DCM was added dropwise a solution of MsCl (84 µL, 1.08 mmol, 1.1 eq) in 2 mL of anhydrous DCM. The mixture was allowed to warm to rt and then stirred for 1 hour. The reaction mixture was washed with a saturated NaHCO$_3$ solution, a saturated NH$_4$Cl solution and brine, dried over MgSO$_4$, filtered and evaporated under vacuum. The crude compound was used in the next step without further purification.

Example 12

Compound 12

To compound 11 (0.98 mmol, 2 eq) dissolved in 15 mL of anhydrous DMF were added SN38 (192 mg, 0.49 mmol, 1 eq) and K$_2$CO$_3$ (68 mg, 0.49 mmol, 1 eq). The reaction mixture was warmed to 60° C. using a pre-heated oil bath. After 2 h, HPLC showed complete disappearance of SN38 and formation of major product. The reaction mixture was evaporated under vacuum and the residue redissolved in EtOAc and washed with water, saturated NH$_4$Cl and brine, dried over MgSO$_4$, filtered and evaporated under vacuum. The crude product was purified by column chromatography on silica gel (CH$_2$Cl$_2$-EtOAc, 1:1, v/v) to give 140 mg of product (48% yield): $^1$H NMR (DMSO-d$_6$) δ 0.88 (3H, t, J=7.0 Hz), 1.27 (3H, t, J=7.3 Hz), 1.47 (9H, s), 1.85-1.88 (2H, m), 3.15-3.17 (2H, m), 5.25 (2H, s), 5.26 (2H, s), 5.42 (2H, s), 6.49 (1H, s), 7.26 (1H, s), 7.41-7.56 (6H, m), 8.05 (1H, d, J=9.1 Hz), 9.39 (1H, s); $^{13}$C NMR (DMSO-d$_6$) δ 7.65, 13.31, 22.09, 27.96, 30.11, 49.31, 65.05, 69.47, 72.17, 78.84, 95.74, 103.39, 117.71, 117.92, 122.35, 127.44, 127.99, 128.43, 129.59, 131.07, 139.07, 143.46, 144.06, 145.92, 149.21, 149.69, 152.37, 156.46, 156.82, 172.11.

Example 13

Compound 13

A 15% (v/v) TFA in DCM solution was added to compound 12 (535 mg) and the mixture was stirred at room temperature for 1 h or until HPLC showed complete disappearance of the starting material. Ethyl ether (200 mL) was added and the resulting solid was filtered and washed with more ether (307 mg, 58% yield).

Example 14

Compound 14

Compound 13 (48 mg, 0.1 mmol, 1 eq) and 15 (36 mg, 0.1 mmol, 1 eq) were treated with EEDQ (48 mg, 0.2 mmol, 2 eq). The mixture was stirred in the dark at room temperature overnight. The solvents were removed under vacuum and the resulting solid residue was triturated with 10 mL of ethyl ether. The solid was filtered and purified by column chromatography on silica gel (CHCl$_3$:MeOH, 15:1 to 9.1) to give the desired product (8 mg, 9% yield): $^{13}$C NMR (DMSO-d$_6$) δ 7.8, 13.49, 18.11, 18.17, 18.58, 19.13, 19.25, 22.25, 26.51, 26.72, 28.19, 29.59, 30.26, 30.41, 30.50, 49.49, 51.67, 51.80, 52.90, 55.98, 59.26, 59.67, 63.03, 65.21, 69.54, 72.33, 77.91, 78.01, 95.92, 103.63, 118.10, 118.95, 122.52, 127.63, 128.21, 128.58, 131.17, 131.27, 138.53, 143.69, 144.25, 146.10, 149.43, 149.86, 155.15, 155.26, 156.63, 156.97, 158.48, 158.66, 170.39, 171.15, 171.33, 172.15, 172.29.

Example 15

Boc-Val-Cit-OH (Compound 15)

Boc-Val-NHS (10 g, 31.81 mmol, 1 eq) in 80 mL of DME was added to a solution of L-citrulline (5.85 g, 33.40 mmol, 1.05 eq) in 20 mL of THF and NaHCO$_3$ (2.8 g, 33.40 mmol, 1.05 eq) in 80 mL of water. The mixture was stirred at room temperature overnight. Aqueous citric acid (200 mL of a 15% solution in water) was added and the mixture was extracted with 10% IPA/EtOAc (2×200 mL). The suspension was washed with water (2×200 mL) and the solvent was evaporated under vacuum. The resulting solid was triturated with 200 mL of ethyl ether and filtered to yield the product (6.08 g, 51% yield): $^1$H NMR (CD$_3$OD) δ 0.92 (3H, d, J=6.7 Hz), 0.97 (3H, d, J=6.7 Hz), 1.44 (9H, s), 1.51-2.06 (5H, m), 3.12 (2H, t, J=6.7 Hz), 3.90 (1H, d, J=7.0 Hz), 4.37-4.41 (1H, m). $^{13}$C NMR (CD$_3$OD): δ 18.58, 19.83, 27.58, 28.75, 30.03, 32.09, 40.48, 53.33, 61.38, 80.49, 157.75, 162.05, 174.30, 174.69.

Example 16

Compound 16 (Boc-Val-Cit-PAB)

Boc-Val-Cit (1 g. 2.67 mmol, 1 eq) and p-aminobenzyl alcohol (362 mg, 2.94 mmol, 1.1 eq) in 2:1 DCM/MeOH (26 mL/13 mL) were treated with EEDQ (1.32 g, 5.34 mmol, 2 eq). The mixture was stirred in the dark at room temperature overnight. The solvents were removed under vacuum and the resulting solid residue was triturated with 10 mL of ethyl ether. The solid was collected by filtration and washed with ethyl ether to yield the product (900 mg, 70%): $^1$H NMR (CD$_3$OD) δ 0.93 (3H, d, J=7.0 Hz), 0.97 (3H, d, J=7.0 Hz), 1.44 (9H, s), 1.49-2.06 (5H, m), 3.07-3.29 (2H, m), 3.91 (1H, d, J=6.7 Hz), 4.50-4.55 (3H, m), 7.29 (2H, d, J=8.5 Hz), 7.54 (2H, d, J=8.5 Hz), 8.22 (1H, d, J=7.3 Hz); $^{13}$C NMR (CD$_3$OD) δ 18.64, 19.85, 27.84, 28.75, 30.61, 31.92, 40.28, 54.90, 54.99, 61.73, 64.78, 80.62, 121.09, 128.44, 138.47, 138.55, 158.01, 162.11, 172.00, 174.42, 174.52.

Example 17

Compound 14 (Boc-Val-Cit-PABE-SN38)

To a suspension of Boc-Val-Cit-PAB (214 mg, 0.45 mmol, 1 eq) in 3 mL of CH$_3$CN was added DIEA (0.23 mL, 1.35 mmol, 3 eq) followed by dropwise addition of a solution of MsCl (0.1 mL, 1.35 mmol, 3 eq) in 1 mL CH$_3$CN. After 1 hour, TLC showed no starting material left (CHCl$_3$-MeOH, 5:1, v/v). The reaction mixture was evaporated under vacuum and the resulting residue was dissolved in EtOAc. The organic phase was washed with saturated NH$_4$Cl, saturated NaHCO$_3$ and brine; dried over MgSO$_4$, filtered and evaporated under vacuum. To the crude residue dissolved in 5 mL of DMF were added SN38 (88 mg, 0.22 mmol, 0.5 eq) and K$_2$CO$_3$ (31 mg, 0.22 eq, 0.5 eq) and the mixture was heated at 60° C. for 3 hours. The product formation was monitored and conformed to product prepared in Example 14 by HPLC.

Example 18

Compound 17

Compound 14 in DCM is treated with 2N HCl in ether. After completion of the reaction additional ether is added and the resulting solid is filtered and washed with ether to give Val-Cit-PABE-SN38. To a solution of compound 5 in anhydrous DCM is added HCl.Val-Cit-PABE-SN38 in anhydrous DMF followed by DIEA. The mixture is stirred at room temperature overnight. The solvent is removed under vacuum and the resulting solid is precipitated with DCM/ether and recrystallized with CH$_3$CN/IPA to give the product.

Example 19

Compound 18

To a solution of compound 17 (1 eq) in a mixture of DCM/DMF is added RGDC (2 eq). The reaction mixture is stirred at room temperature overnight and then the solvent is evaporated under vacuum. The residue is precipitated with DCM/ethyl ether and recrystallized with DMF/IPA to give the product.

Example 20

Compound 19

To a solution of $^{20k}$4armPEGSC (7 g, 0.35 mmol, 1 eq) in 60 mL of anhydrous DCM was added Lys(Boc)-OH (690 mg, 2.8 mmol, 2 eq) in 15 mL of DMF followed by DIEA (1 mL, 5.6 mmol, 4 eq). The reaction mixture was stirred at room temperature overnight, filtered and evaporated under vacuum. The residue was first precipitated with DCM/ethyl ether and recrystallized with CH$_3$CN/IPA to give compound 19: $^{13}$C NMR δ 21.88, 27.97, 29.04, 31.57, 39.60, 44.98, 53.00, 63.44, 68.86-70.37 (PEG), 78.04, 155.26, 172.89.

Example 21

Compound 20

To a solution of 4arm-PEG-Lys(Boc)-OH in 25 mL of anhydrous DCM was added a 4N HCl solution in dioxane (25 mL). The reaction was starred at room temperature for 4 hours and then was evaporated under vacuum. The residue was precipitated by addition of ethyl ether. The solid was filtered and washed with ether to give 4arm-PEG-Lys-OH (1.77 g): $^{13}$C NMR δ 21.97, 26.54, 31.22, 39.63, 45.11, 53.16, 63.66, 69.88-70.51 (PEG), 78.04, 155.59, 172.78.

Example 22

Compound 21

A solution of BocCys(NPys)-OH (300 mg, 0.80 mmol, 1 eq) and NHS (97 mg, 0.84 mmol, 1.05 eq) in 10 mL of anhydrous DCM at 0° C. was treated with DCC (173 mg, 0.84 mmol, 1.05 eq). The mixture was allowed to warm to room temperature and stirred overnight. The solid DCU byproduct was filtered off. To the filtrate was added compound 20 (1.7 g, 0.082 mmol, 1 eq) followed by DIEA (114 µL, 0.66 mmol, 8 eq). The reaction mixture was stirred at room temperature overnight and evaporated under vacuum. The residue was first precipitated with DCM/ether and then, recrystallized with CH$_3$CN/IPA to give the compound 21 (1.5 g): $^{13}$C NMR δ 22.32, 25.52, 28.27, 28.83, 31.90, 39.03, 42.45, 45.38, 53.41, 53.58, 63.91, 64.37, 69.30-72.38 (PEG), 80.11, 120.98, 133.94, 142.54, 153.34, 155.51, 155.71, 157.28, 169.98, 173.32.

Example 23

Compound 22

To a solution of compound 21 (1.5 g, 0.07 mmol, 1 eq) and NHS (125 mg, 1.09 mmol, 16 eq) in 15 mL of DCM at 0° C. was added DIPC (168 µL, 1.09 mmol, 16 eq). The mixture was stirred at room temperature overnight. The solvents were evaporated under vacuum and the residue was precipitated with DCM/ether and then, recrystallized with CH$_3$CN/IPA to give the product (1.3 g): $^{13}$C NMR δ 22.05, 25.76, 25.93, 28.68, 28.92, 32.01, 38.89, 42.49, 45.79, 52.40, 53.97, 64.78, 69.57-71.77 (PEG), 80.47, 121.32, 134.29, 142.93, 153.75, 155.71, 157.60, 168.18, 169.14, 169.71, 170.56.

Example 24

Compound 23

(BocPheLys(Fmoc)-OH). To a solution of BocPheOSu (1.5 g, 4.14 mmol, 1 eq) in DCM (10.3 mL) and DMF (10.3 mL) was added H-Lys(Fmoc)-OH (1.84 g, 4.55 mmol, 1.1 eq) followed by DIEA (2.9 mL, 16.56 mmol, 4 eq). The resulting reaction mixture was stirred overnight and diluted with ethyl acetate. The solution was washed with water (30 mL×2) and by brine (30 mL×2). The organic layers were combined, dried over $MgSO_4$ and concentrated in vacuo to yield a yellow residue. The crude residue was then chromatographed over silica gel using $CHCl_3$-MeOH (3:1, v/v) to give the product. MS. $[M+1]^+$ 616.

Example 25

Compound 24

Compound 13 (111 mg, 0.22 mmol, 1 eq) and 16 (208 mg, 0.34 mmol, 1.5 eq) were treated with EEDQ (167 mg, 0.67 mmol, 3 eq). The mixture was stirred in the dark at room temperature overnight. The solvents were removed under vacuum and the resulting solid residue was triturated with 10 mL of ethyl ether. The solid was filtered and purified by column chromatography on silica gel ($CH_2Cl_2$-EtOAc, 1:1 to 1:2, v/v) to give the desired product (20 mg, 8% yield). MS. $[M+1]^+$ 1095.

Example 26

Compound 25

Compound 24 (8 eq) is treated with 4N HCl in dioxane. The reaction is stirred at room temperature for 4 hours. Ethyl ether is added and the solid is filtered. This solid is dissolved in DMF and added to a solution of compound 22 (1 eq) in DCM. To the mixture is added DIEA (16 eq) and the reaction is stirred at room temperature overnight. The solvent is removed under vacuum and the resulting solid is precipitated with DCM/ethyl ether and recrystallized with DMF/IPA to give the product.

Example 27

Compound 26

To a solution of compound 25 in DCM is added piperidine. The reaction mixture is stirred for 4 hours. The solvent is removed under vacuum and the resulting solid is precipitated with DCM/ethyl ether and recrystallized with DMF/IPA to give the product.

Example 28

Compound 27

To a solution of compound 26 (1 eq) in a mixture of DCM/DMF is added RGDC (2 eq). The reaction mixture is stirred at room temperature overnight and then the solvent is evaporated under vacuum. The residue is precipitated with DCM/ethyl ether and recrystallized with DMF/IPA to give the product.

Example 29

FmocVal-Cit-OH (Compound 28)

Fmoc-Val-NHS (2.5 g, 5.73 mmol, 1 eq) in 15 mL of DME was added to a solution of L-citrulline (1.05 g, 6.01 mmol, 1.05 eq) in 8 mL of THF and $NaHCO_3$ (505 mg, 6.01 mmol, 1.05 eq) in 15 mL of water. The mixture was stirred at room temperature overnight. Aqueous citric acid (75 mL of a 15% solution in water) was added and the mixture was extracted with 10% IPA/EtOAc (2×100 mL). The organic layers were washed with water (3×100 mL) and the solvent was evaporated under vacuum. The resulting solid was triturated with 100 mL of ethyl ether and filtered to yield the product (1.98 g, 70% yield): $^1$H NMR (DMSO-$d_6$) δ 0.86 (3H, d, J=6.7 Hz), 0.90 (3H, d, J=7.0 Hz), 1.40-1.48 (2H, m), 1.51-1.75 (2H, m), 1.98 (1H, sext, J=6.8 Hz), 2.95 (2H, q, J=6.2 Hz), 3.93 (1H, dd, J=7.3, 8.8 Hz), 4.14-4.29 (4H, m), 5.40 (2H, brs), 5.96 (1H, t, J=5.6 Hz), 7.32 (2H, t, J=7.5 Hz), 7.39-7.44 (3H, m), 7.75 (2H, t, J=6.3 Hz), 7.89 (2H, d, J=7.3 Hz), 8.19 (1H, d, J=7.3 Hz); $^{13}$C NMR (DMSO-$d_6$) δ 18.31, 19.25, 26.75, 28.40, 30.59, 46.68, 51.91, 59.81, 64.92, 65.65, 119.98, 125.30, 126.94, 127.52, 140.55, 143.61, 143.76, 155.88, 158.58, 171.12, 173.25.

Example 30

FmocVal-Cit-PAB (Compound 29)

A solution of compound 28 (1 g, 2.01 mmol, 1 eq) and p-aminobenzyl alcohol (273 mg, 2.21 mmol, 1.1 eq) in a mixture of DCM/MeOH (20 mL/10 mL) was treated with EEDQ (996 mg, 4.03 mmol, 2 eq). The mixture was stirred in the dark at room temperature overnight. The solvents were removed under vacuum and the resulting solid residue was triturated with 10 mL of ethyl ether. The solid was collected by filtration and washed with ethyl ether to yield the product (925 mg, 76% yield): $^1$H NMR (DMSO-$d_6$) δ 0.87 (6H, d, t=7.5 Hz), 1.36-1.47 (2H, m), 1.51-1.75 (2H, m), 1.99 (1H, sext, J=6.7 Hz), 2.90-3.04 (3H, m), 3.93 (1H, dd, J=7.3, 8.8 Hz), 4.23-4.38 (4H, m), 4.43 (2H, d, J=5.3 Hz), 5.13 (1H, t, J=5.6 Hz), 5.43 (2H, brs), 5.99 (1H, t, J=5.6 Hz), 7.23 (2H, d, J=8.5 Hz), 7.32 (2H, t, J=7.3 Hz), 7.39-7.48 (3H, m), 7.54 (2H, d, J=8.5 Hz), 7.74 (2H, t, J=6.7 Hz), 7.89 (2H, d, J=7.6 Hz), 8.12 (1H, d, J=7.3 Hz); $^{13}$C NMR (DMSO-$d_6$) δ 18.34, 19.28, 26.84, 29.56, 30.47, 46.67, 53.05, 60.05, 62.55, 65.65, 118.71, 119.98, 125.23, 126.79, 126.94, 127.51, 137.27, 137.36, 140.55, 143.60, 143.73, 155.93, 158.69, 170.17, 171.06.

Example 31

Val-Cit-PAB (Compound 30)

To a solution of compound 29 (622 mg, 1.03 mmol) in 10 mL of anhydrous DMF was added piperidine (2 mL). The mixture was stirred at room temperature overnight and then the solvents were evaporated under vacuum. The residue was triturated with DCM and the resulting solid was filtered and washed with DCM to give the product (283 mg, 72% yield): $^1$H NMR (DMSO-$d_6$) δ 0.79 (3H, d, J=6.7 Hz), 0.89 (3H, d, J=6.7 Hz), 1.38-1.42 (2H, m), 1.52-1.68 (2H, m), 1.94 (1H, sext, J=6.3 Hz), 2.89-3.01 (2H, m), 3.05 (1H, d, J=4.7 Hz), 4.46 (2H, s), 5.09 (1H, brs), 5.40 (2H, s), 5.98 (1H, t, J=5.3 Hz), 7.23 (2H, d, J=8.2 Hz), 7.54 (2H, d, J=8.5 Hz), 8.14 (1H, brs), 10.03 (1H, s); $^{13}$C NMR (DMSO-$d_6$) δ 16.80, 19.33, 26.53, 29.95, 31.10, 52.31, 59.33, 62.35, 118.61, 126.59, 137.06, 137.14, 158.44, 170.06, 173.69.

Example 32

Compound 31

To a solution of compound 22 (1.3 g, 0.06 mmol, 1 eq) in 15 mL of anhydrous DCM and 3 mL anhydrous DMF was added compound 30 (175 mg, 0.46 mmol, 8 eq). The reaction mixture was stirred overnight at room temperature and then the solvent was evaporated under vacuum. The residue was first precipitated with DCM/ether and then, recrystallized with CH$_3$CN/IPA to give the product (1.1 g): $^{13}$C NMR (CDCl$_3$/CD$_3$OD) δ 18.48, 19.46, 22.85, 26.74, 28.54, 28.94, 29.50, 30.47, 31.81, 39.21, 42.04, 45.79, 53.51, 54.06, 55.32, 59.67, 64.32, 65.04, 69.54-70.99 (PEG), 80.70, 120.23, 121.44, 127.64, 134.31, 137.16, 142.94, 153.86, 155.86, 156.85, 160.44, 170.45, 171.02, 171.87, 173.19.

Example 33

Compound 32

To a solution compound 31 (1 eq) in a mixture of DCM/DMF (4/1, v/v) is added DSC (16 eq) and the mixture is cooled to 0° C. Then, pyridine (16 eq) is added and the mixture is gradually warmed to room temperature and stirred overnight. The solvent is evaporated under vacuum and the residue is precipitated with DCM/ethyl ether and then, recrystallized with CH$_3$CN/IPA to give the product.

Example 34

Compound 33

To a solution of compound 32 is added doxorubicin. The reaction mixture is stirred at rt overnight. The solvent is evaporated under vacuum and the residue is precipitated with DCM/ethyl ether and then, recrystallized with DMF/IPA to give the product.

Example 35

Compound 34

To a solution of compound 33 (1 eq) in a mixture of DCM/DMF is added RGDC (2 eq). The reaction mixture is stirred at room temperature overnight and then the solvent is evaporated under vacuum. The residue is precipitated with DCM/ethyl ether and recrystallized with DMF/IPA to give the product.

Example 36

Compound 35

To a solution of compound 19 (6.14 g, 0.307 mmol, 1 eq) and NHS (283 mg, 2.456 mmol, 8 eq) in 31 mL of anhydrous DCM at 0° C. was added DCC (507 mg, 2.456 mmol, 2 eq). The reaction mixture was stirred at room temperature overnight, filtered over a pad of celite and evaporated under vacuum. The residue was first precipitated with DCM/ethyl ether and then, recrystallized with CH$_3$CN/IPA to give the product (5.69 g, 86%): $^{13}$C NMR δ 21.59, 25.21, 28.11, 29.03, 31.42, 39.36, 45.13, 51.80, 64.07, 68.90-70.53 (PEG), 155.15, 155.58, 168.17, 168.54.

Example 37

Compound 36

To a solution of compound 35 (5.0 g, 0.232 mmol, 1 eq) in 23 mL each of anhydrous DCM and anhydrous DMF was added HCl.NH$_2$Cys(NPys)-OH (0.77 g, 2.78 mmol, 12 eq) followed by DIEA (0.65 mL, 3.71 mmol, 16 eq). The reaction mixture was stirred at room temperature overnight and evaporated under vacuum after filtering through a pad of celite. The residue was first precipitated with DCM/ether and then, recrystallized with CH$_3$CN/IPA to give the product (4.88 g, 95% yield): $^{13}$C NMR δ 22.17, 28.22, 29.27, 31.85, 39.92, 45.22, 51.85, 54.49, 63.98, 69.06-70.62 (PEG), 78.56, 120.87, 132.88, 142.27, 153.44, 155.67, 156.47, 162.14, 170.74, 171.20.

Example 38

Compound 37

To a solution of compound 36 (4.38 g, 0.197 mmol, 1 eq) in DCM (44 mL) was added 8.8 mL of TFA and the reaction mixture was allowed to stir overnight at room temperature. After 20 reaction mixture was evaporated under vacuum and the residue was first precipitated with DCM/ether and then, recrystallized with CH$_3$CN/IPA to give the product (2.1 g, 49%): $^{13}$C NMR δ 21.47, 26.41, 31.64, 39.47, 45.25, 52.32, 54.11, 63.75, 69.12-70.65 (PEG), 120.85, 133.46, 142.25, 153.67, 155.64, 156.39, 171.53, 171.79.

Example 39

Compound 38

To a solution of folic acid (124 mg, 0.28 mmol, 1 eq) in 3.1 mL of DMSO at room temperature was added NHS (71 mg, 0.616 mmol, 2.2 eq) followed by addition of DCC (64 mg, 0.308 mmol, 1.1 eq) and 63 µL of triethylamine. The reaction mixture was stirred overnight in the dark and filtered over a pad of Celite® to obtain a clear yellow solution of FA-NHS which was used as is for the next coupling step with the linker. To a solution of H$_2$N-Lys(4arm-PEG)CysNPys (37,381 mg, 0.0175 mmol, 1 eq) in 4 mL each of anhydrous DCM and anhydrous DMF was added the DMSO solution of FA-NHS (prepared as shown above) followed by DIEA (49 µL, 0.28 mmol, 16 eq). The reaction mixture was allowed to stir overnight in the dark at room temperature. It was then dialysed for 4 days with distilled water. The yellow solution was then lyophilized to obtain 197 mg of the final product.

Example 40

Compound 39

To a solution of C6-Mo-LNA-survivin (OligoSH) in pH 6.5 phosphate buffer is added compound 38 and the solution is stirred for 1 hour at room temperature. Reaction progress is checked by anion-exchange HPLC. The reaction mixture is filtered through 0.2 micron filter and loaded on Poros anion-exchange column. The product is eluted with a gradient using buffer system 20 mM Tris. HCl 2M NaCl at pH 7.0. The product is desalted and lyophilized.

We claim

1. A compound of the Formula (I)

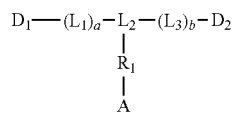

wherein:

$R_1$ is a polyalkylene oxide;

A is a capping group or

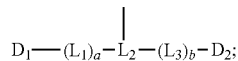

each $D_1$ is independently selected from the group consisting of targeting moieties, functional groups and leaving groups;

each $D_2$ is independently selected from the group consisting of biologically active moieties, functional groups and leaving groups;

each $L_1$ is an independently selected permanent linker selected from the group consisting of:

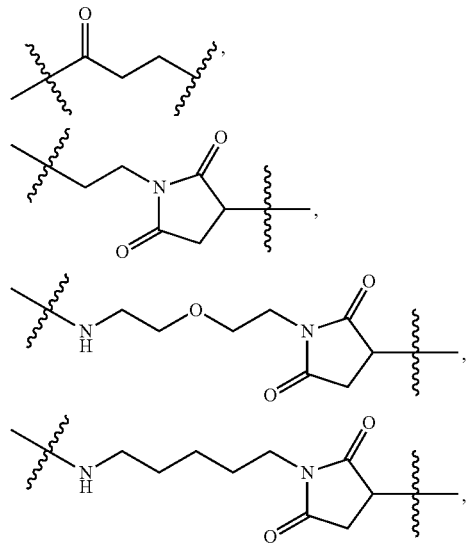

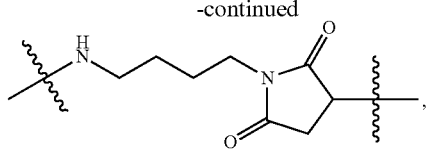

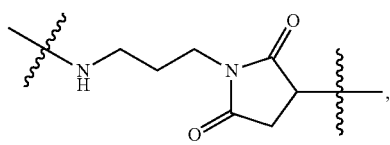

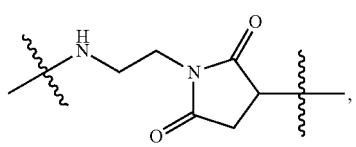

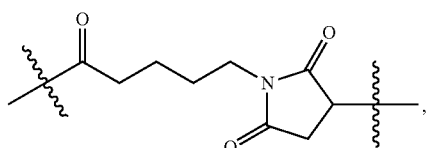

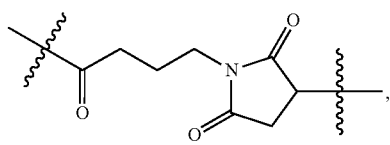

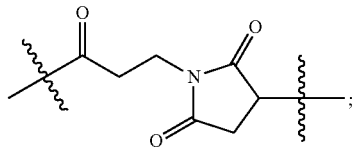

$L_2$ is a multifunctional linker is selected from the group consisting of:

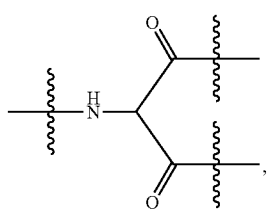

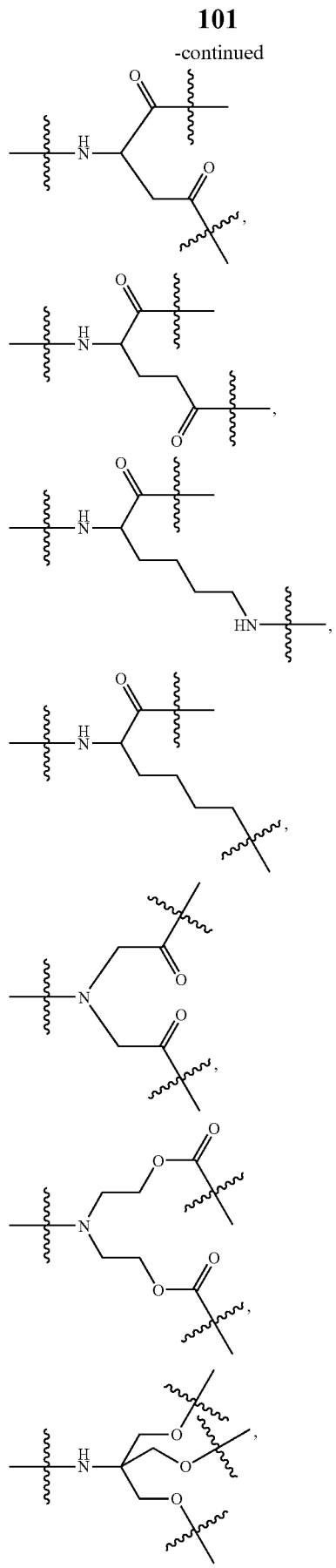

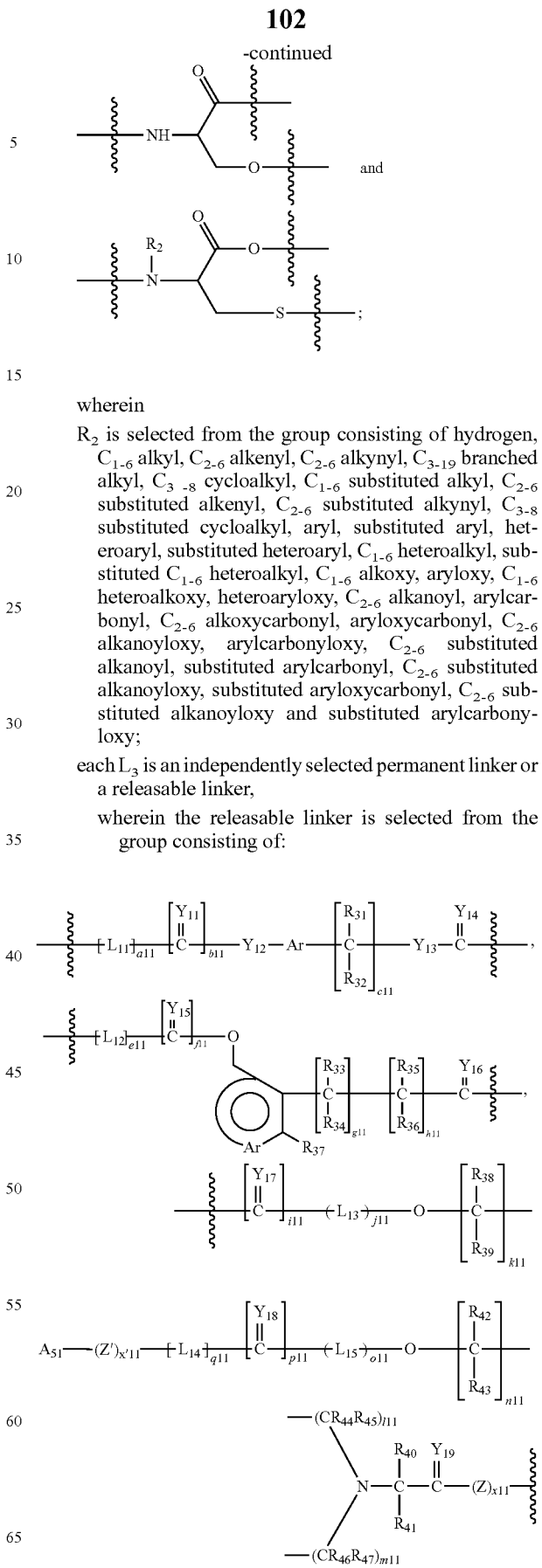

wherein

R₂ is selected from the group consisting of hydrogen, $C_{1-6}$ alkyl, $C_{2-6}$ alkenyl, $C_{2-6}$ alkynyl, $C_{3-19}$ branched alkyl, $C_{3-8}$ cycloalkyl, $C_{1-6}$ substituted alkyl, $C_{2-6}$ substituted alkenyl, $C_{2-6}$ substituted alkynyl, $C_{3-8}$ substituted cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-6}$ substituted alkanoyl, substituted arylcarbonyl, $C_{2-6}$ substituted alkanoyloxy, substituted aryloxycarbonyl, $C_{2-6}$ substituted alkanoyloxy and substituted arylcarbonyloxy;

each $L_3$ is an independently selected permanent linker or a releasable linker, wherein the releasable linker is selected from the group consisting of:

-continued

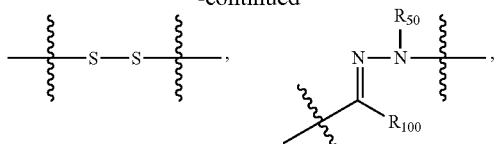

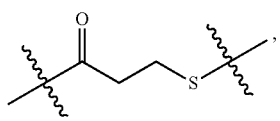

-Val-Cit-,
-Gly-Phe-Leu-Gly-,
-Ala-Leu-Ala-Leu-
-Phe-Lys-,

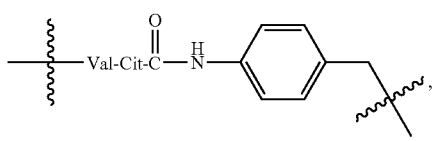

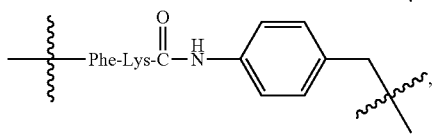

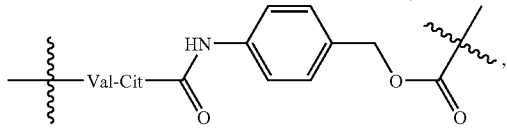

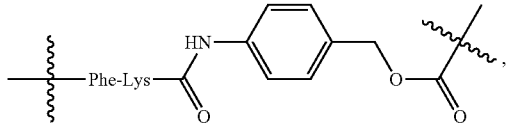

-Val-Cit-C(=O)—CH$_2$OCH$_2$—C(=O)—,
-Val-Cit-C(=O)—CH$_2$SCH$_2$—C(=O)—, and
—NHCH(CH$_3$)—C(=O)—NH(CH$_2$)$_6$—C(CH$_3$)$_2$—C(=O)—,
wherein
Y$_{11-19}$ are independently O, S or NR$_{48}$;
R$_{31-48}$, R$_{50}$, R$_{100}$ and A$_{51}$ are independently selected from the group consisting of hydrogen, C$_{1-6}$ alkyls, C$_{3-12}$ branched alkyls, C$_{3-8}$ cycloalkyls, C$_{1-6}$ substituted alkyls, C$_{3-8}$ substituted cyloalkyls, aryls, substituted aryls, aralkyls, C$_{1-6}$ heteroalkyls, substituted C$_{1-6}$ heteroalkyls, C$_{1-6}$ alkoxy, C$_{1-6}$ alkyloxycarbonyl, phenoxy and C$_{1-6}$ heteroalkoxy;
Ar is an aryl or heteroaryl moiety;
L$_{11-15}$ are independently selected bifunctional spacers;
Z and Z' are independently selected from selected from the group consisting of moieties actively transported into a target cell, hydrophobic moieties, bifunctional linking moieties and combinations thereof;
(c11), (h11), (k11), (l11), (m11) and (n11) are one;
(a11), (e11), (g11), (j11), (o11) and (q11) are independently either zero or one; and
(b11), (x11), (x'12), (f11), (i11) and (p11) are independently zero or one; and
(a) and (b) are independently zero or one.

2. A compound of claim 1, selected from the group consisting of:

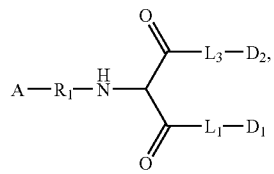

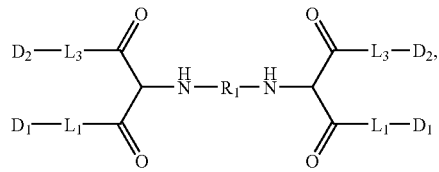

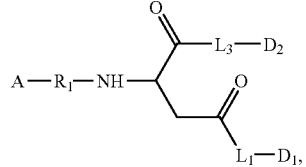

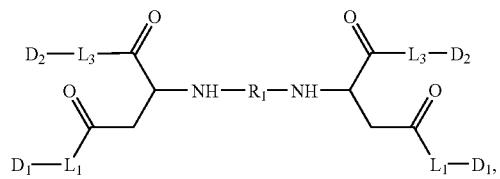

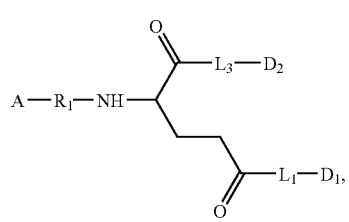

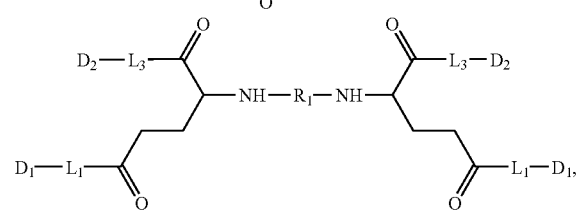

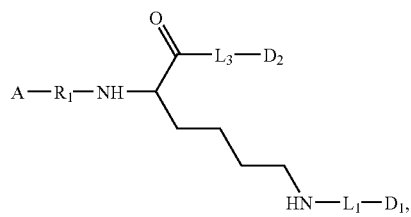

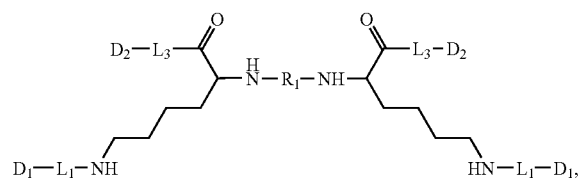

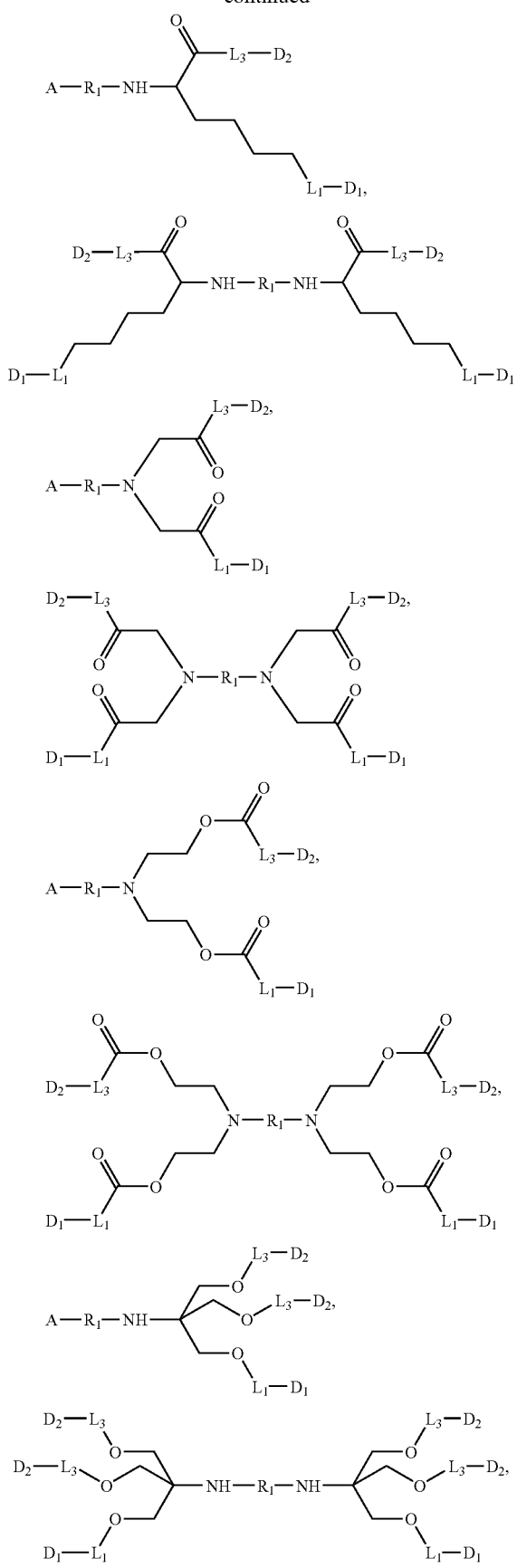
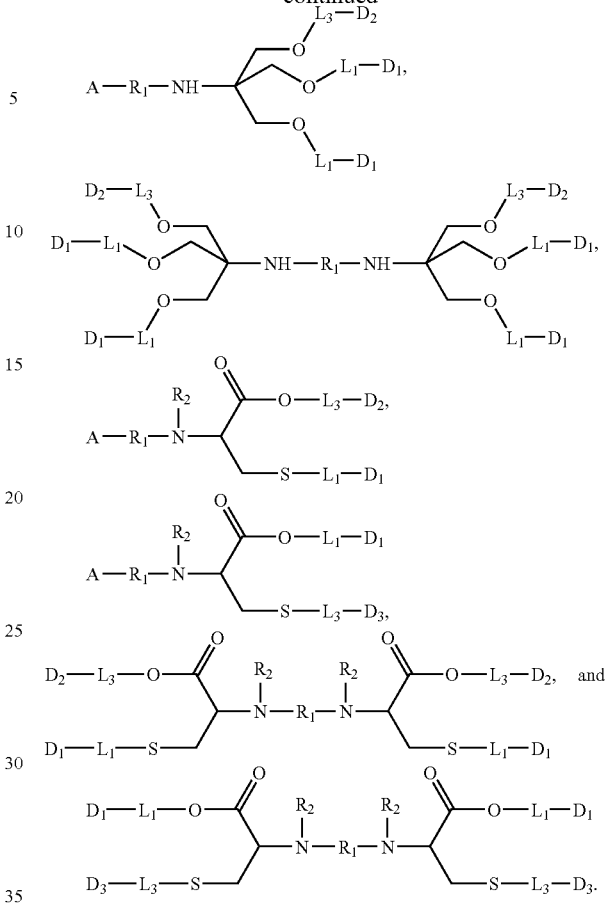

3. The compound of claim 1, wherein the biologically active moiety is selected from the group consisting of —NH$_2$ containing moieties, —OH containing moieties and —SH containing moieties.

4. The compound of claim 1, wherein the biologically active moiety is selected from the group consisting of pharmaceutically active compounds, enzymes, proteins, oligonucleotides, antibodies, monoclonal antibodies, single chain antibodies and peptides.

5. The compound of claim 4, wherein the pharmaceutically active compounds are selected from the group consisting of DNA topoisomerase inhibitors, microtubule inhibiting drugs, DNA damaging agents, antimetabolites, nucleoside analogs and anticancer drugs.

6. The compound of claim 1, wherein the biologically active moiety is an oligonucleotide.

7. The compound of claim 6, wherein the oligonucleotide is selected from the group consisting of antisense oligonucleotides, locked nucleic acids (LNA), short interfering RNA (siRNA), microRNA (miRNA), aptamers, peptide nucleic acid (PNA), and phosphorodiamidate morpholino oligonucleotides (PMO).

8. The compound of claim 6, wherein the oligonucleotide is selected from the group consisting of antisens bcl-2 oligonucleotides, antisense HIF-1α oligonucleotides, and antisense Survivin oligonucleotides.

9. The compound of claim 1, wherein the targeting agent is selected from the group consisting of monoclonal antibodies, single chain antibodies, cell adhesion peptides, cell penetrating peptides, receptor ligands, targeting carbohydrate molecules or lectins and oligonucleotide.

10. The compound of claim 1, wherein the targeting agent is selected from the group consisting of RGD peptide, selectin, TAT, penetratin, $(Arg)_9$ and folic acid.

11. The compound of claim 1, wherein the releasable linker is selected from the group consisting of benzyl elimination-based linkers, trialkyl lock-based linkers, bicine-based linkers, acid-labile linkers, lysosomally cleavable peptides and capthepsin B cleavable peptides.

12. The compound of claim 1, wherein the polyalkylene oxide is selected from the group consisting of polyethylene glycol and polypropylene glycol.

13. The compound of claim 1, wherein the polyalkylene oxide is selected from the group consisting of $-Y_{21}-(CH_2CH_2O)_n-CH_2CH_2Y_{21}-$, $-Y_{21}-(CH_2CH_2O)_n-CH_2C(=Y_{22})-Y_{21}-$, $-Y_{21}-C(=Y_{22})-(CH_2)_{a2}-Y_{23}-(CH_2CH_2O)_n-CH_2CH_2-Y_{23}-(CH_2)_{a2}-C(=Y_{22})-Y_{21}-$ and $-Y_{21}-(CR_{51}R_{52})_{a2}-Y_{23}-(CH_2)_{b2}-O-(CH_2CH_2O)_n-(CH_2)_{b2}-Y_{23}-(CR_{51}R_{52})_{a2}-Y_{21}-$, wherein:

$Y_{21}$ and $Y_{23}$ are independently O, S, SO, $SO_2$, $NR_{53}$ or a bond;

$Y_{22}$ is O, S, or $NR_{53}$;

$R_{51-53}$ are independently selected from the group for $R_2$;

(a2) and (b2) are independently zero or a positive integer; and (n) is an integer from about 10 to about 2300.

14. The compound of claim 1 wherein the polyalkylene oxide is a polyethylene glycol of the formula, $-O-(CH_2CH_2O)-$ wherein (n) is an integer from about 10 to about 2,300.

15. The compound of claim 1, wherein $R_1$ has an average molecular weight from about 2,000 to about 100,000 daltons.

16. The compound of claim 1, wherein $R_1$ has an average molecular weight of from about 5,000 to about 60,000 daltons.

17. The compound of claim 1, wherein $R_1$ has an average molecular weight from about 5,000 to about 25,000 daltons or from about 20,000 to about 45,000 daltons.

18. A compound of claim 1, selected from the group consisting of:

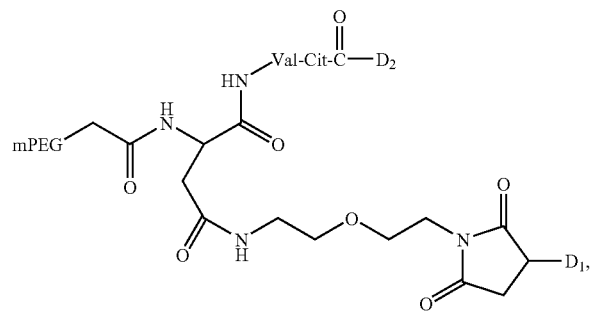

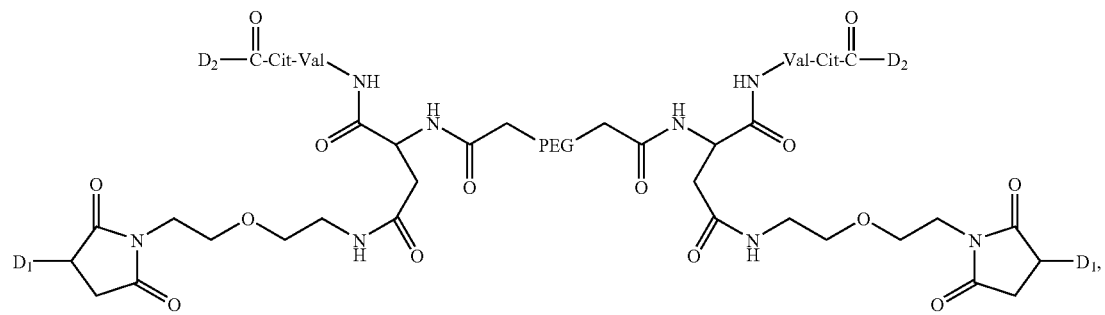

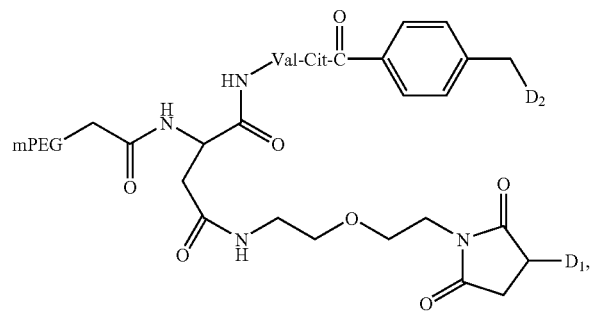

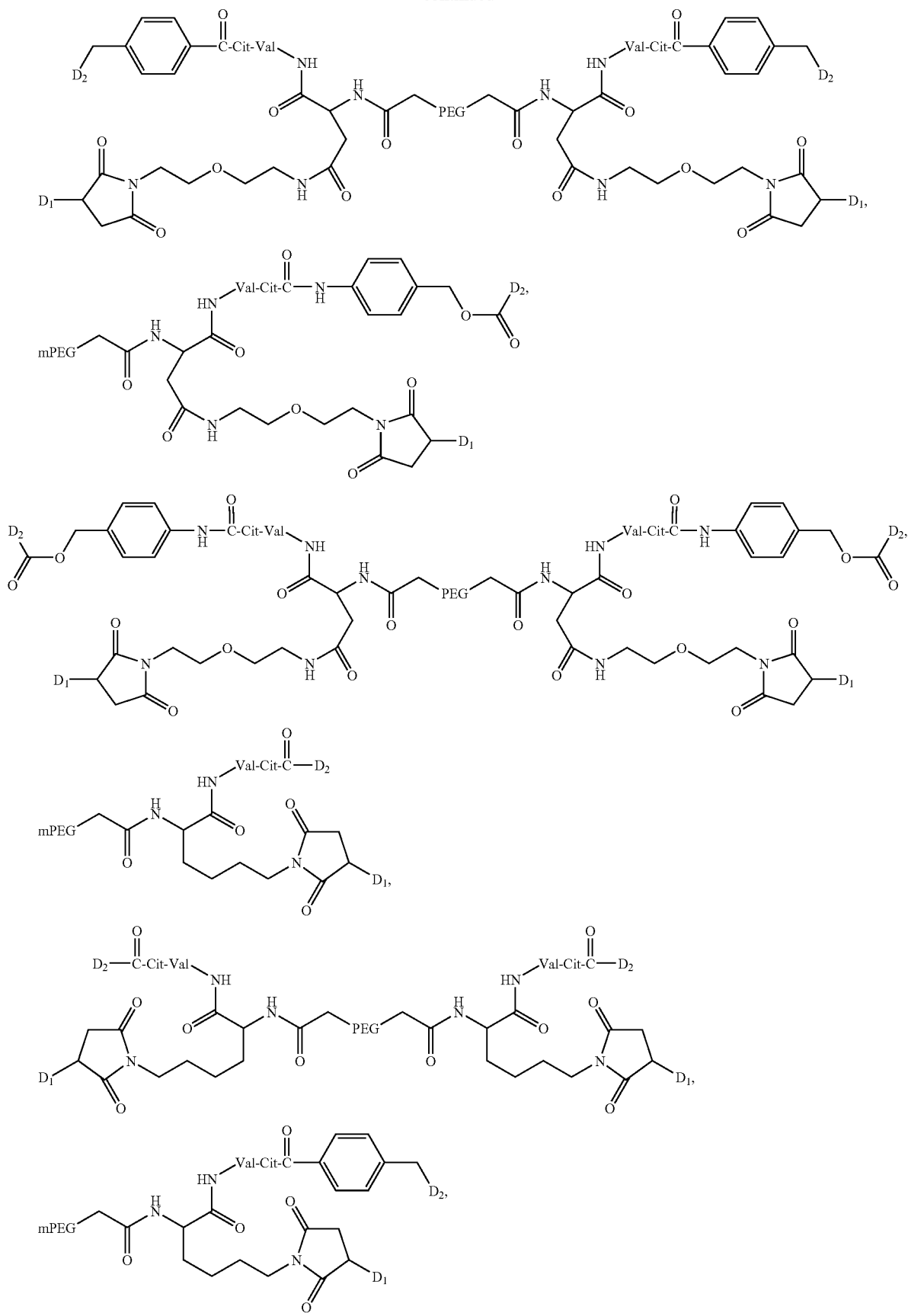

111            112
-continued
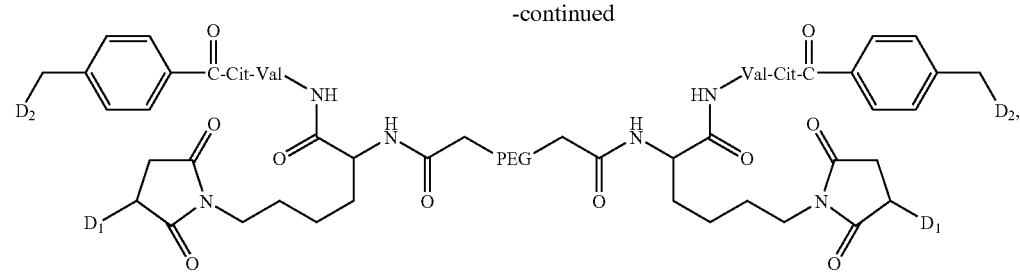
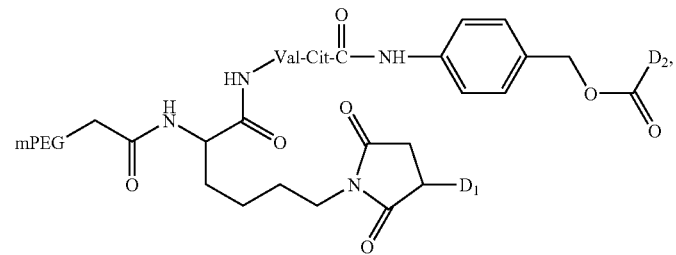
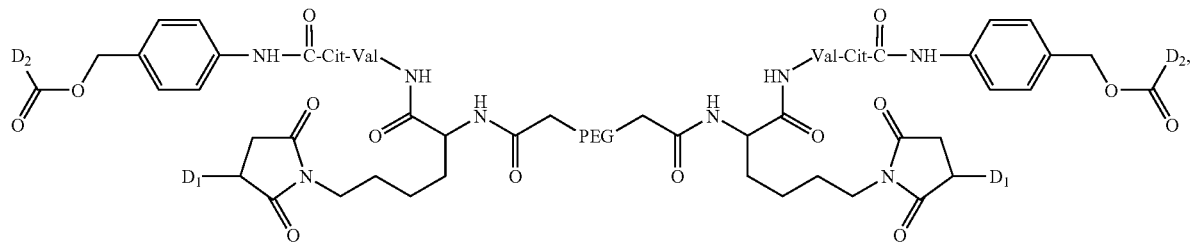
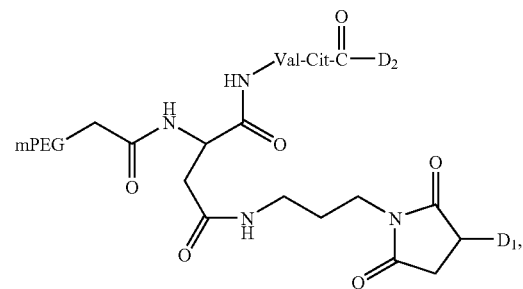
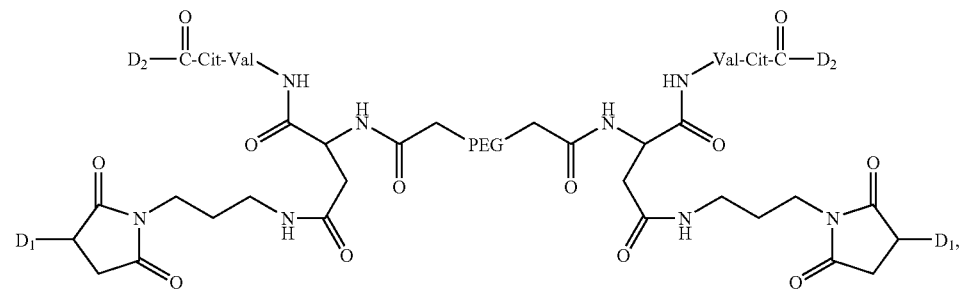
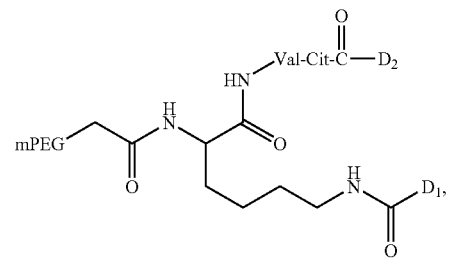

-continued
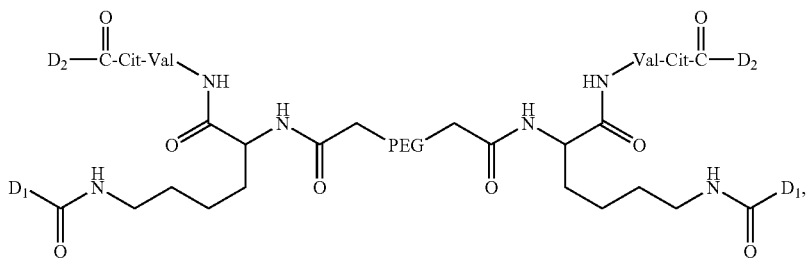
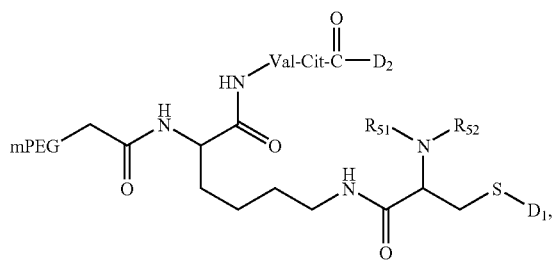
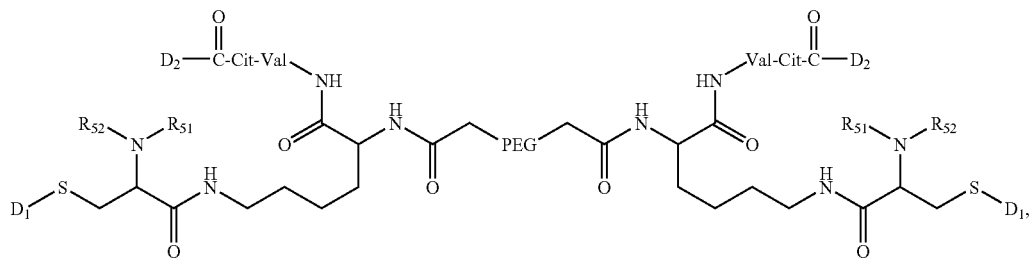
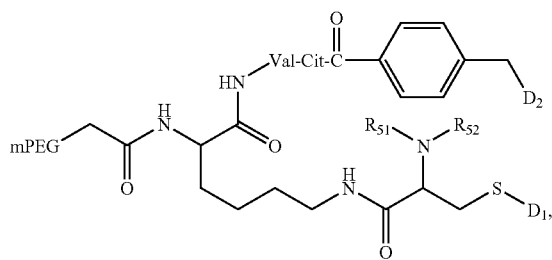
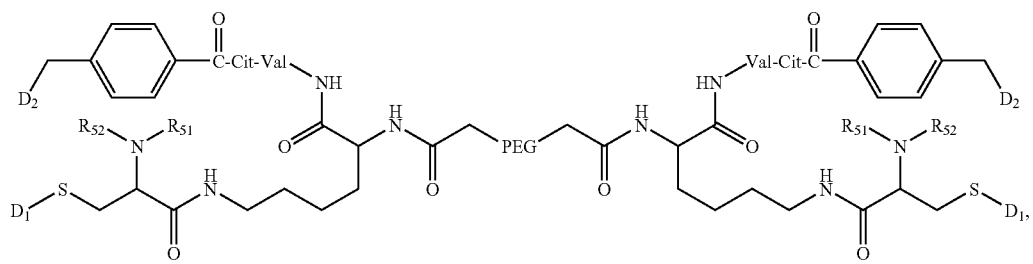
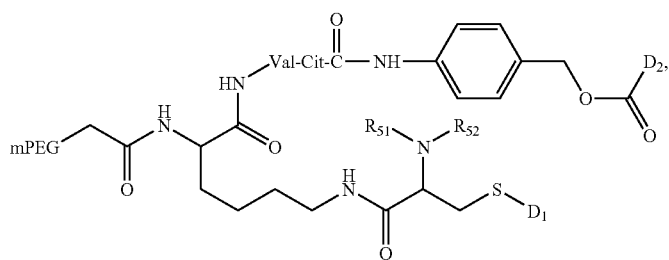

115 116
-continued
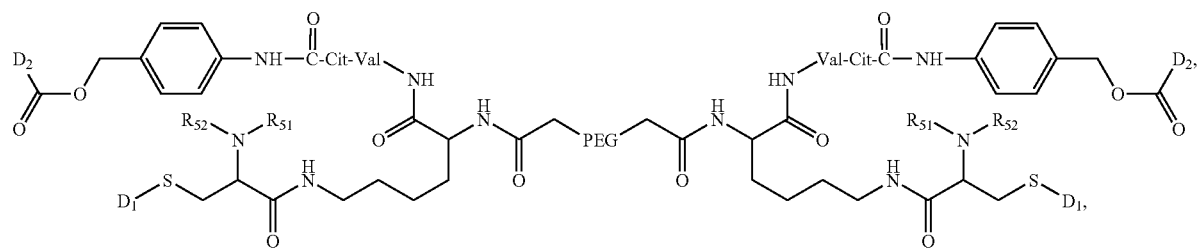
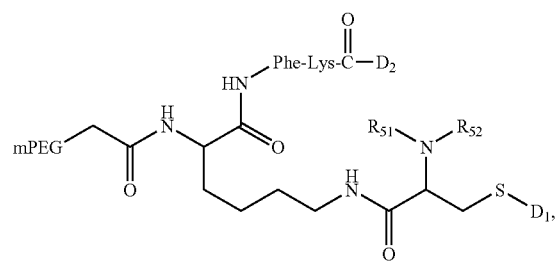
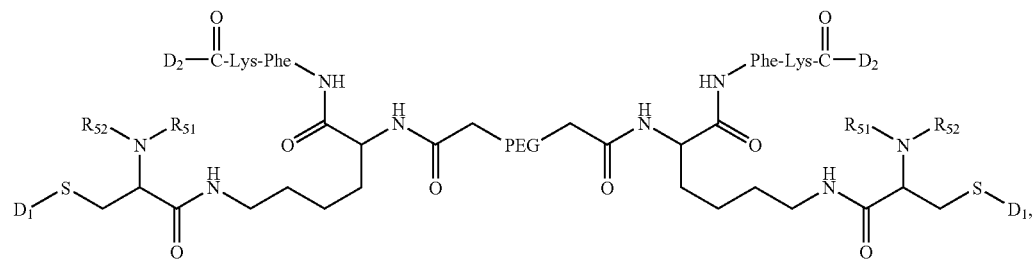
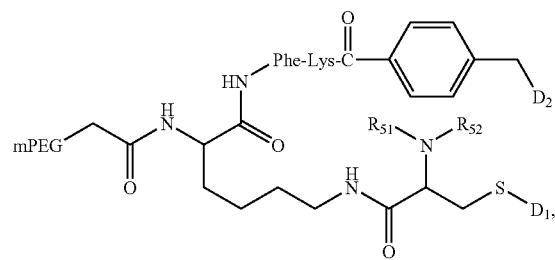
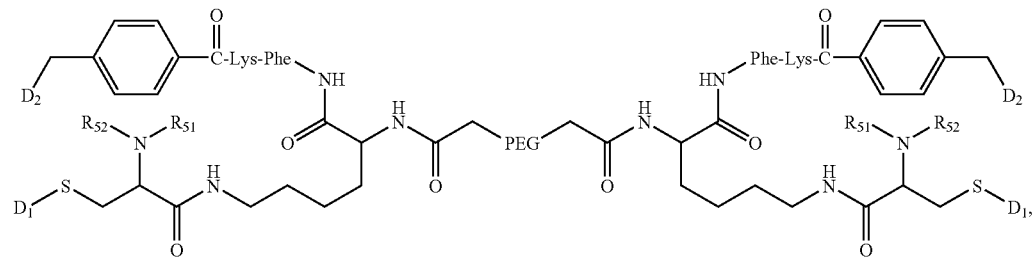
and
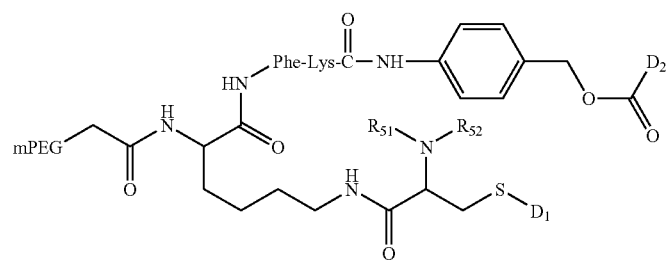

117

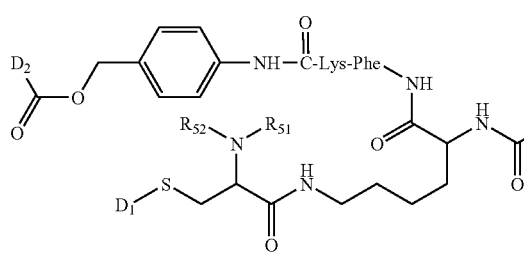

118

-continued

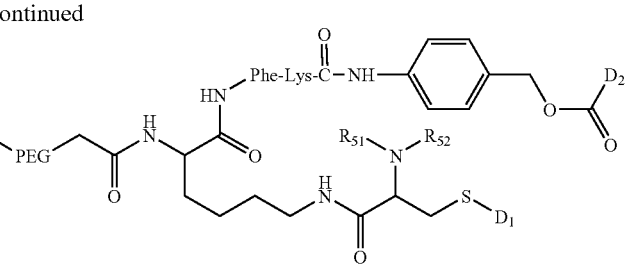

wherein
mPEG has the formula: $CH_3\text{—}O(CH_2CH_2O)_n\text{—}$;
PEG has the formula $\text{—}O(CH_2CH_2O)_n\text{—}$;
(n) is a positive integer from about 10 to about 2,300;
$R_{51}$ and $R_{52}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cyloalkyls, aryls, substituted aryls, aralkyls, $C_{1-6}$ heteroalkyls, substituted $C_{1-6}$ heteroalkyls, $C_{1-6}$ alkoxy, $C_{1-6}$ alkyloxycarbonyl, aryloxycarbonyl, phenoxy and $C_{1-6}$ heteroalkoxy;

$D_1$ is a targeting moiety, a functional group or a leaving group; and $D_2$ is a biologically active moiety, a functional group or a leaving group.

19. A compound of claim 1, selected from the group consisting of:

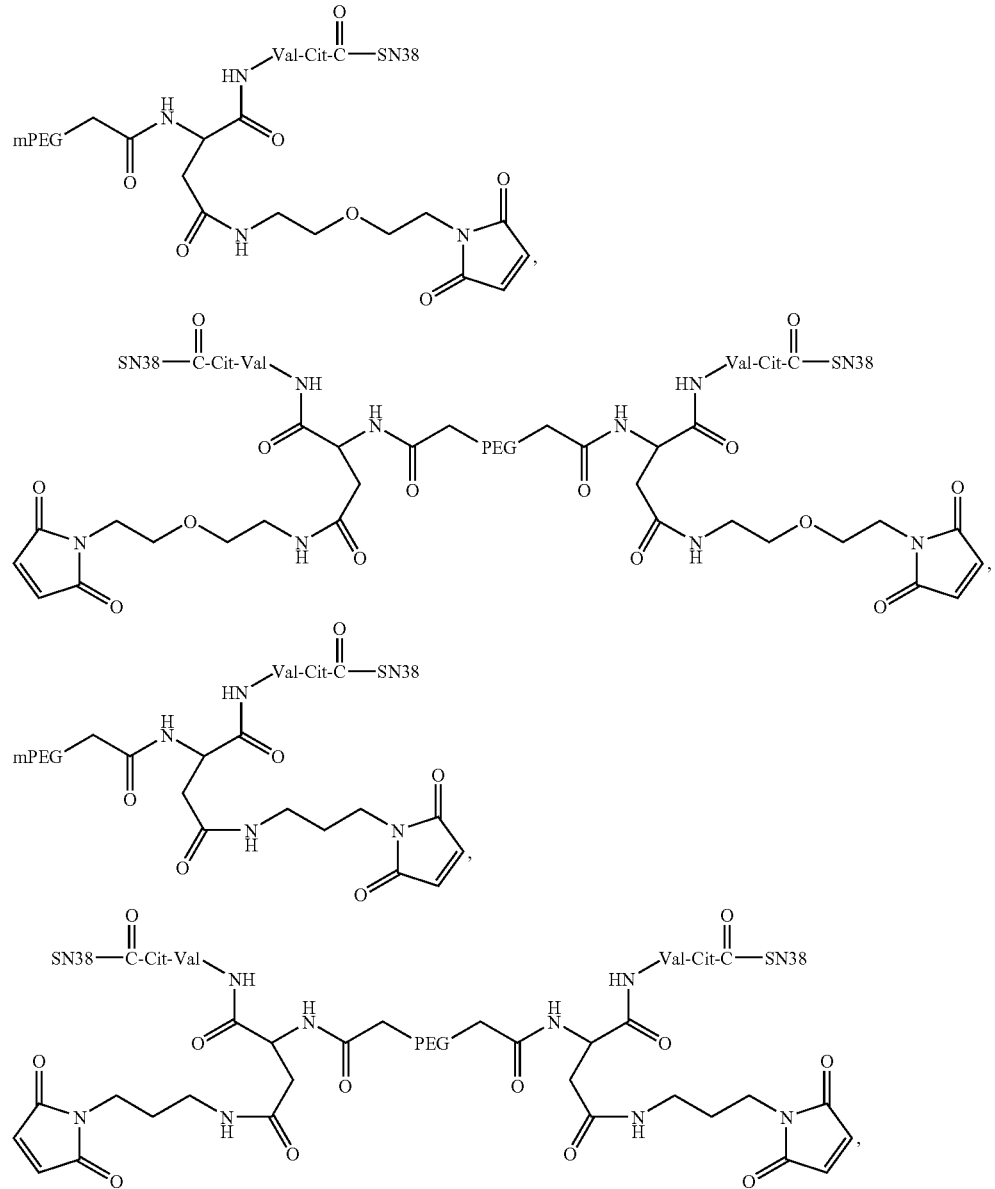

-continued
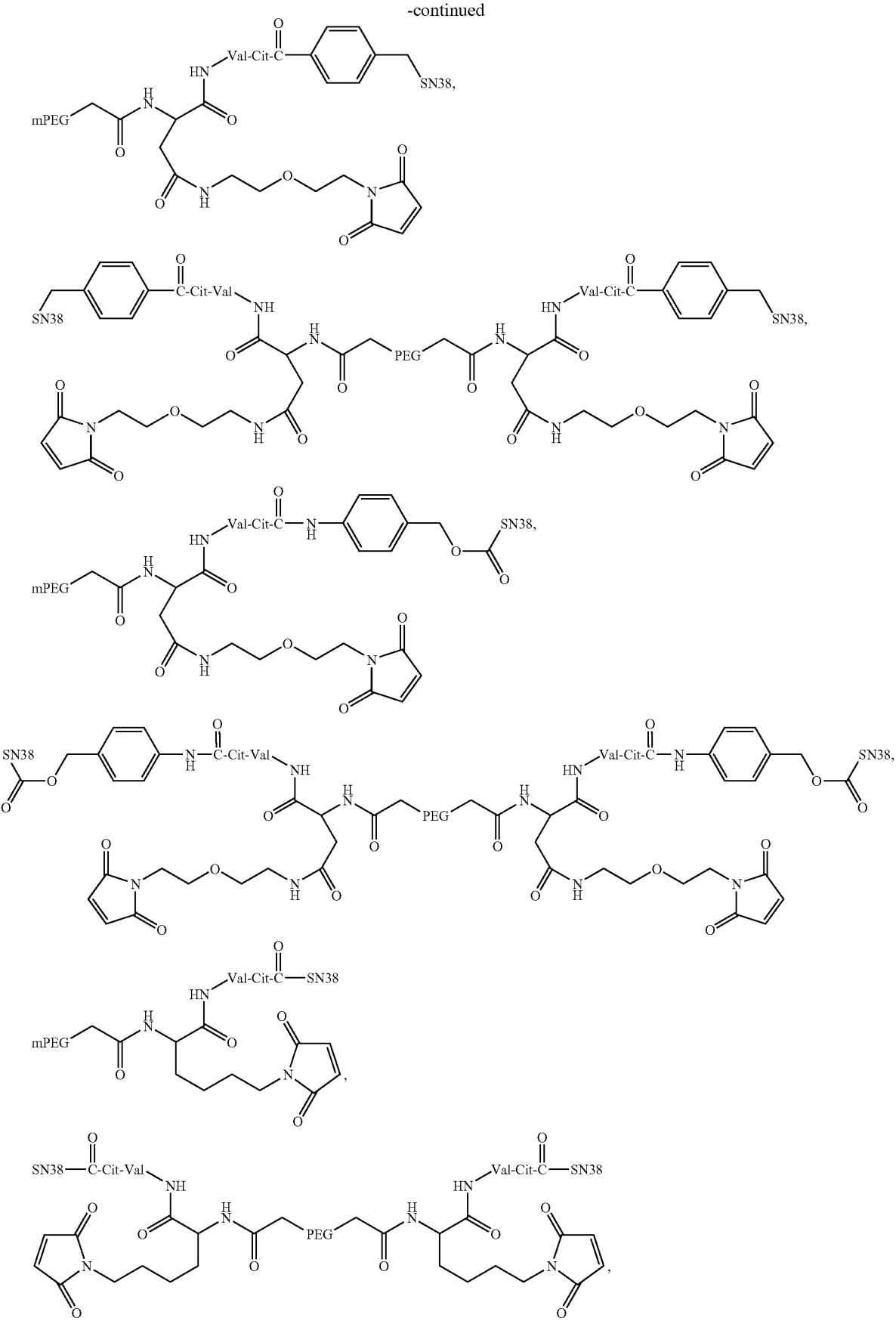

-continued
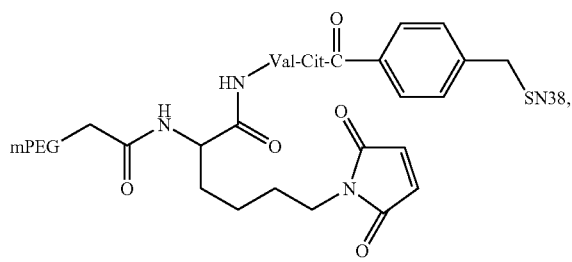
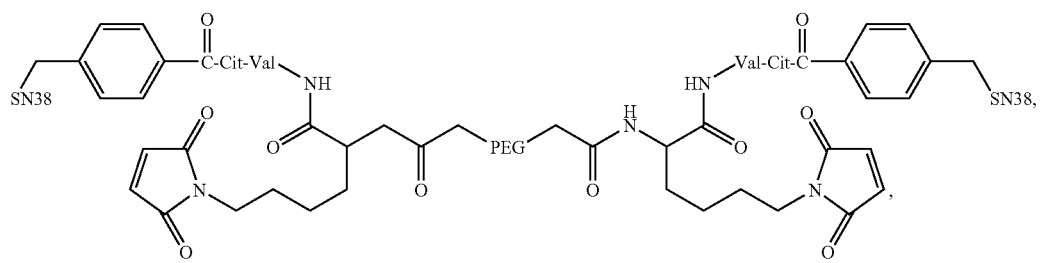
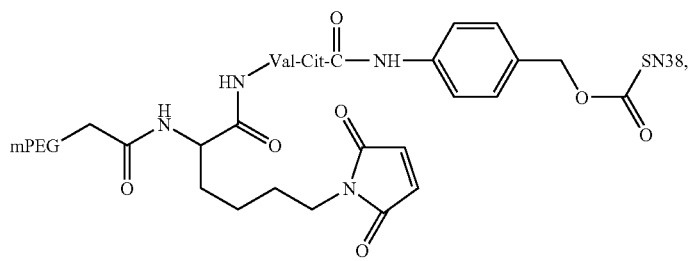
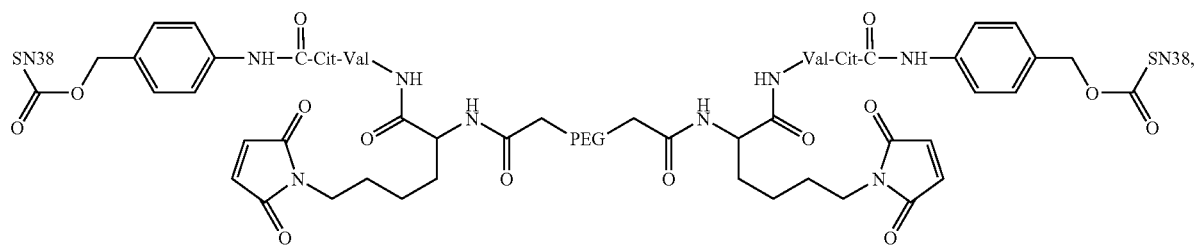
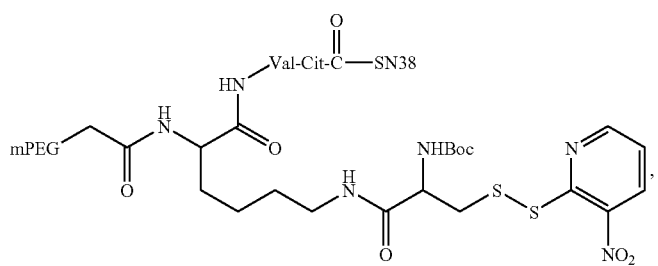
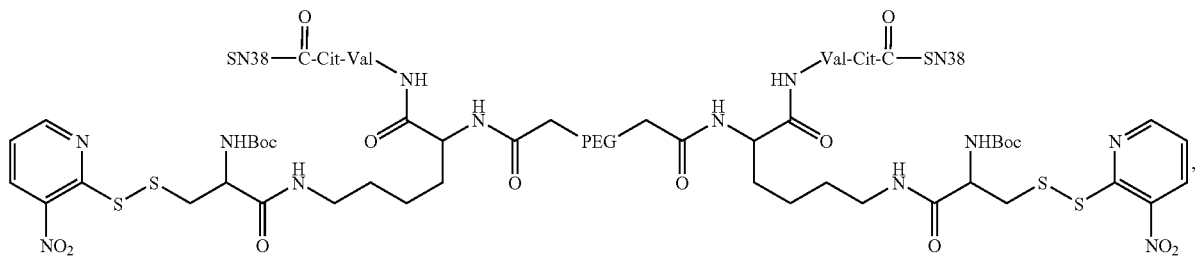

-continued
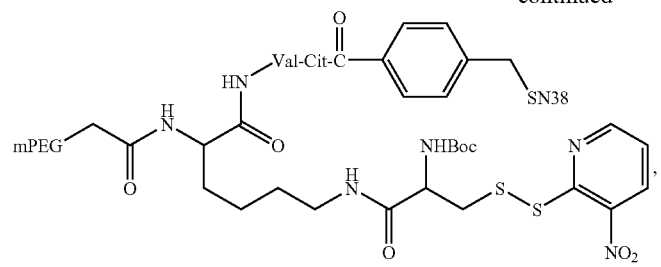
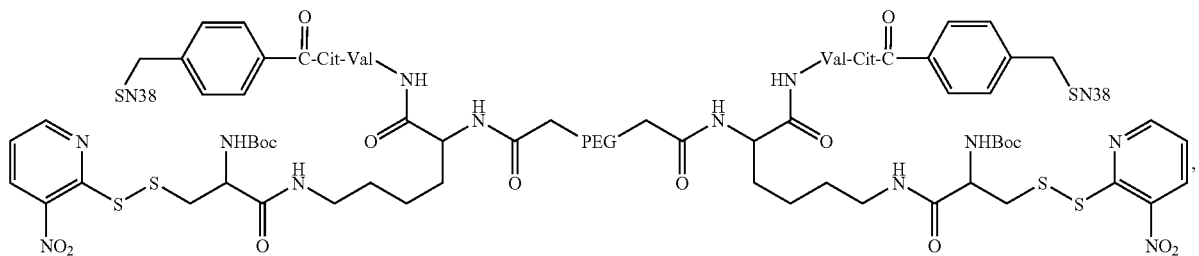
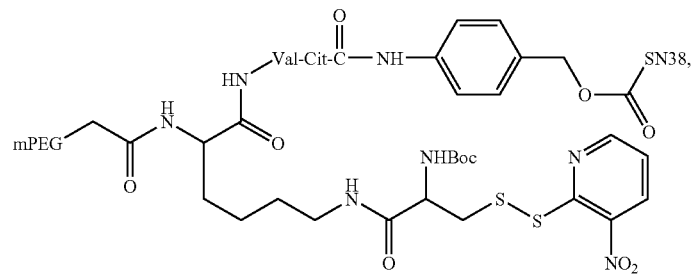
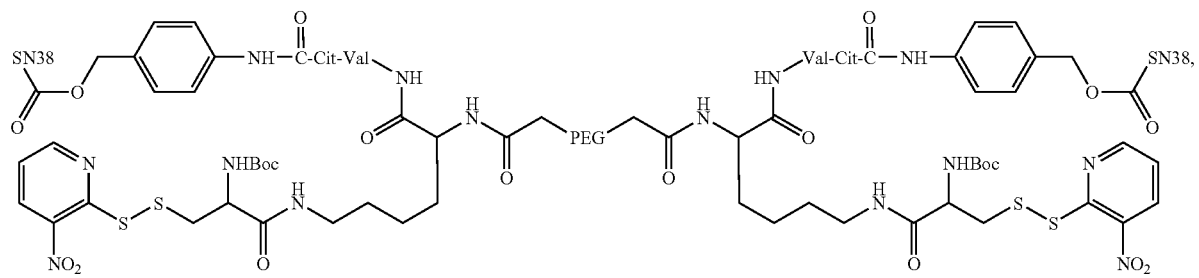
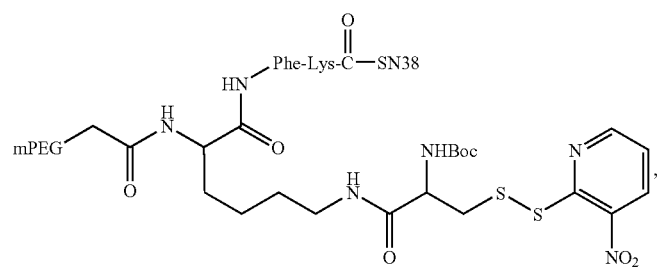
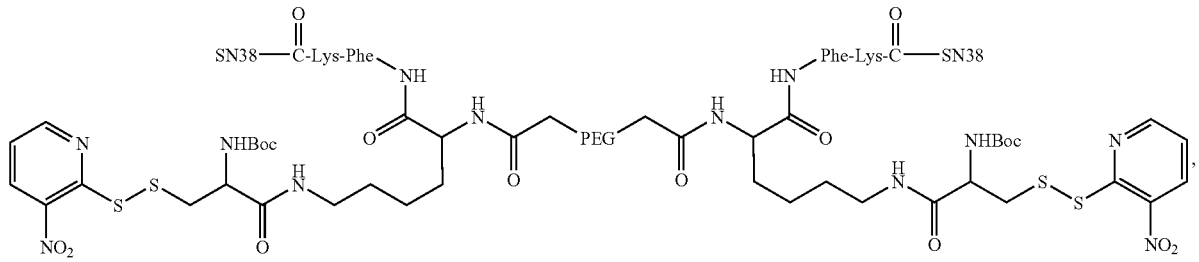

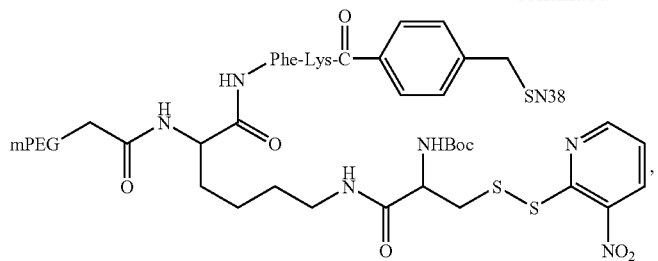
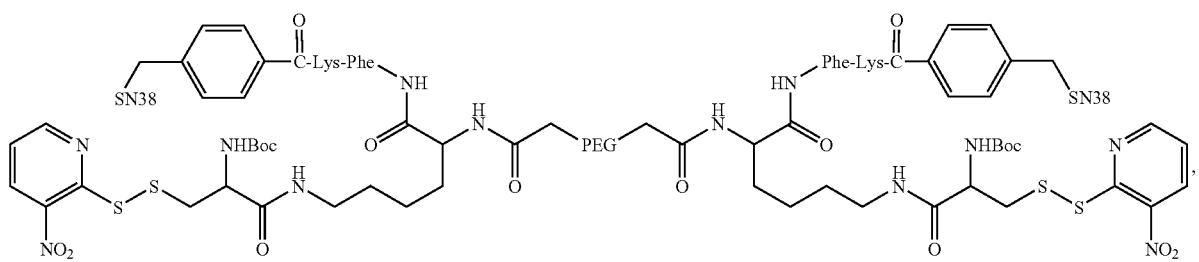
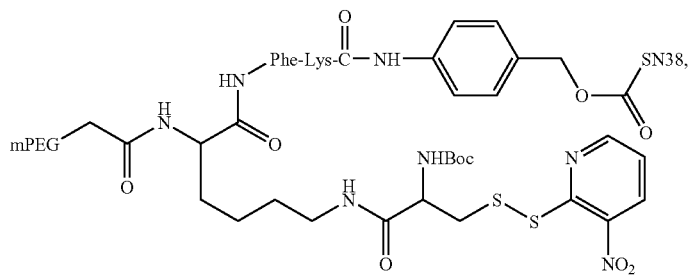
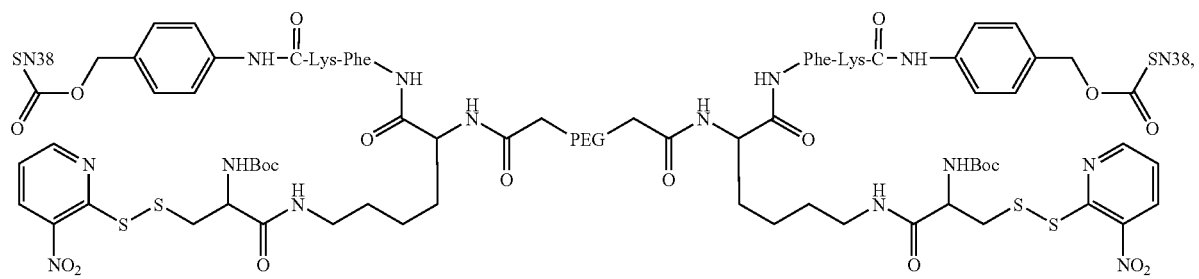
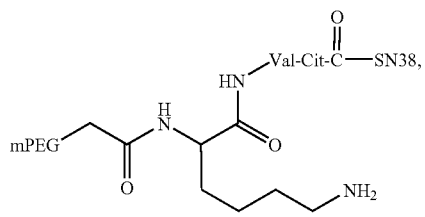
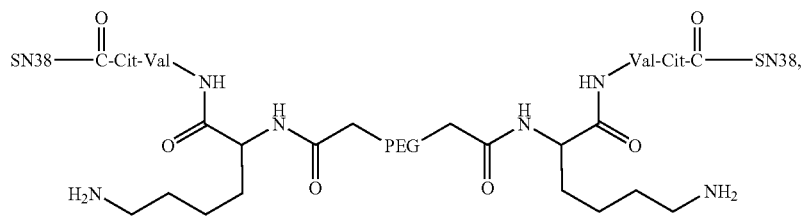

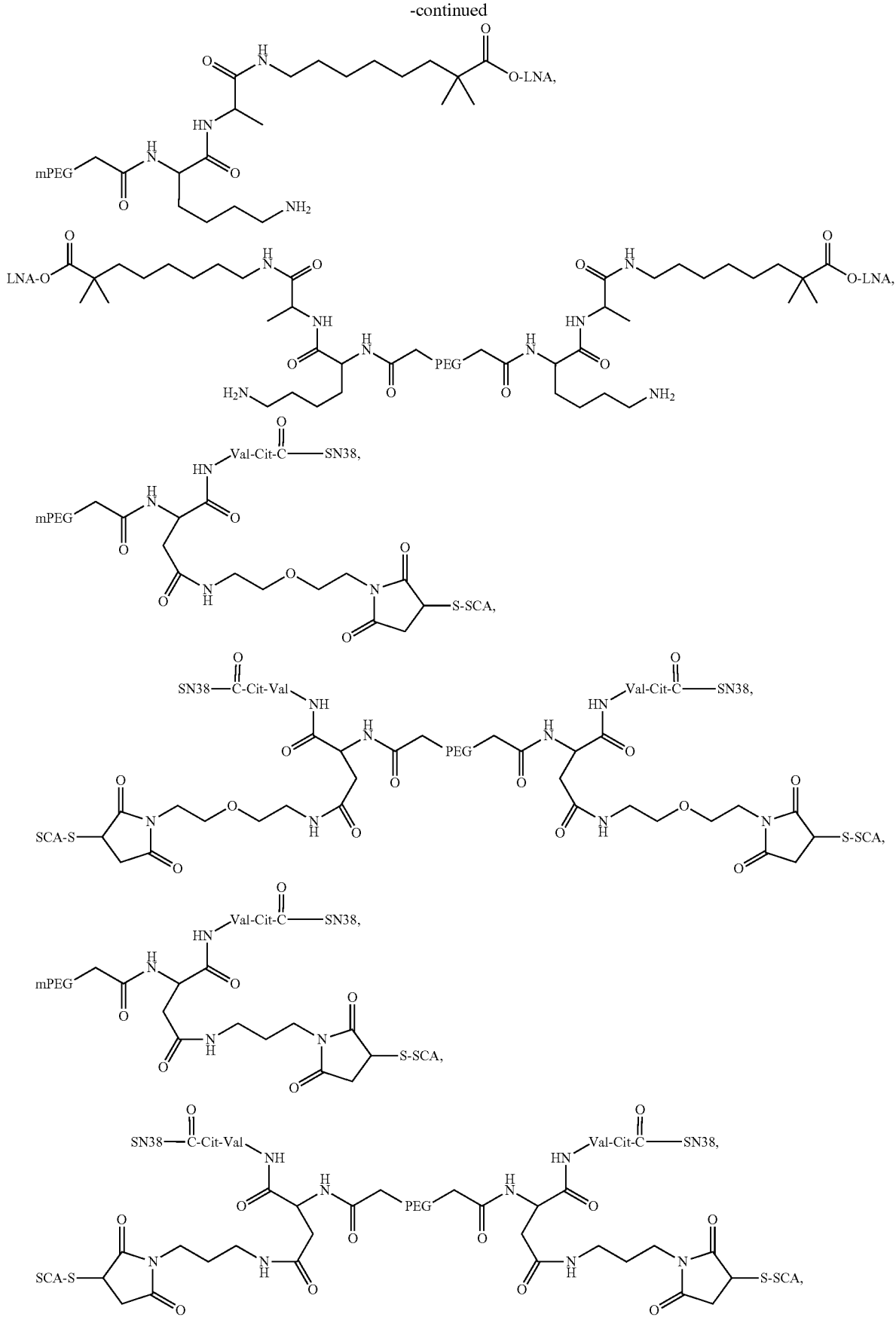

-continued
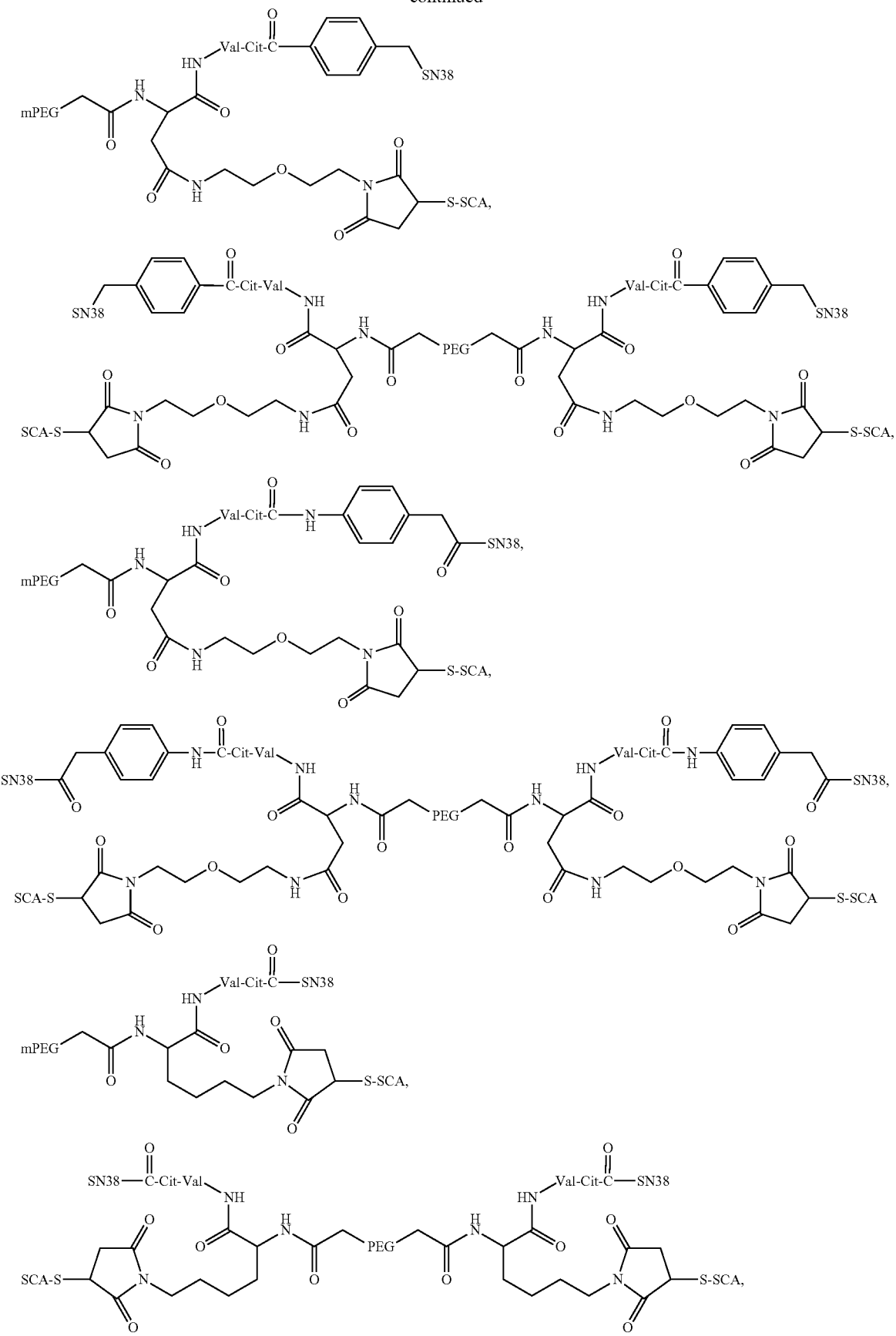

-continued
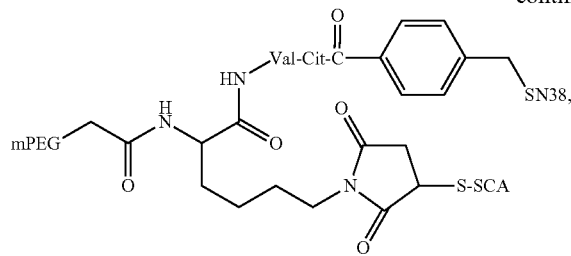
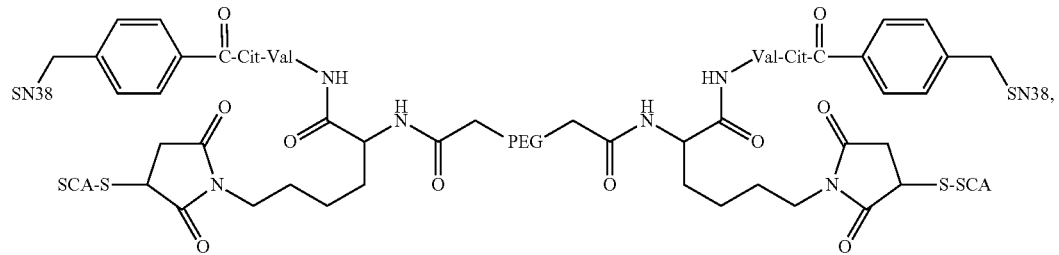
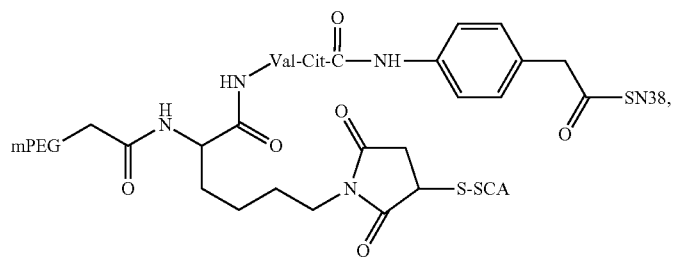
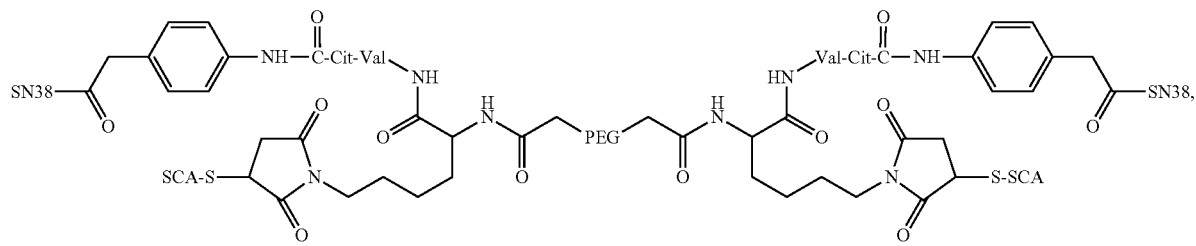
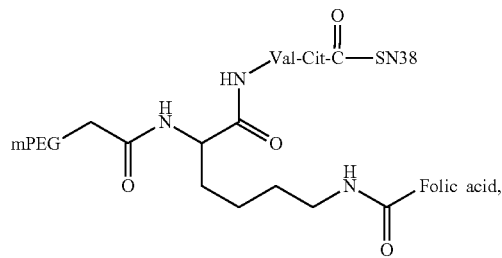
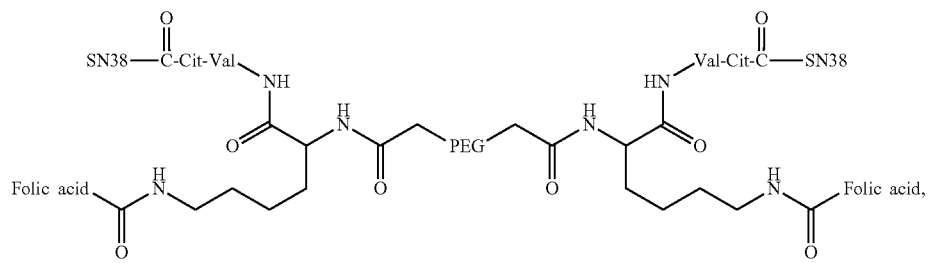

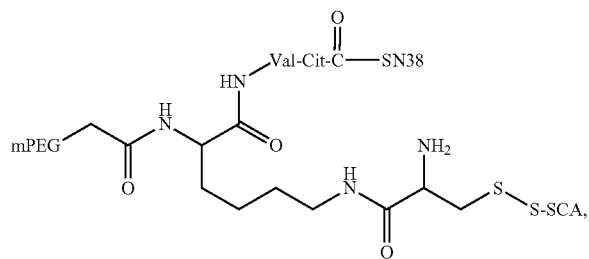
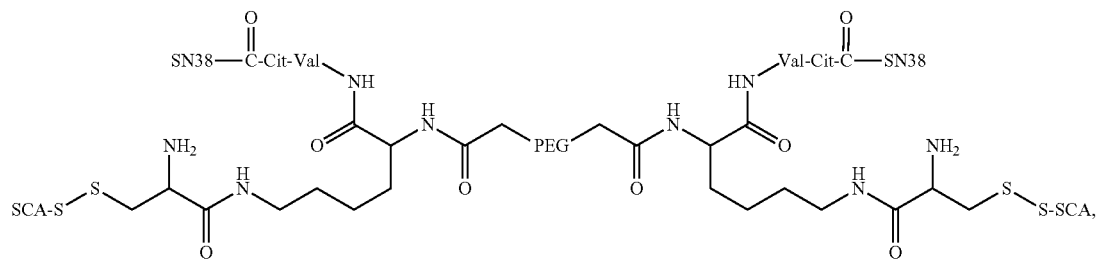
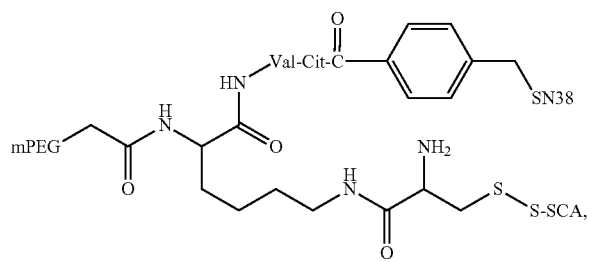
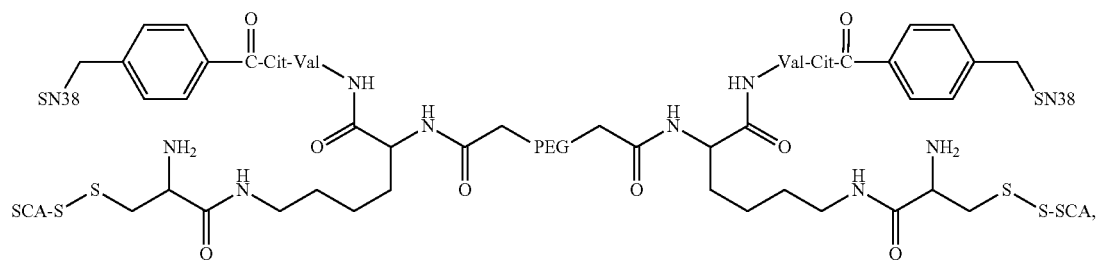
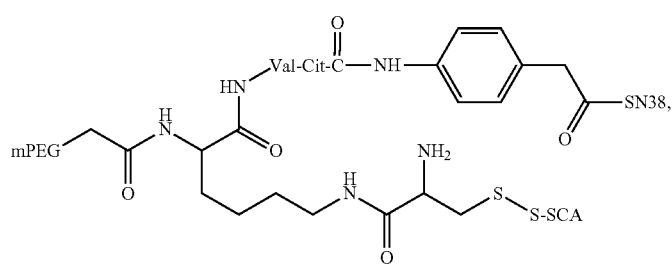
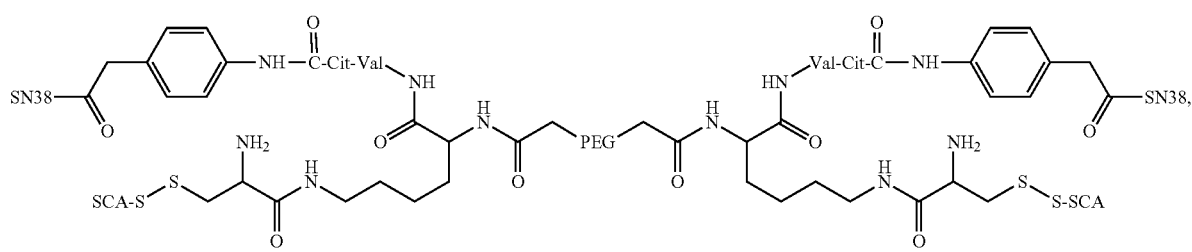

-continued
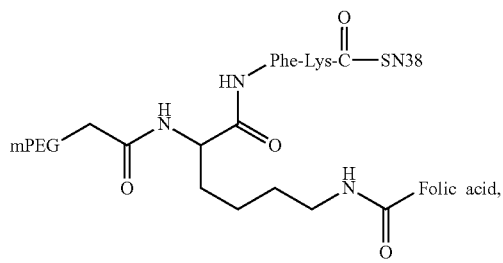
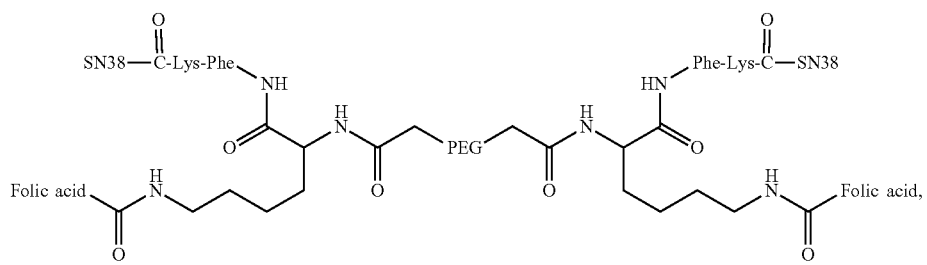
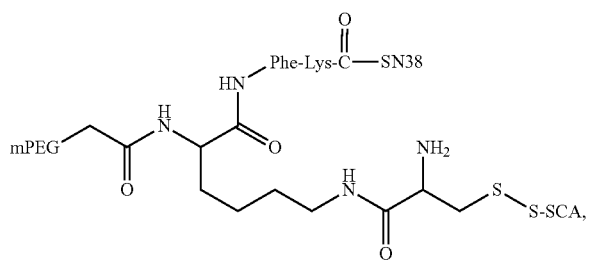
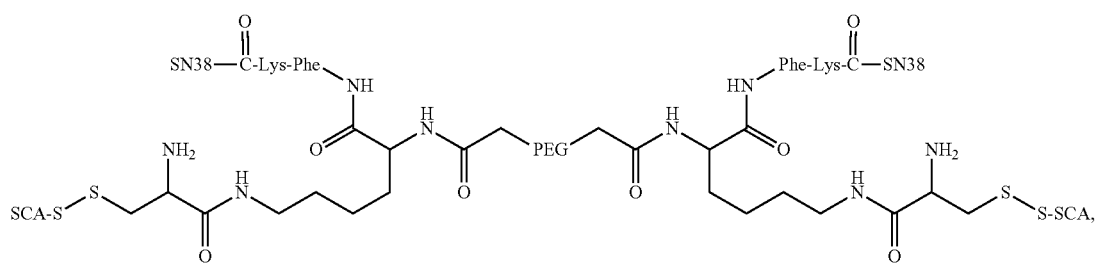
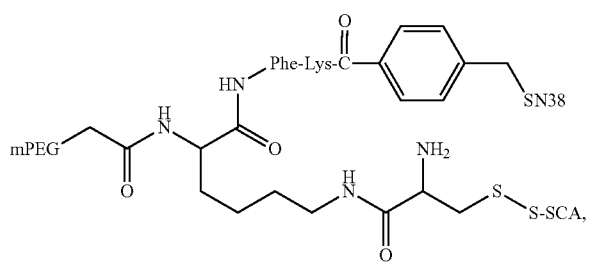
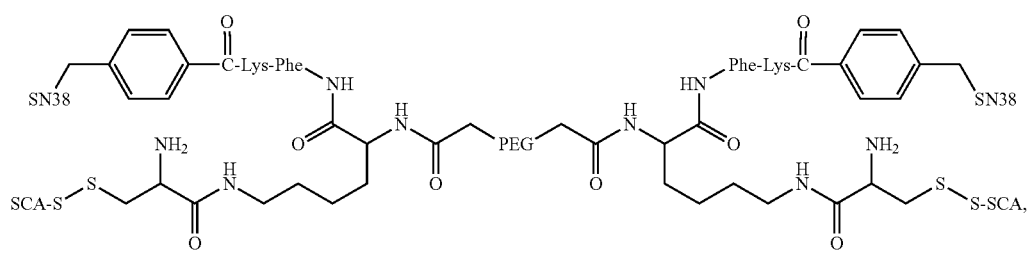

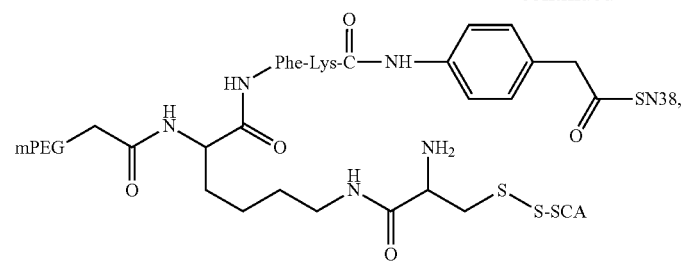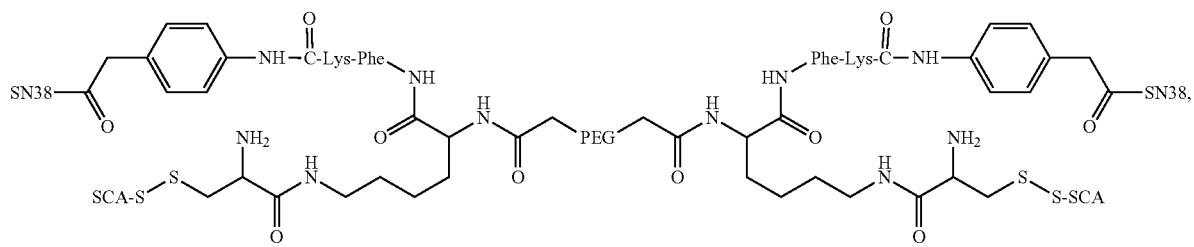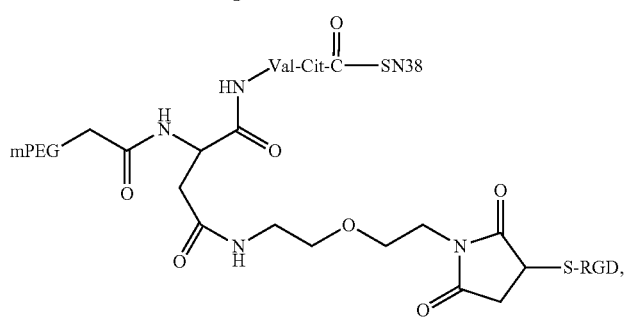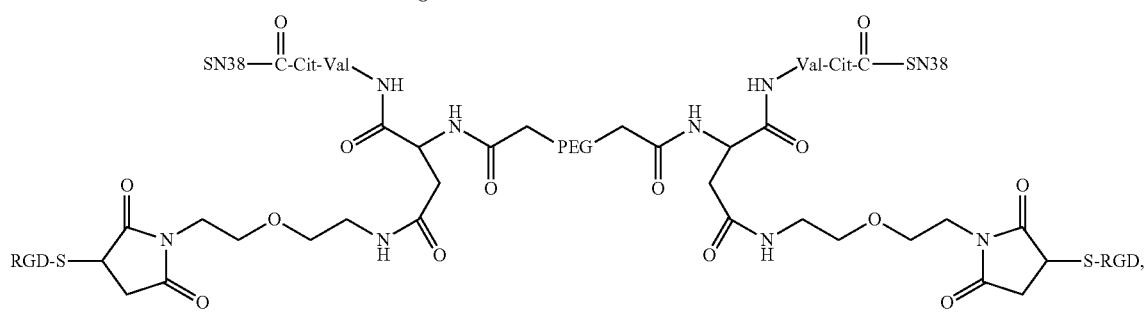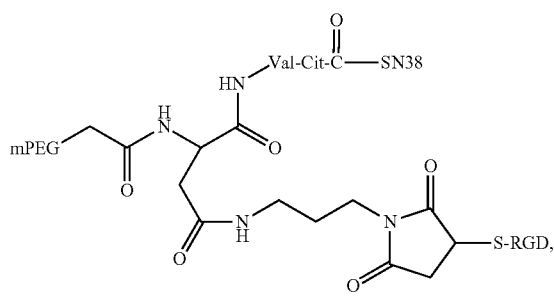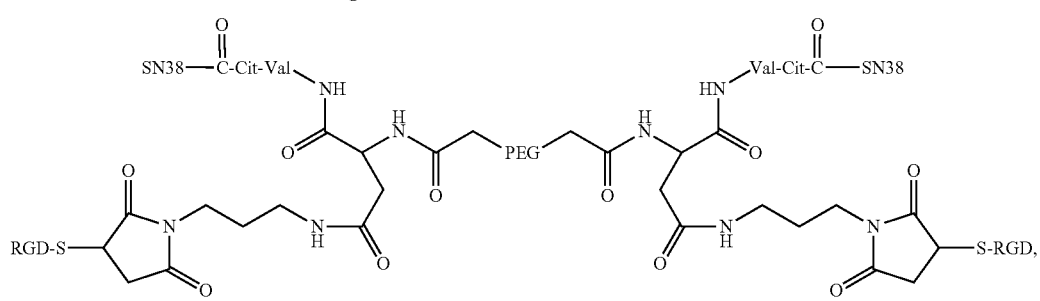

-continued
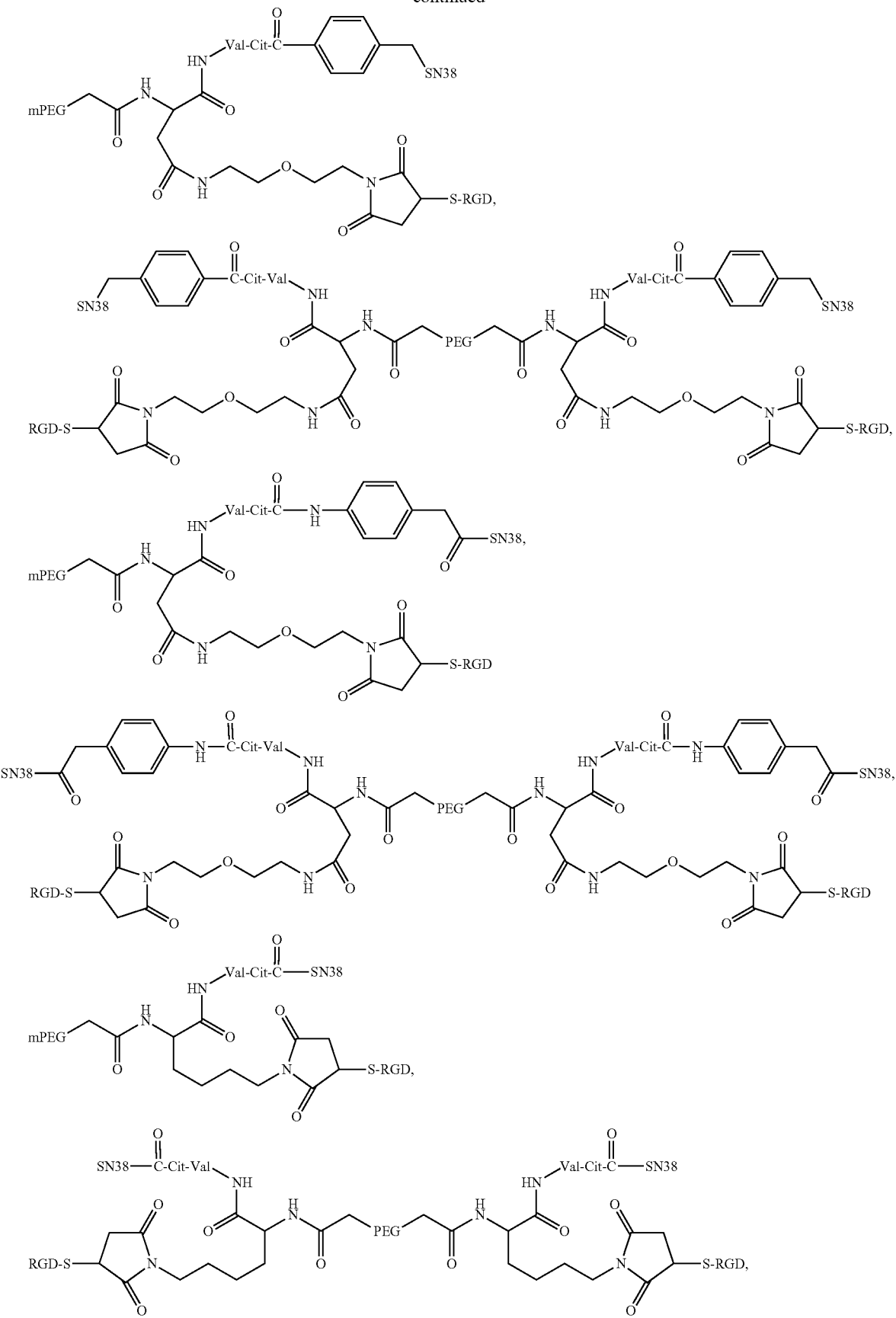

-continued
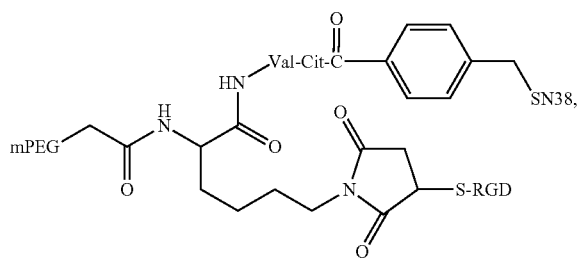
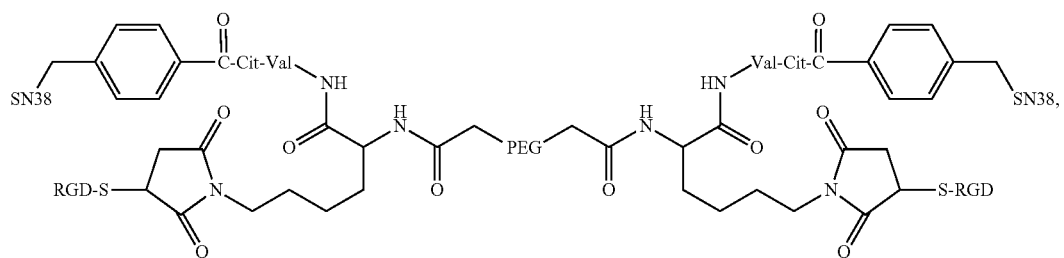
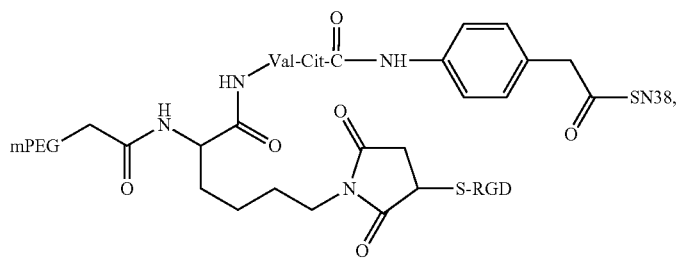
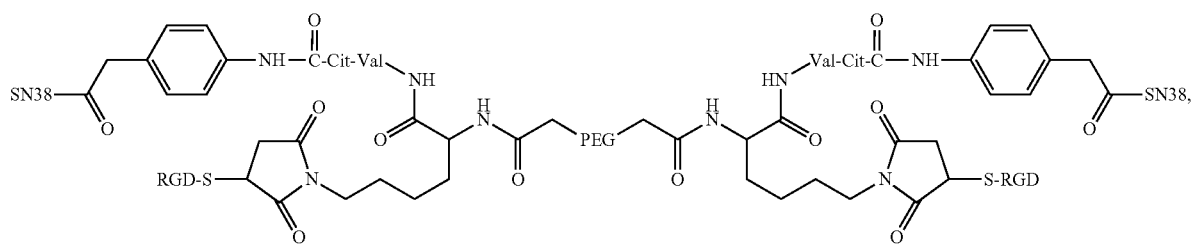
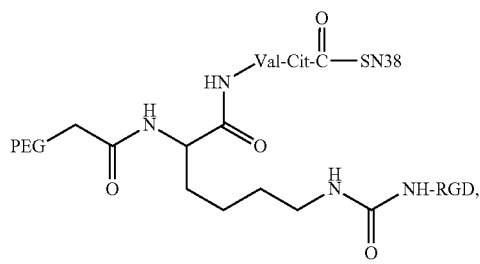
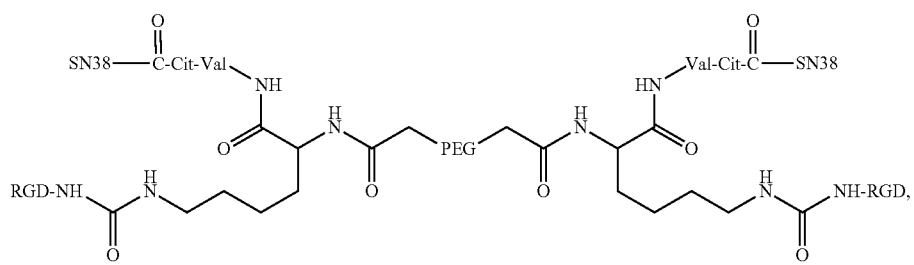

-continued
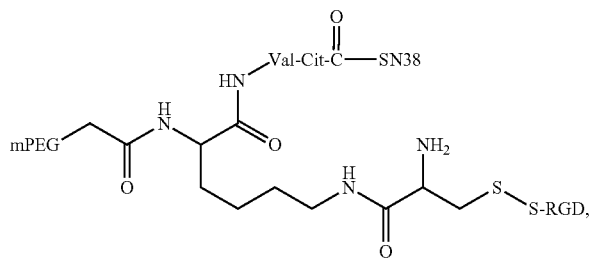
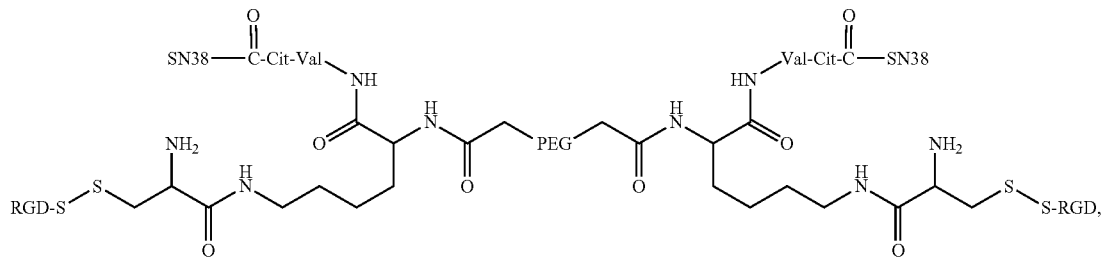
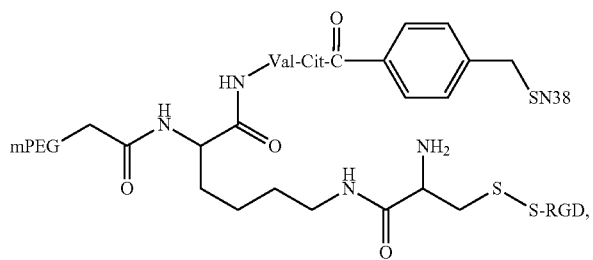
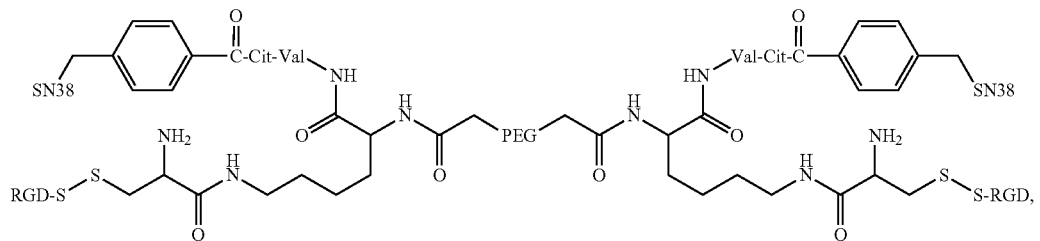
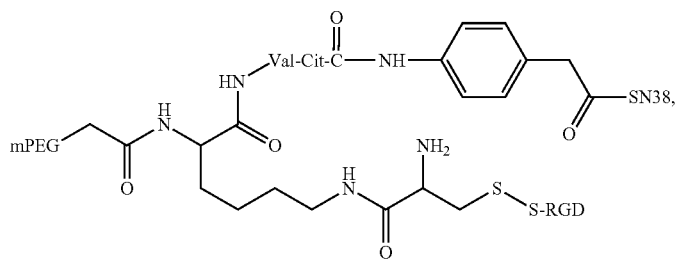
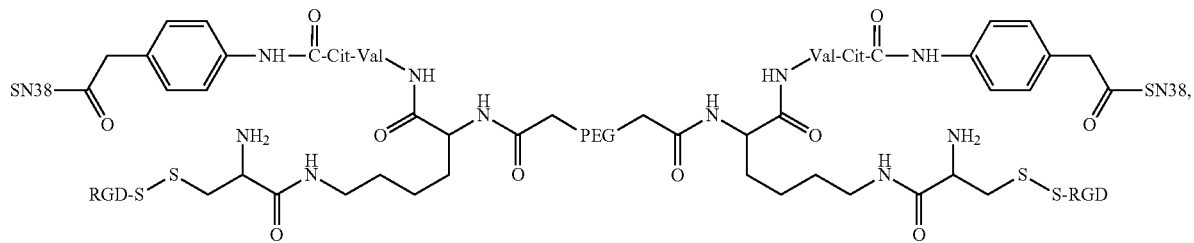

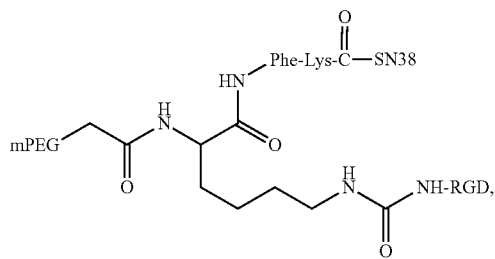
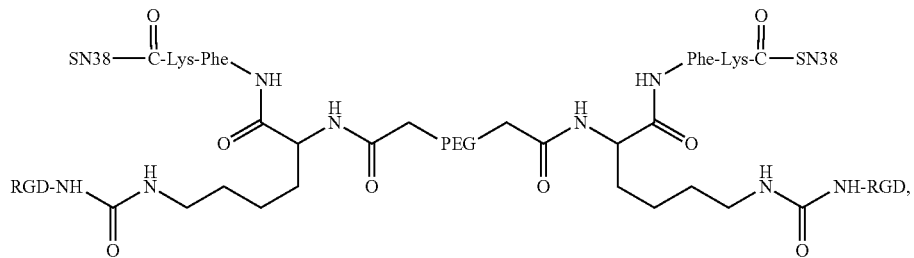
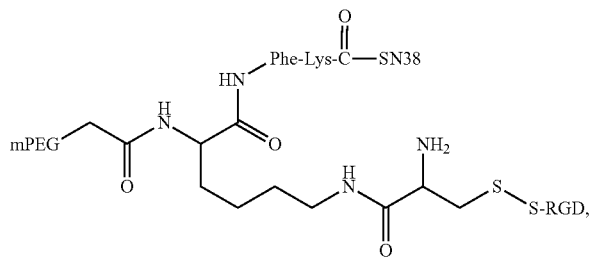
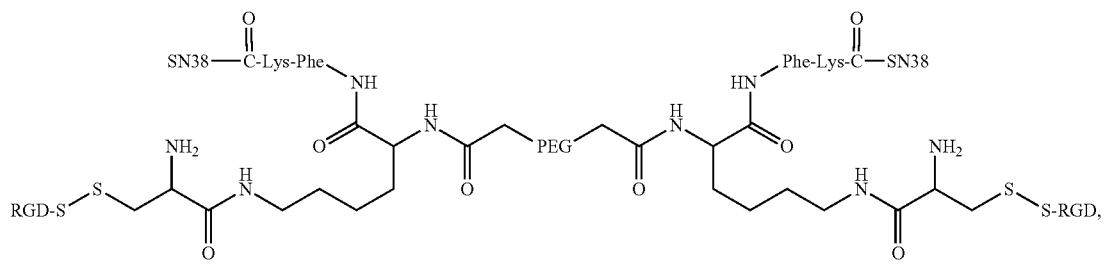
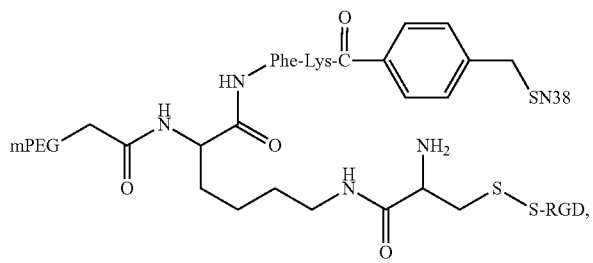
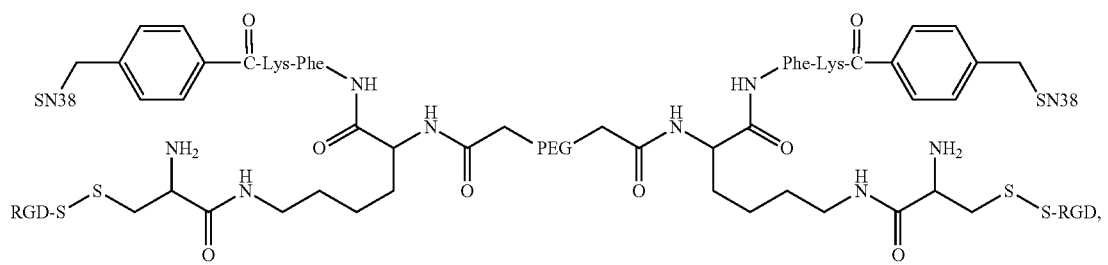

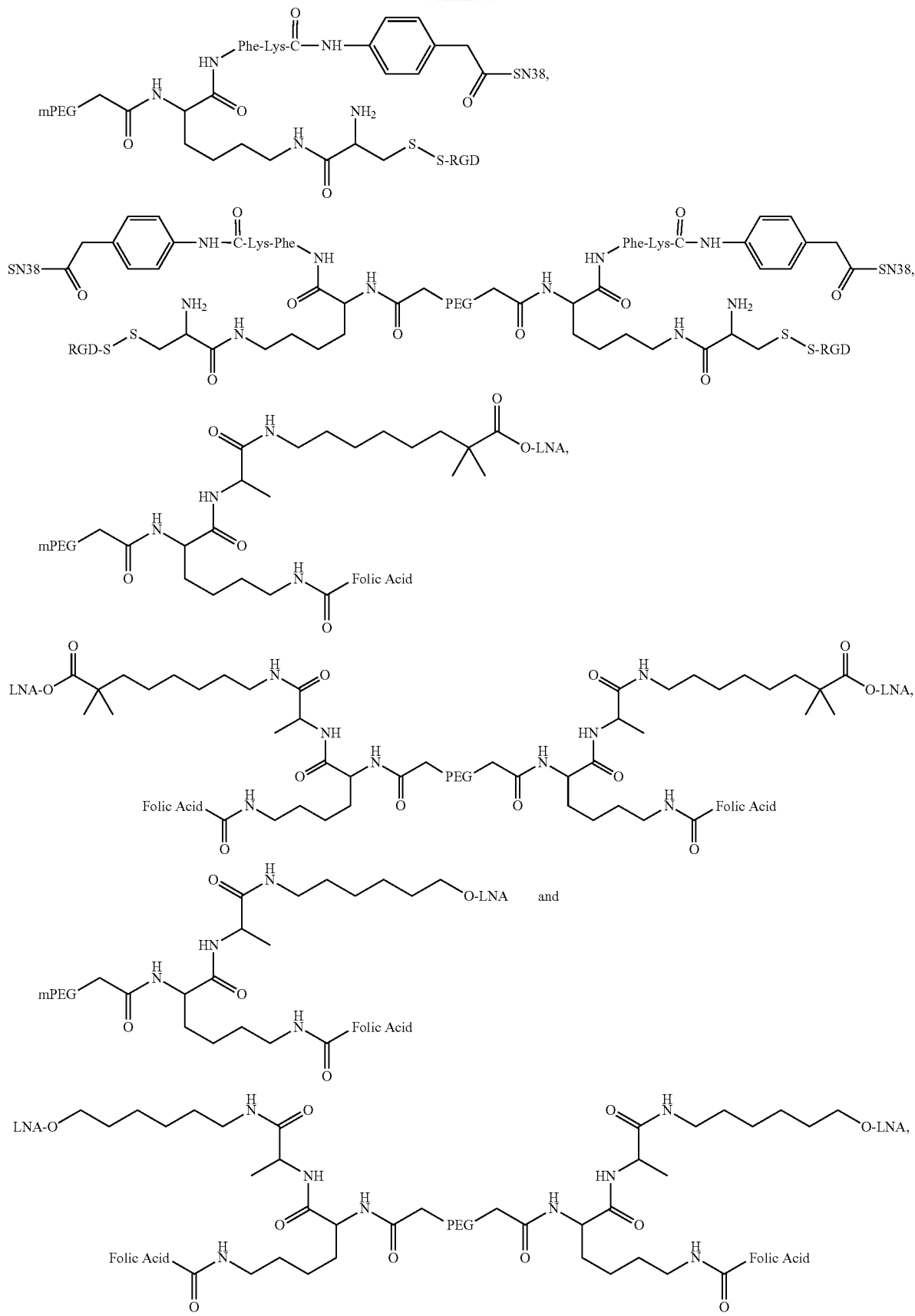

wherein
S-SCA is a single-chain antibody;
RGD is
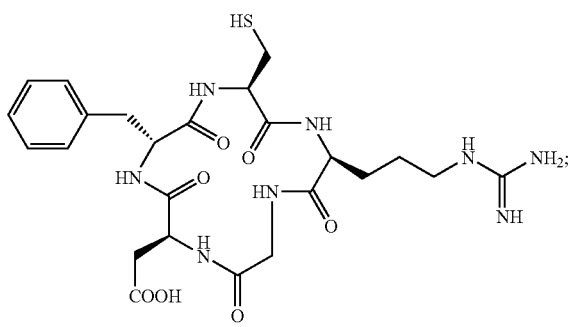 [SMILES: N=C(N)NCCC[C@@H]1NC(=O)[C@H](CS)NC(=O)[C@@H](Cc2ccccc2)NC(=O)[C@H](CC(=O)O)NC(=O)CNC1=O]
LNA is locked nucleic acids;
Folic acid is a residue of
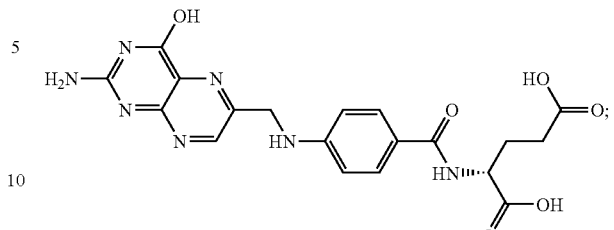
mPEG has the formula: $CH_3-O(CH_2CH_2O)_n-$;
PEG has the formula $-O(CH_2CH_2O)_n-$; and
(n) is a positive integer from about 10 to about 2,300.
* * * * *

SEQUENCE LISTING

<160> NUMBER OF SEQ ID NOS: 7

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Tyr Gly Arg Lys Lys Arg Arg Gln Arg Arg Arg
 1               5                  10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Arg Arg Arg Arg Arg Arg Arg Arg Arg
 1               5                  10

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)   (16)
<223> OTHER INFORMATION: Thiobackbone
<220> FEATURE:
<221> NAME/KEY: modified_base
<222> LOCATION: (1)
<223> OTHER INFORMATION: Methylated cytosine
<220> FEATURE:
<221> NAME/KEY: misc_feature
<222> LOCATION: (1)
<223> OTHER INFORMATION: LNA
<220> FEATURE:
<221> NAME/KEY: misc_feature
<222> LOCATION: (2)
<223> OTHER INFORMATION: LNA
<220> FEATURE:
<221> NAME/KEY: modified_base
<222> LOCATION: (3)
<223> OTHER INFORMATION: Methylated cytosine
<220> FEATURE:
<221> NAME/KEY: misc_feature
<222> LOCATION: (3)
<223> OTHER INFORMATION: LNA
<220> FEATURE:
<221> NAME/KEY: misc_feature
<222> LOCATION: (4)
<223> OTHER INFORMATION: LNA
<220> FEATURE:
<221> NAME/KEY: modified_base
<222> LOCATION: (13)
<223> OTHER INFORMATION: Methylated cytosine
<220> FEATURE:
<221> NAME/KEY: misc_feature
<222> LOCATION: (13)
<223> OTHER INFORMATION: LNA
<220> FEATURE:
<221> NAME/KEY: misc_feature
<222> LOCATION: (14)
<223> OTHER INFORMATION: LNA

```
<220> FEATURE:
<221> NAME/KEY: misc_feature
<222> LOCATION: (15)
<223> OTHER INFORMATION: LNA

<400> SEQUENCE: 3
ctcaatccat ggcagc                                                      16

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      Oligonucleotide
<220> FEATURE:
<221> NAME/KEY: misc_feature
<222> LOCATION: (1)    (19)
<223> OTHER INFORMATION: RNA

<400> SEQUENCE: 4
gcaugcggcc ucuguuugat t                                                21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)    (19)
<223> OTHER INFORMATION: RNA

<400> SEQUENCE: 5
ucaaacagag gccgcaugct t                                                21

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Thiobackbone

<400> SEQUENCE: 6
tctcccagcg tgcgccat                                                    18

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)    (16)
<223> OTHER INFORMATION: Thiobackbone
```

```
<220> FEATURE:
<221> NAME/KEY: misc_feature
<222> LOCATION: (1)   (3)
<223> OTHER INFORMATION: LNA
<220> FEATURE:
<221> NAME/KEY: misc_feature
<222> LOCATION: (13)  (15)
<223> OTHER INFORMATION: LNA

<400> SEQUENCE: 7
tggcaagcat cctgta                                         16
```